US008193207B2

(12) United States Patent
Zhuo et al.

(10) Patent No.: US 8,193,207 B2
(45) Date of Patent: Jun. 5, 2012

(54) LACTAM COMPOUNDS AND METHODS OF USING THE SAME

(75) Inventors: Jincong Zhuo, Boothwyn, PA (US);
Ding-Quan Qian, Newark, DE (US);
Wenqing Yao, Kennett Square, PA (US)

(73) Assignee: Incyte Corporation, Wilmington, DE (US)

( * ) Notice: Subject to any disclaimer, the term of this patent is extended or adjusted under 35 U.S.C. 154(b) by 1493 days.

(21) Appl. No.: 11/633,347

(22) Filed: Dec. 4, 2006

(65) Prior Publication Data

US 2007/0129345 A1    Jun. 7, 2007

Related U.S. Application Data

(60) Provisional application No. 60/742,353, filed on Dec. 5, 2005, provisional application No. 60/808,678, filed on May 26, 2006.

(51) Int. Cl.
*A61K 31/438* (2006.01)
*C07D 471/10* (2006.01)

(52) U.S. Cl. .......... 514/278; 546/16; 544/124; 544/242; 544/336; 514/231.5; 514/252; 514/256

(58) Field of Classification Search .................. 514/278, 514/231.5, 252, 256; 546/16; 544/124, 242, 544/336
See application file for complete search history.

(56) References Cited

U.S. PATENT DOCUMENTS

| | | | |
|---|---|---|---|
| 4,076,819 A | 2/1978 | Maffrand | |
| 4,439,606 A | 3/1984 | Du et al. | |
| 5,442,064 A | 8/1995 | Pieper et al. | |
| 5,614,534 A | 3/1997 | Binet et al. | |
| 5,633,247 A | 5/1997 | Baldwin et al. | |
| 5,668,138 A | 9/1997 | Baziard-Mouysset et al. | |
| 5,852,029 A | 12/1998 | Fisher et al. | |
| 5,981,754 A | 11/1999 | Badone et al. | |
| 6,547,958 B1 | 4/2003 | Elomari et al. | |
| 7,452,886 B2 * | 11/2008 | Betschart et al. | 514/252.15 |
| 7,655,670 B2 * | 2/2010 | Battista et al. | 514/278 |
| 2003/0229119 A1 | 12/2003 | Kym et al. | |
| 2005/0020645 A1 | 1/2005 | Ohta et al. | |
| 2005/0080078 A1 | 4/2005 | Aquila et al. | |
| 2005/0282858 A1 | 12/2005 | Yao et al. | |
| 2005/0288317 A1 | 12/2005 | Yao et al. | |
| 2005/0288329 A1 | 12/2005 | Yao et al. | |
| 2005/0288338 A1 | 12/2005 | Yao et al. | |
| 2006/0004049 A1 | 1/2006 | Yao et al. | |
| 2006/0009471 A1 | 1/2006 | Yao et al. | |
| 2006/0009491 A1 | 1/2006 | Yao et al. | |
| 2006/0019977 A1 | 1/2006 | Habashita et al. | |
| 2006/0106045 A1 | 5/2006 | Hughes et al. | |
| 2006/0116382 A1 | 6/2006 | Yao et al. | |
| 2006/0122197 A1 | 6/2006 | Yao et al. | |
| 2006/0122210 A1 | 6/2006 | Yao et al. | |
| 2006/0149070 A1 | 7/2006 | Rohde et al. | |
| 2006/0199816 A1 | 9/2006 | Gillespie et al. | |
| 2007/0066584 A1 | 3/2007 | Yao et al. | |
| 2007/0197506 A1 | 8/2007 | Yao et al. | |
| 2007/0197530 A1 | 8/2007 | Li et al. | |
| 2007/0208001 A1 | 9/2007 | Zhuo et al. | |
| 2007/0213311 A1 | 9/2007 | Li et al. | |
| 2007/0270424 A1 | 11/2007 | Li et al. | |
| 2007/0293529 A1 | 12/2007 | Li et al. | |

FOREIGN PATENT DOCUMENTS

| | | |
|---|---|---|
| DE | 2623567 | 12/1976 |
| EP | 0273659 | 7/1988 |
| EP | 0921125 | 6/1999 |
| EP | 1683797 | 7/2006 |
| JP | 4334357 | 11/1992 |
| WO | WO 01/30780 | 5/2001 |
| WO | WO 03/010138 | 2/2003 |
| WO | WO 03037847 | 5/2003 |
| WO | WO 03/053915 A2 | 7/2003 |
| WO | WO 03/104233 | 12/2003 |
| WO | WO 2004/058727 | 7/2004 |
| WO | WO 2004056745 | 7/2004 |
| WO | WO 2004065351 | 8/2004 |
| WO | WO 2004/076455 A1 * | 9/2004 |
| WO | WO 2004/082687 | 9/2004 |
| WO | WO 2004089470 | 10/2004 |
| WO | WO 2004089896 | 10/2004 |
| WO | WO 2005047286 | 5/2005 |
| WO | WO 2005/058890 | 6/2005 |
| WO | WO 2005060963 | 7/2005 |
| WO | WO 2005063745 | 7/2005 |
| WO | WO 2005/084667 | 9/2005 |
| WO | WO 2005108359 | 11/2005 |
| WO | WO 2006/020598 | 2/2006 |
| WO | WO 2006012226 | 2/2006 |
| WO | WO 2006/047196 | 5/2006 |

OTHER PUBLICATIONS

Bleicher, K. H. et al.: Parallel solution- and solid-phase synthesis of spirohydantoin derivatives as neurokinin-1 receptor ligands. Biorganic & Medicinal Chem. Lett., vol. 12, pp. 2519-2522, 2002.*
Alberts et al. Endocrinology (2003) 144: 4755-4762.
Albiston et al. (1994) Mol. Cell. Endocrin. 105: R11-R17.
Barf et al. (2002) J. Med. Chem. 45: 3813-3815.
Bellows et al. (1998) Bone 23: 119-125.
Bhargava et al., (2001), Endo 142: 1587-1594.
Billaudel and Sutter (1979) Horm. Metab. Res. 11: 555-560.
Bioreversible Carriers in Drug Design, ed. Edward B. Roche, American Pharmaceutical Association and Pergamon Press, 1987.
Blum, et al., (2003) Prog. Nucl. Acid Res. Mol. Biol. 75:173-216.
Bujalska et al. (1997) Lancet 349: 1210-1213.
Canalis (1996) J. Clin. Endocrinol. Metab. 81: 3441-3447.
Conn, (1955), J. Lab. Clin. Med. 45: 6-17.
Cooper et al. (2000) Bone 27: 375-381.

(Continued)

*Primary Examiner* — Charanjit Aulakh
(74) *Attorney, Agent, or Firm* — Fish & Richardson P.C.

(57) ABSTRACT

The present invention relates to inhibitors of 11-β hydroxyl steroid dehydrogenase type 1 and pharmaceutical compositions thereof. The compounds of the invention can be useful in the treatment of various diseases associated with expression or activity of 11-β hydroxyl steroid dehydrogenase type 1.

56 Claims, No Drawings

OTHER PUBLICATIONS

Database CAPLUS on STN (Columbus, OH, USA) No. 108:131815, Preparation and testing of f7-amino-1,3-dihydro-2H-imidazo[4,5-b]quinolin-2-ones as phosphodiesterase and bloodplatelet aggregation inhibitors, abstract, Meanwell, et al. (1988) see RN 113288-90-7.

Database CAPLUS on STN (Columbus, OH, USA) No. 118:255342, {re[artopm pf M-heterpcuc;u;carbpmu;a,omp acids and analogs as prolylendopeptidase inhibotors' abstract, Hosoda et al. (1993) see RN 147635-61-8.

Database CAPLUS on STN (Columbus, OH, USA) No. 126:317635, "Alpha-amino acids derived from ornithine as building blocks for peptide synthesis" abstract, Gescrinier et al. j. Pep. Res. 49(2):183-189 (1997).

Database CAPLUS on STN (Columbus, OH, USA) No. 143:78479, "Preparation of amino acid derivatives as novel M3 muscarinic acetylcholine receptor antagonists" abstract, Busch et al. (2005), see RN 902149-23-9 and 854750-92-8.

Davani et al. (2000) J. Biol. Chem. 275: 34841-34844.
Draper et al. (2003) Nat. Genet. 34: 434-439.
Edwards et al. (1988) Lancet 2: 986-989.
Engeli, et al., (2004) Obes. Res. 12: 9-17.
Funder et al. (1988), Science 242: 583-585.
Greene, et al., Protective Groups in Organic Synthesis, 2d. Ed., Wiley & Sons, 1991.
Gu et al., "Discovery of 4-heteroarylbicyclo[2.2.2]octyltriazoles as potent and selective inhibitors of 11β-HSD1: Novel therapeutic agents for the treatment of metabolic syndrome," *Bioorg. Med. Chem. Lett.*, 15:5266-5269 (2005).
Hermanowski-Vosatka et al. (2005) J. Exp. Med. 202: 517-527.
Jausons-Loffreda et al. J. Biolumin and Chemilumin, 9:217-221 (1994).
Journal of Pharmaceutical Science, 66, 2 (1977).
Kotelevstev et al. (1997) Proc. Natl. Acad. Sci. 94: 14924-14929.
Kurukulasuriya, et al., (2003) Curr. Med. Chem. 10: 123-53.
Leonardi et al., "Synthesis, Pharmacological Evaluation, and Structure—Activity Relationship and Quantitative Structure—Activity Relationship Studies on Novel Derivatives of 2,4-Diamino-6,7-dimethoxyquinazoline $\alpha_1$-Adrenoceptor Antagonists," *J. Med. Chem.*, 42:427-437 (1999).
Lindsay et al. (2003) J. Clin. Endocrinol. Metab. 88: 2738-2744.
Livingstone et al. (2000) Endocrinology 131: 560-563.
Low et al. (1994) J. Mol. Endocrin. 13: 167-174.
Lupien et al. (1998) Nat. Neurosci. 1: 69-73.
Mallams et al., "Inhibitors of Farnesyl Protein Transferase. 4-Amido, 4-Carbamoyl, and 4-Carboxamido Derivatives of 1-(8-Chloro-6,11-dihydro-5*H*-benzo[5,6]-cyclohepta[1,2-*b*]pyridin-11-yl)piperazine and 1-(3-Bromo-8-chloro-6,11-dihydro-5*H*-benzo[5,6]cyclohepta[1,2-*b*]pyridin-11-yl)piperazine,"*J. Med. Chem.*, 41:877-893 (1998).
Masuzaki et al. (2001) Science 294: 2166-2170.
Masuzaki et al. (2003) J. Clinical Invest. 112: 83-90.
Masuzaki, et al., (2003) Curr. Drug Targets Immune Endocr. Metabol. Disord. 3: 255-62.
Matsuzawa et al. (1999) Ann. N.Y. Acad. Sci. 892: 146-154.
McEwen and Sapolsky (1995) Curr. Opin. Neurobiol. 5: 205-216.
Miller and Chrousos (2001) Endocrinology and Metabolism, eds. Felig and Frohman (McGraw-Hill, New York), 4th Ed.: 387-524.
Moeller et al., "Anodic Amide Oxidations in the Presence of Electron-Rich Phenyl Rings: Evidence for an Intramolecular Electron-Transfer Mechanism," *J. Org. Chem.*, 56:1058-1067 (1991).
Morton et al. (2001) J. Biol. Chem. 276: 41293-41300.
Morton et al. (2004) Diabetes 53: 931-938.
Ogawa et al. (1992) J. Clin. Invest. 90: 497-504.
Pitt et al., New England J. Med. (1999), 341: 709-719.
Pitt et al., New England J. Med. (2003), 348: 1309-1321.
Rajan et al. (1996) J. Neurosci. 16: 65-70.
Rask et al. (2001) J. Clin. Endocrinol. Metab. 86: 1418-1421.
Rauz et al. (2001) Invest. Ophthalmol. Vis. Sci. 42: 2037-2042.
Reaven (1993) Ann. Rev. Med. 44: 121-131.
Remington's Pharmaceutical Sciences, 17th ed., Mack Publishing Company, Easton, Pa., 1985, p. 1418.
Sandeep et al. (2004) Proc. Natl. Acad. Sci. 101: 6734-6739.
Stokes et al. (2000) Invest. Ophthalmol. Vis. Sci. 41: 1629-1683.
T. Higuchi and V. Stella, "Pro-drugs as Novel Delivery Systems," vol. 14 of the A.C.S. Symposium Series, and in Bioreversible Carriers in Drug Design, ed. Edward B. Roche, American Pharmaceutical Association and Pergamon Press, 1987.
Wajchenberg, B.L. (2000) Endocrine Reviews 21: 697-738.
Wake et al. (2003) J. Clin. Endocrinol. Metab. 88: 3983-3988.
Walker et al. (1979) Hypertension 1: 287-291.
Wilson et al. (1998) Proc. Natl. Acad. Sci. 95: 10200-10205.
Yau et al. (2001) Proc. Natl. Acad. Sci. 98: 4716-4721.
Yeh et al., "Discovery of orally active butyrolactam 11β-HSD1 inhibitors," *Bioorg. Med. Chem. Lett.*, 16:5555-5560 (2006).
Yeh et al., "Synthesis and biological evaluation of heterocycle containing adamantine 11β-HSD1 inhibitors," *Bioorg. Med. Chem. Lett.*, 16:5414-5419 (2006).
Database CAPLUS on STN (Columbus, OH, USA) No. 143:7612, Preparation of Heterocyclic Spiro Compounds for Treatment of Stress Related Diseases, RN 64097-78-5, (2005).
Database CAPLUS on STN (Columbus, OH, USA) No. 135:257227, "Preparation of pyrrolidinone derivatives having .sigma.-receptor affinity", RN-362518-14-7, RN 362518-16-9, RN 362518-15-8, RN 363518-17-0; (2001).
Database CAPLUS on STN (Columbus, OH, USA) No. 55:87498, "Synthetic drugs. VI. A new type of spirosuccinimade", RN-64097-71-8; RN-102654-82-0; RN-113251-47-1, RN-113687-61-9, RN-114509-25-0; (1961).
International Search Repot and Written Opinion for PCT/US2006/046309, dated Jul. 9, 2007.
Mehrotra, M. et al., "Discovery of Novel 2,8-Diazaspiro[4,5]decanes as orally Active Glycoprotein IIb-IIIa Antagonist", J. Med. Chem.., 47 pp. 2037-2061, 2004.
Suess, R. *Helvetica Chimica Acta* vol. 60(5), 1977-Nr.165.
Stulnig, T. M. and Waldhäusl, W., "11β-Hydroxysteroid dehydrogenase Type 1 in obesity and Type 2 Diabetes", *Diabetologia*, (2004) 47:1-11.
International Preliminary Report on Patentability and Written Opinion dated Jun. 11, 2008 for International Appln. No. PCT/US2006/046309 (10 pgs.).
International Preliminary Report on Patentability and Written Opinion dated Feb. 13, 2007 for International Appln. No. PCT/US2005/028201 (6 pgs.).
International Preliminary Report on Patentability and Written Opinion dated Aug. 5, 2008 for International Appln. No. PCT/US2005/002360 (7 pgs.).
International Search Report and Written Opinion dated Nov. 6, 2006 for International Appln. No. PCT/US2005/028201 (12 pgs.).
International Search Report and Written Opinion dated Jun. 19, 2007 for International Appln. No. PCT/US2007/002360 (11 pgs.).

\* cited by examiner

LACTAM COMPOUNDS AND METHODS OF USING THE SAME

CROSS REFERENCE TO RELATED APPLICATIONS

This application claims the benefit of U.S. Ser. No. 60/742,353, filed Dec. 5, 2005, and U.S. Ser. No. 60/808,678, filed May 26, 2006, the disclosures of each of which are incorporated herein by reference in their entireties.

FIELD OF THE INVENTION

The present invention relates to modulators of 11-β hydroxyl steroid dehydrogenase type 1 (11βHSD1), compositions thereof, and methods of using the same.

BACKGROUND OF THE INVENTION

Glucocorticoids are steroid hormones that have the ability to modulate a plethora of biological processes including development, neurobiology, inflammation, blood pressure, and metabolism. In humans, the primary endogenously produced glucocorticoid is cortisol. Two members of the nuclear hormone receptor superfamily, glucocorticoid receptor (GR) and mineralcorticoid receptor (MR), are the key mediators of cortisol function in vivo. These receptors possess the ability to directly modulate transcription via DNA-binding zinc finger domains and transcriptional activation domains. This functionality, however, is dependent on the receptor having first bound to ligand (cortisol); as such, these receptors are often referred to as 'ligand-dependent transcription factors'.

Cortisol is synthesized in the zona fasciculate of the adrenal cortex under the control of a short-term neuroendocrine feedback circuit called the hypothalamic-pituitary-adrenal (HPA) axis. Adrenal production of cortisol proceeds under the control of adrenocorticotrophic hormone (ACTH), a factor produced and secreted by the anterior pituitary. Production of ACTH in the anterior pituitary is itself highly regulated, being driven by corticotropin releasing hormone (CRH) produced by the paraventricular nucleus of the hypothalamus. The HPA axis functions to maintain circulating cortisol concentrations within restricted limits, with forward drive at the diurnal maximum or during periods of stress being rapidly attenuated by a negative feedback loop resulting from the ability of cortisol to suppress ACTH production in the anterior pituitary and CRH production in the hypothalamus.

The importance of the HPA axis in controlling glucocorticoid excursions is evident from the fact that disruption of this homeostasis by either excess or deficient secretion or action results in Cushing's syndrome or Addison's disease, respectively (Miller and Chrousos (2001) Endocrinology and Metabolism, eds. Felig and Frohman (McGraw-Hill, New York), 4$^{th}$ Ed.: 387-524). Interestingly, the phenotype of Cushing's syndrome patients closely resembles that of Reaven's metabolic syndrome (also known as Syndrome X or insulin resistance syndrome) including visceral obesity, glucose intolerance, insulin resistance, hypertension, and hyperlipidemia (Reaven (1993) Ann. Rev. Med. 44: 121-131). Paradoxically, however, circulating glucocorticoid levels are typically normal in metabolic syndrome patients.

For decades, the major determinants of glucocorticoid action were believed to be limited to three primary factors: 1) circulating levels of glucocorticoid (driven primarily by the HPA axis), 2) protein binding of glucocorticoids in circulation (upward of 95%), and 3) intracellular receptor density inside target tissues. Recently, a fourth determinant of glucocorticoid function has been identified: tissue-specific pre-receptor metabolism. The enzymes 11-beta hydroxysteroid dehydrogenase type 1 (11βHSD1) and 11-beta hydroxysteroid dehydrogenase type 2 (11βHSD2) catalyze the interconversion of active cortisol (corticosterone in rodents) and inactive cortisone (11-dehydrocorticosterone in rodents). 11βHSD1 has been shown to be an NADPH-dependent reductase, catalyzing the activation of cortisol from inert cortisone (Low et al. (1994) J. Mol. Endocrin. 13: 167-174); conversely, 11βHSD2 is an NAD-dependent dehydrogenase, catalyzing the inactivation of cortisol to cortisone (Albiston et al. (1994) Mol. Cell. Endocrin. 105: R11-R17). The activity of these enzymes has profound consequences on glucocorticoid biology as evident by the fact that mutations in either gene cause human pathology. For example, 11βHSD2 is expressed in aldosterone-sensitive tissues such as the distal nephron, salivary gland, and colonic mucosa where its cortisol dehydrogenase activity serves to protect the intrinsically non-selective mineralcorticoid receptor from illicit occupation by cortisol (Edwards et al. (1988) Lancet 2: 986-989). Individuals with mutations in 11βHSD2 are deficient in this cortisol-inactivation activity and, as a result, present with a syndrome of apparent mineralcorticoid excess (also referred to as 'SAME') characterized by hypertension, hypokalemia, and sodium retention (Wilson et al. (1998) Proc. Natl. Acad. Sci. 95: 10200-10205). Likewise, mutations in 11βHSD1 and a co-localized NADPH-generating enzyme, hexose 6-phosphate dehydrogenase (H6PD), can result in cortisone reductase deficiency (also known as CRD; Draper et al. (2003) Nat. Genet. 34: 434-439). CRD patients excrete virtually all glucocorticoids as cortisone metabolites (tetrahydrocortisone) with low or absent cortisol metabolites (tetrahydrocortisols). When challenged with oral cortisone, CRD patients exhibit abnormally low plasma cortisol concentrations. These individuals present with ACTH-mediated androgen excess (hirsutism, menstrual irregularity, hyperandrogenism), a phenotype resembling polycystic ovary syndrome (PCOS).

Given the ability of 11βHSD1 to regenerate cortisol from inert circulating cortisone, considerable attention has been given to its role in the amplification of glucocorticoid function. 11βHSD1 is expressed in many key GR-rich tissues, including tissues of considerable metabolic importance such as liver, adipose, and skeletal muscle, and, as such, has been postulated to aid in the tissue-specific potentiation of glucocorticoid-mediated antagonism of insulin function. Considering a) the phenotypic similarity between glucocorticoid excess (Cushing's syndrome) and the metabolic syndrome with normal circulating glucocorticoids in the latter, as well as b) the ability of 11βHSD1 to generate active cortisol from inactive cortisone in a tissue-specific manner, it has been suggested that central obesity and the associated metabolic complications in syndrome X result from increased activity of 11βHSD1 within adipose tissue, resulting in 'Cushing's disease of the omentum' (Bujalska et al. (1997) Lancet 349: 1210-1213). Indeed, 11βHSD1 has been shown to be upregulated in adipose tissue of obese rodents and humans (Livingstone et al. (2000) Endocrinology 131: 560-563; Rask et al. (2001) J. Clin. Endocrinol. Metab. 86: 1418-1421; Lindsay et al. (2003) J. Clin. Endocrinol. Metab. 88: 2738-2744; Wake et al. (2003) J. Clin. Endocrinol. Metab. 88: 3983-3988).

Additional support for this notion has come from studies in mouse transgenic models. Adipose-specific overexpression of 11βHSD1 under the control of the aP2 promoter in mouse produces a phenotype remarkably reminiscent of human metabolic syndrome (Masuzaki et al. (2001) Science 294: 2166-2170; Masuzaki et al. (2003) J. Clinical Invest. 112:

83-90). Importantly, this phenotype occurs without an increase in total circulating corticosterone, but rather is driven by a local production of corticosterone within the adipose depots. The increased activity of 11βHSD1 in these mice (2-3 fold) is very similar to that observed in human obesity (Rask et al. (2001) J. Clin. Endocrinol. Metab. 86: 1418-1421). This suggests that local 11βHSD1-mediated conversion of inert glucocorticoid to active glucocorticoid can have profound influences whole body insulin sensitivity.

Based on this data, it would be predicted that the loss of 11βHSD1 would lead to an increase in insulin sensitivity and glucose tolerance due to a tissue-specific deficiency in active glucocorticoid levels. This is, in fact, the case as shown in studies with 11βHSD1-deficient mice produced by homologous recombination (Kotelevstev et al. (1997) Proc. Natl. Acad. Sci. 94: 14924-14929; Morton et al. (2001) J. Biol. Chem. 276: 41293-41300; Morton et al. (2004) Diabetes 53: 931-938). These mice are completely devoid of 11-keto reductase activity, confirming that 11βHSD1 encodes the only activity capable of generating active corticosterone from inert 11-dehydrocorticosterone. 11βHSD1-deficient mice are resistant to diet- and stress-induced hyperglycemia, exhibit attenuated induction of hepatic gluconeogenic enzymes (PEPCK, G6P), show increased insulin sensitivity within adipose, and have an improved lipid profile (decreased triglycerides and increased cardio-protective HDL). Additionally, these animals show resistance to high fat diet-induced obesity. Further, adipose-tissue overexpression of the 11-beta dehydrogenase enzyme, 11bHSD2, which inactivates intracellular corticosterone to 11-dehydrocorticosterone, similarly attenuates weight gain on high fat diet, improves glucose tolerance, and heightens insulin sensitivity. Taken together, these transgenic mouse studies confirm a role for local reactivation of glucocorticoids in controlling hepatic and peripheral insulin sensitivity, and suggest that inhibition of 11βHSD1 activity may prove beneficial in treating a number of glucocorticoid-related disorders, including obesity, insulin resistance, hyperglycemia, and hyperlipidemia.

Data in support of this hypothesis has been published. Recently, it was reported that 11βHSD1 plays a role in the pathogenesis of central obesity and the appearance of the metabolic syndrome in humans. Increased expression of the 11βHSD1 gene is associated with metabolic abnormalities in obese women and that increased expression of this gene is suspected to contribute to the increased local conversion of cortisone to cortisol in adipose tissue of obese individuals (Engeli, et al., (2004) Obes. Res. 12: 9-17).

A new class of 11βHSD1 inhibitors, the arylsulfonamidothiazoles, was shown to improve hepatic insulin sensitivity and reduce blood glucose levels in hyperglycemic strains of mice (Barf et al. (2002) J. Med. Chem. 45: 3813-3815; Alberts et al. Endocrinology (2003) 144: 4755-4762). Additionally, it was recently reported that these selective inhibitors of 11βHSD1 can ameliorate severe hyperglycemia in genetically diabetic obese mice. Data using a structurally distinct series of compounds, the adamantyl triazoles (Hermanowski-Vosatka et al. (2005) J. Exp. Med. 202: 517-527), also indicates efficacy in rodent models of insulin resistance and diabetes, and further illustrates efficacy in a mouse model of atherosclerosis, perhaps suggesting local effects of corticosterone in the rodent vessel wall. Thus, 11βHSD1 is a promising pharmaceutical target for the treatment of the Metabolic Syndrome (Masuzaki, et al., (2003) Curr. Drug Targets Immune Endocr. Metabol. Disord. 3: 255-62).

A. Obesity and Metabolic Syndrome

As described above, multiple lines of evidence suggest that inhibition of 11βHSD1 activity can be effective in combating obesity and/or aspects of the metabolic syndrome cluster, including glucose intolerance, insulin resistance, hyperglycemia, hypertension, hyperlipidemia, and/or atherosclerosis/coronary heart disease. Glucocorticoids are known antagonists of insulin action, and reductions in local glucocorticoid levels by inhibition of intracellular cortisone to cortisol conversion should increase hepatic and/or peripheral insulin sensitivity and potentially reduce visceral adiposity. As described above, 11βHSD1 knockout mice are resistant to hyperglycemia, exhibit attenuated induction of key hepatic gluconeogenic enzymes, show markedly increased insulin sensitivity within adipose, and have an improved lipid profile. Additionally, these animals show resistance to high fat diet-induced obesity (Kotelevstev et al. (1997) Proc. Natl. Acad. Sci. 94: 14924-14929; Morton et al. (2001) J. Biol. Chem. 276: 41293-41300; Morton et al. (2004) Diabetes 53: 931-938). In vivo pharmacology studies with multiple chemical scaffolds have confirmed the critical role for 11βHSD1 in regulating insulin resistance, glucose intolerance, dyslipidemia, hypertension, and atherosclerosis. Thus, inhibition of 11βHSD1 is predicted to have multiple beneficial effects in the liver, adipose, skeletal muscle, and heart, particularly related to alleviation of component(s) of the metabolic syndrome, obesity, and/or coronary heart disease.

B. Pancreatic Function

Glucocorticoids are known to inhibit the glucose-stimulated secretion of insulin from pancreatic beta-cells (Billaudel and Sutter (1979) Horm. Metab. Res. 11: 555-560). In both Cushing's syndrome and diabetic Zucker fa/fa rats, glucose-stimulated insulin secretion is markedly reduced (Ogawa et al. (1992) J. Clin. Invest. 90: 497-504). 11 PHSD 1 mRNA and activity has been reported in the pancreatic islet cells of ob/ob mice and inhibition of this activity with carbenoxolone, an 11βHSD1 inhibitor, improves glucose-stimulated insulin release (Davani et al. (2000) J. Biol. Chem. 275: 34841-34844). Thus, inhibition of 11βHSD1 is predicted to have beneficial effects on the pancreas, including the enhancement of glucose-stimulated insulin release and the potential for attenuating pancreatic beta-cell decompensation.

C. Cognition and Dementia

Mild cognitive impairment is a common feature of aging that may be ultimately related to the progression of dementia. In both aged animals and humans, inter-individual differences in general cognitive function have been linked to variability in the long-term exposure to glucocorticoids (Lupien et al. (1998) Nat. Neurosci. 1: 69-73). Further, dysregulation of the HPA axis resulting in chronic exposure to glucocorticoid excess in certain brain subregions has been proposed to contribute to the decline of cognitive function (McEwen and Sapolsky (1995) Curr. Opin. Neurobiol. 5: 205-216). 11βHSD1 is abundant in the brain, and is expressed in multiple subregions including the hippocampus, frontal cortex, and cerebellum (Sandeep et al. (2004) Proc. Natl. Acad. Sci. 101(17): 6734-6739). Treatment of primary hippocampal cells with the 11βHSD1 inhibitor carbenoxolone protects the cells from glucocorticoid-mediated exacerbation of excitatory amino acid neurotoxicity (Rajan et al. (1996) J. Neurosci. 16: 65-70). Additionally, 11βPHSD1-deficient mice are protected from glucocorticoid-associated hippocampal dysfunction that is associated with aging (Yau et al. (2001) Proc. Natl. Acad. Sci. 98: 4716-4721). In two randomized, double-blind, placebo-controlled crossover studies, administration of carbenoxolone improved verbal fluency and verbal memory (Sandeep et al. (2004) Proc. Natl. Acad. Sci. 101(17): 6734-6739). Thus, inhibition of 11βHSD1 is predicted to reduce exposure to glucocorticoids in the brain and protect against deleterious glucocorticoid effects on neuronal function, including cognitive impairment, dementia, and/or depression.

D. Intra-Ocular Pressure

Glucocorticoids can be used topically and systemically for a wide range of conditions in clinical ophthalmology. One particular complication with these treatment regimens is corticosteroid-induced glaucoma. This pathology is characterized by a significant increase in intra-ocular pressure (IOP). In its most advanced and untreated form, IOP can lead to partial visual field loss and eventually blindness. IOP is produced by the relationship between aqueous humour production and drainage. Aqueous humour production occurs in the non-pigmented epithelial cells (NPE) and its drainage is through the cells of the trabecular meshwork. 11βHSD1 has been localized to NPE cells (Stokes et al. (2000) Invest. Ophthalmol. Vis. Sci. 41: 1629-1683; Rauz et al. (2001) Invest. Ophthalmol. Vis. Sci. 42: 2037-2042) and its function is likely relevant to the amplification of glucocorticoid activity within these cells. This notion has been confirmed by the observation that free cortisol concentration greatly exceeds that of cortisone in the aqueous humour (14:1 ratio). The functional significance of 11βHSD1 in the eye has been evaluated using the inhibitor carbenoxolone in healthy volunteers (Rauz et al. (2001) Invest. Ophthalmol. Vis. Sci. 42: 2037-2042). After seven days of carbenoxolone treatment, IOP was reduced by 18%. Thus, inhibition of 11βHSD1 in the eye is predicted to reduce local glucocorticoid concentrations and IOP, producing beneficial effects in the management of glaucoma and other visual disorders.

E. Hypertension

Adipocyte-derived hypertensive substances such as leptin and angiotensinogen have been proposed to be involved in the pathogenesis of obesity-related hypertension (Matsuzawa et al. (1999) Ann. N.Y. Acad. Sci. 892: 146-154; Wajchenberg (2000) Endocr. Rev. 21: 697-738). Leptin, which is secreted in excess in aP2-11βHSD1 transgenic mice (Masuzaki et al. (2003) J. Clinical Invest. 112: 83-90), can activate various sympathetic nervous system pathways, including those that regulate blood pressure (Matsuzawa et al. (1999) Ann. N.Y. Acad. Sci. 892: 146-154). Additionally, the renin-angiotensin system (RAS) has been shown to be a major determinant of blood pressure (Walker et al. (1979) Hypertension 1: 287-291). Angiotensinogen, which is produced in liver and adipose tissue, is the key substrate for renin and drives RAS activation. Plasma angiotensinogen levels are markedly elevated in aP2-11βHSD1 transgenic mice, as are angiotensin II and aldosterone (Masuzaki et al. (2003) J. Clinical Invest. 112: 83-90). These forces likely drive the elevated blood pressure observed in aP2-11βHSD1 transgenic mice. Treatment of these mice with low doses of an angiotensin II receptor antagonist abolishes this hypertension (Masuzaki et al. (2003) J. Clinical Invest. 112: 83-90). This data illustrates the importance of local glucocorticoid reactivation in adipose tissue and liver, and suggests that hypertension may be caused or exacerbated by 11βHSD1 activity. Thus, inhibition of 11βHSD1 and reduction in adipose and/or hepatic glucocorticoid levels is predicted to have beneficial effects on hypertension and hypertension-related cardiovascular disorders.

F. Bone Disease

Glucocorticoids can have adverse effects on skeletal tissues. Continued exposure to even moderate glucocorticoid doses can result in osteoporosis (Cannalis (1996) J. Clin. Endocrinol. Metab. 81: 3441-3447) and increased risk for fractures. Experiments in vitro confirm the deleterious effects of glucocorticoids on both bone-resorbing cells (also known as osteoclasts) and bone forming cells (osteoblasts). 11βHSD1 has been shown to be present in cultures of human primary osteoblasts as well as cells from adult bone, likely a mixture of osteoclasts and osteoblasts (Cooper et al. (2000) Bone 27: 375-381), and the 11βBHSD1 inhibitor carbenoxolone has been shown to attenuate the negative effects of glucocorticoids on bone nodule formation (Bellows et al. (1998) Bone 23: 119-125). Thus, inhibition of 11βHSD1 is predicted to decrease the local glucocorticoid concentration within osteoblasts and osteoclasts, producing beneficial effects in various forms of bone disease, including osteoporosis.

Small molecule inhibitors of 11βHSD1 are currently being developed to treat or prevent 11βHSD1-related diseases such as those described above. For example, certain amide-based inhibitors are reported in WO 2004/089470, WO 2004/089896, WO 2004/056745, and WO 2004/065351. Other amide-based inhibitors are reported in US. Pub. Nos. 2005/0282858, 2005/0288317, 2005/0288329, 2005/0288338, and 2006/0004049. Antagonists of 11βHSD1 have also been evaluated in human clinical trials (Kurukulasuriya, et al., (2003) Curr. Med. Chem. 10: 123-53).

In light of the experimental data indicating a role for 11βHSD1 in glucocorticoid-related disorders, metabolic syndrome, hypertension, obesity, insulin resistance, hyperglycemia, hyperlipidemia, type 2 diabetes, atherosclerosis, androgen excess (hirsutism, menstrual irregularity, hyperandrogenism) and polycystic ovary syndrome (PCOS), therapeutic agents aimed at augmentation or suppression of these metabolic pathways, by modulating glucocorticoid signal transduction at the level of 11βHSD1 are desirable.

Furthermore, because the MR binds to aldosterone (its natural ligand) and cortisol with equal affinities, compounds that are designed to interact with the active site of 11βHSD1 (which binds to cortisone/cortisol) may also interact with the MR and act as antagonists. Because the MR is implicated in heart failure, hypertension, and related pathologies including atherosclerosis, arteriosclerosis, coronary artery disease, thrombosis, angina, peripheral vascular disease, vascular wall damage, and stroke, MR antagonists are desirable and may also be useful in treating complex cardiovascular, renal, and inflammatory pathologies including disorders of lipid metabolism including dyslipidemia or hyperlipoproteinaemia, diabetic dyslipidemia, mixed dyslipidemia, hypercholesterolemia, hypertriglyceridemia, as well as those associated with type 1 diabetes, type 2 diabetes, obesity, metabolic syndrome, and insulin resistance, and general aldosterone-related target-organ damage.

As evidenced herein, there is a continuing need for new and improved drugs that target 11βHSD1. The compounds, compositions and methods described herein help meet this and other needs.

SUMMARY OF THE INVENTION

The present invention provides, inter alia, compounds of Formula I:

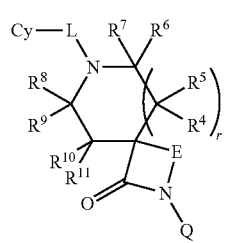

or pharmaceutically acceptable salts or prodrugs thereof, wherein constituent members are defined herein.

The present invention further provides compositions comprising compounds of the invention, or pharmaceutically acceptable salts thereof, and a pharmaceutically acceptable carrier.

The present invention further provides methods of modulating 11βHSD1 by contacting 11βHSD1 with a compound of the invention, or pharmaceutically acceptable salt thereof.

The present invention further provides methods of inhibiting 11βHSD1 by contacting 11βHSD1 with a compound of the invention, or pharmaceutically acceptable salt thereof.

The present invention further provides methods of inhibiting the conversion of cortisone to cortisol in a cell by contacting the cell with a compound of the invention, or pharmaceutically acceptable salt thereof.

The present invention further provides methods of inhibiting the production of cortisol in a cell by contacting the cell with a compound of the invention, or pharmaceutically acceptable salt thereof.

The present invention further provides methods of treating diseases associated with activity or expression of 11βHDS1.

DETAILED DESCRIPTION

The present invention provides, inter alia, compounds of Formula I:

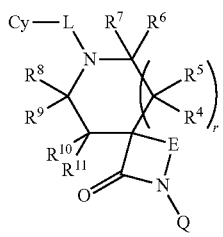

I or pharmaceutically acceptable salt or prodrug thereof, wherein:

Cy is aryl, heteroaryl, cycloalkyl, or heterocycloalkyl, each optionally substituted with 1, 2, 3, 4 or 5 —W—X—Y—Z;

L is absent, $(CR^{12}R^{13})_q$, $(CR^{12}R^{13})_{q1}O(CR^{12}R^{13})_{q2}$, $(CR^{12}R^{13})_{q1}S(CR^{12}R^{13})_{q2}$, $(CR^{12}R^{13})_{q1}SO_2(CR^{12}R^{13})_{q2}$, $(CR^{12}R^{13})_{q1}SO(CR^{12}R^{13})_{q2}$, $(CR^{12}R^{13})_{q1}CO(CR^{12}R^{13})_{q2}$, or $(CR^{12}R^{13})_{q1}CONR^{2a}(CR^{12}R^{13})_{q2}$;

Q is $-(CR^1R^2)_m$-A;

A is cycloalkyl, heterocycloalkyl or heteroaryl, each optionally substituted with 1, 2, 3, 4 or 5

E is $-(CR^{3a}R^{3b})_{n1}-$, $-(CR^{3a}R^{3b})_{n2}CO-$, $-(CR^{3a}R^{3b})_{n2}OCO-$, $-(CR^{3a}R^{3b})_{n2}SO-$, $-(CR^{3a}R^{3b})_{n2}SO_2-$, $-(CR^{3a}R^{3b})_{n2}NR^{3c}-$, $-(CR^{3a}R^{3b})_{n2}CONR^{3c}-$, $-(CR^{3a}R^{3b})_{n2}NR^{3c}CO-$, or a group of formula:

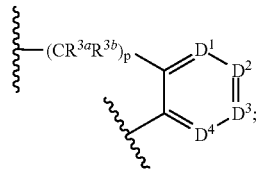

$D^1$, $D^2$, $D^3$ and $D^4$ are independently selected from N and $CR^{15}$;

$R^1$, $R^2$, and $R^{2a}$ are independently selected from H and $C_{1-8}$ alkyl;

$R^{3a}$ and $R^{3b}$ are independently selected from H, halo, $C_{1-4}$ alkyl, $C_{1-4}$ haloalkyl, $C_{2-4}$ alkenyl, and $C_{2-4}$ alkynyl;

$R^{3c}$ is H, $C_{1-4}$ alkyl, $C_{1-4}$ haloalkyl, $C_{2-4}$ alkenyl, $C_{2-4}$ alkynyl, or CO—($C_{1-4}$ alkyl);

$R^4$, $R^5$, $R^6$, $R^7$, $R^8$, $R^9$, $R^{10}$ and $R^{11}$ are independently selected from H, $OC(O)R^{a'}$, $OC(O)OR^{b'}$, $C(O)OR^{b'}$, $OC(O)NR^{c'}R^{d'}$, $NR^{c'}R^{d'}$, $NR^{c'}C(O)R^{a'}$, $NR^{c'}C(O)OR^{b'}$, $S(O)R^{a'}$, $S(O)NR^{c'}R^{d'}$, $S(O)_2R^{a'}$, $S(O)_2NR^{c'}R^{d'}$, $OR^{b'}$, $SR^{b'}$, halo, $C_{1-10}$ alkyl, $C_{1-10}$ haloalkyl, $C_{2-10}$ alkenyl, $C_{2-10}$ alkynyl, aryl, cycloalkyl, heteroaryl, heterocycloalkyl, arylalkyl, heteroarylalkyl, cycloalkylalkyl, and heterocycloalkylalkyl, wherein said $C_{1-10}$ alkyl, $C_{1-10}$ haloalkyl, $C_{2-10}$ alkenyl, $C_{2-10}$ alkynyl, aryl, cycloalkyl, heteroaryl, heterocycloalkyl, arylalkyl, heteroarylalkyl, cycloalkylalkyl, or heterocycloalkylalkyl is optionally substituted by 1, 2, or 3 $R^{14}$;

or $R^4$ and $R^5$ together with the carbon atom to which they are attached form a 3-14 membered cycloalkyl or heterocycloalkyl group which is optionally substituted by $R^{14}$;

or $R^6$ and $R^7$ together with the carbon atom to which they are attached form a 3-14 membered cycloalkyl or heterocycloalkyl group which is optionally substituted by $R^{14}$;

or $R^8$ and $R^9$ together with the carbon atom to which they are attached form a 3-14 membered cycloalkyl or heterocycloalkyl group which is optionally substituted by $R^{14}$;

or $R^{10}$ and $R^{11}$ together with the carbon atom to which they are attached form a 3-14 membered cycloalkyl or heterocycloalkyl group which is optionally substituted by $R^{14}$;

or $R^4$ and $R^6$ together with the carbon atom to which they are attached form a 3-7 membered fused cycloalkyl group or 3-7 membered fused heterocycloalkyl group which is optionally substituted by $R^{14}$;

or $R^6$ and $R^8$ together with the carbon atom to which they are attached form a 3-7 membered fused cycloalkyl group or 3-7 membered fused heterocycloalkyl group which is optionally substituted by $R^{14}$;

or $R^4$ and $R^9$ together form a $C_{1-3}$ alkylene bridge which is optionally substituted by $R^{14}$;

or $R^4$ and $R^{10}$ together form a $C_{1-3}$ alkylene bridge which is optionally substituted by $R^{14}$;

or $R^6$ and $R^{10}$ together form a $C_{1-3}$ alkylene bridge which is optionally substituted by $R^{14}$;

or $R^9$ and $R^{10}$ together form a $C_{1-3}$ alkylene bridge which is optionally substituted by $R^{14}$;

$R^{12}$ and $R^{13}$ are independently selected from H, halo, $C_{1-4}$ alkyl, $C_{1-4}$ haloalkyl, cycloalkyl, heteroaryl, heterocycloalkyl, CN, $NO_2$, $OR^{a'}$, $SR^{a'}$, $C(O)R^{b'}$, $C(O)NR^{c'}R^{d'}C(O)$ $OR^{a'}$, $OC(O)R^{b'}$, $OC(O)NR^{c'}$, $R^{d'}$, $S(O)R^{b'}$, $S(O)NR^{c'}R^{d'}$, $S(O)_2R^{b'}$, and $S(O)_2NR^{c'}R^{d'}$;

$R^{14}$ is halo, $C_{1-4}$ alkyl, $C_{1-4}$ haloalkyl, aryl, cycloalkyl, heteroaryl, heterocycloalkyl, CN, $NO_2$, $OR^{a'}$, $SR^{a'}$, $C(O)R^{b'}$, $C(O)NR^{c'}R^{d'}$, $C(O)OR^{a'}$, $OC(O)R^{b'}$, $OC(O)NR^{c'}R^{d'}$, $NR^{c'}R^{d'}$, $NR^{c'}C(O)R^{d'}$, $NR^{c'}C(O)OR^{a'}$, $S(O)R^{b'}$ $S(O)NR^{c'}R^{d'}$, $S(O)_2R^{b'}$, or $S(O)_2NR^{c'}R^{d'}$;

$R^{15}$ is H, halo, $C_{1-4}$ alkyl, $C_{1-4}$ haloalkyl, aryl, cycloalkyl, heteroaryl, heterocycloalkyl, CN, $NO_2$, $OR^{a''}$, $SR^{a''}$, $C(O)R^{b''}$, $C(O)NR^{c''}R^{d''}$, $C(O)OR^{a''}$, $OC(O)R^{b''}$, $OC(O)NR^{c''}R^{d''}$, $NR^{c''}R^{d''}$, $NR^{c''}C(O)R^{d''}$, $NR^{c''}C(O)OR^{a''}$, $S(O)R^{b''}$, $S(O)NR^{c''}R^{d''}$, $S(O)_2R^{b''}$, or $S(O)_2NR^{c''}R^{d''}$;

W, W' and W" are independently selected from absent, $C_{1-6}$ alkylenyl, $C_{2-6}$ alkenylenyl, $C_{2-6}$ alkynylenyl, O, S, $NR^e$, CO, COO, $CONR^e$, SO, $SO_2$, $SONR^e$, and $NR^eCONR^f$, wherein said $C_{1-6}$ alkylenyl, $C_{2-6}$ alkenylenyl, or $C_{2-6}$ alkynylenyl are each optionally substituted by 1, 2 or 3 substituents independently selected from halo, OH, $C_{1-4}$ alkoxy, $C_{1-4}$ haloalkoxy, amino, $C_{1-4}$ alkylamino, and $C_{2-8}$ dialkylamino;

X, X' and X" are independently selected from absent, $C_{1-6}$ alkylenyl, $C_{2-6}$ alkenylenyl, $C_{2-6}$ alkynylenyl, aryl, cycloalkyl, heteroaryl, and heterocycloalkyl, wherein said $C_{1-6}$ alkylenyl, $C_{2-6}$ alkenylenyl, $C_{2-6}$ alkynylenyl, aryl, cycloalkyl, heteroaryl or heterocycloalkyl is optionally substituted by one or more substituents independently selected from halo, oxo, CN, $NO_2$, OH, $C_{1-4}$ alkoxy, $C_{1-4}$ haloalkoxy, amino, $C_{1-4}$ alkylamino, and $C_{2-8}$ dialkylamino;

Y, Y' and Y" are independently selected from absent, $C_{1-6}$ alkylenyl, $C_{2-6}$ alkenylenyl, $C_{2-6}$ alkynylenyl, O, S, $NR^e$, CO, COO, $CONR^e$, SO, $SO_2$, $SONR^e$, and $NR^eCONR^f$, wherein said $C_{1-6}$ alkylenyl, $C_{2-6}$ alkenylenyl, $C_{2-6}$ alkynylenyl are each optionally substituted by 1, 2 or 3 substituents independently selected from halo, OH, $C_{1-4}$ alkoxy, $C_{1-4}$ haloalkoxy, amino, $C_{1-4}$ alkylamino, and $C_{2-8}$ dialkylamino;

Z, Z' and Z" are independently selected from H, halo, CN, $NO_2$, OH, $C_{1-4}$ alkoxy, $C_{1-4}$ haloalkoxy, amino, $C_{1-4}$ alkylamino, $C_{2-8}$ dialkylamino, $C_{1-6}$ alkyl, $C_{2-6}$ alkenyl, $C_{2-6}$ alkynyl, aryl, cycloalkyl, heteroaryl, and heterocycloalkyl, wherein said $C_{1-6}$ alkyl, $C_{2-6}$ alkenyl, $C_{2-6}$ alkynyl, aryl, cycloalkyl, heteroaryl, or heterocycloalkyl is optionally substituted by 1, 2 or 3 substituents independently selected from halo, oxo, $C_{1-6}$ alkyl, $C_{2-6}$ alkenyl, $C_{2-6}$ alkynyl, $C_{1-4}$ haloalkyl, aryl, cycloalkyl, heteroaryl, heterocycloalkyl, halosulfanyl, CN, $NO_2$, $OR^a R$, $SR^a$, $C(O)R^b$, $C(O)NR^cR^d$, $C(O)OR^a$, $OC(O)R^b$, $OC(O)NR^cR^d$, $NR^cR^d$, $NR^cC(O)R^d$, $NR^cC(O)OR^a NR^eS(O)_2R^b$, $C(=NR^i)NR^cR^d$, $NR^cC(=NR^i) NR^cR^d$, $S(O)R^b$, $S(O)NR^cR^d$, $S(O)_2R^b$, and $S(O)_2NR^cR^d$;

wherein two —W—X—Y—Z attached to the same atom optionally form a 3-20 membered cycloalkyl or heterocycloalkyl group, each optionally substituted by 1, 2 or 3 —W"—X"—Y"—Z";

wherein two —W'—X'—Y'—Z' attached to the same atom optionally form a 3-20 membered cycloalkyl or heterocycloalkyl group, each optionally substituted by 1, 2 or 3 —W"—X"—Y"—Z";

wherein —W—X—Y—Z is other than H;
wherein —W'—X'—Y'—Z' is other than H;
wherein —W"—X"—Y"—Z" is other than H;

$R^a$, $R^{a'}$ and $R^{a''}$ are independently selected from H, $C_{1-6}$ alkyl, $C_{1-6}$ haloalkyl, $C_{2-6}$ alkenyl, $C_{2-6}$ alkynyl, aryl, cycloalkyl, heteroaryl, and heterocycloalkyl, wherein said $C_{1-6}$ alkyl, $C_{1-6}$ haloalkyl, $C_{2-6}$ alkenyl, $C_{2-6}$ alkynyl, aryl, cycloalkyl, heteroaryl, or heterocycloalkyl is optionally substituted with H, OH, amino, halo, $C_{1-6}$ alkyl, $C_{1-6}$ haloalkyl, aryl, arylalkyl, heteroaryl, heteroarylalkyl, cycloalkyl, or heterocycloalkyl;

$R^b$, $R^{b'}$ and $R^{b''}$ are independently selected from H, $C_{1-6}$ alkyl, $C_{1-6}$ haloalkyl, $C_{2-6}$ alkenyl, $C_{2-6}$ alkynyl, aryl, cycloalkyl, heteroaryl, heterocycloalkyl, arylalkyl, heteroarylalkyl, cycloalkylalkyl, and heterocycloalkylalkyl, wherein said $C_{1-6}$ alkyl, $C_{1-6}$ haloalkyl, $C_{2-6}$ alkenyl, $C_{2-6}$ alkynyl, aryl, cycloalkyl, heteroaryl, heterocycloalkyl, arylalkyl, heteroarylalkyl, cycloalkylalkyl or heterocycloalkylalkyl is optionally substituted with H, OH, amino, halo, $C_{1-6}$ alkyl, $C_{1-6}$ haloalkyl, $C_{1-6}$ haloalkyl, aryl, arylalkyl, heteroaryl, heteroarylalkyl, cycloalkyl, or heterocycloalkyl;

$R^c$ and $R^d$ are independently selected from H, $C_{1-10}$ alkyl, $C_{1-6}$ haloalkyl, $C_{2-6}$ alkenyl, $C_{2-6}$ alkynyl, aryl, heteroaryl, cycloalkyl, heterocycloalkyl, arylalkyl, heteroarylalkyl, cycloalkylalkyl, and heterocycloalkylalkyl, wherein said $C_{1-10}$ alkyl, $C_{1-6}$ haloalkyl, $C_{2-6}$ alkenyl, $C_{2-6}$ alkynyl, aryl, heteroaryl, cycloalkyl, heterocycloalkyl, arylalkyl, heteroarylalkyl, cycloalkylalkyl, or heterocycloalkylalkyl is optionally substituted with H, OH, amino, halo, $C_{1-6}$ alkyl, $C_{1-6}$ haloalkyl, Cl-6 haloalkyl, aryl, arylalkyl, heteroaryl, heteroarylalkyl, cycloalkyl, or heterocycloalkyl;

or $R^c$ and $R^d$ together with the N atom to which they are attached form a 4-, 5-, 6- or 7-membered heterocycloalkyl group;

$R^{c'}$ and $R^{d'}$ are independently selected from H, $C_{1-10}$ alkyl, $C_{1-6}$ haloalkyl, $C_{2-6}$ alkenyl, $C_{2-6}$ alkynyl, aryl, heteroaryl, cycloalkyl, heterocycloalkyl, arylalkyl, heteroarylalkyl, cycloalkylalkyl and heterocycloalkylalkyl, wherein said $C_{1-10}$ alkyl, $C_{1-6}$ haloalkyl, $C_{2-6}$ alkenyl, $C_{2-6}$ alkynyl, aryl, heteroaryl, cycloalkyl, heterocycloalkyl, arylalkyl, heteroarylalkyl, cycloalkylalkyl, or heterocycloalkylalkyl is optionally substituted with H, OH, amino, halo, $C_{1-6}$ alkyl, $C_{1-6}$ haloalkyl, $C_{1-6}$ haloalkyl, aryl, arylalkyl, heteroaryl, heteroarylalkyl, cycloalkyl, or heterocycloalkyl;

or $R^{c'}$ and $R^{d'}$ together with the N atom to which they are attached form a 4-, 5-, 6- or 7-membered heterocycloalkyl group;

$R^{c''}$ and $R^{d''}$ are independently selected from H, $C_{1-10}$ alkyl, $C_{1-6}$ haloalkyl, $C_{2-6}$ alkenyl, $C_{2-6}$ alkynyl, aryl, heteroaryl, cycloalkyl, heterocycloalkyl, arylalkyl, heteroarylalkyl, cycloalkylalkyl, and heterocycloalkylalkyl, wherein said $C_{1-10}$ alkyl, $C_{1-6}$ haloalkyl, $C_{2-6}$ alkenyl, $C_{2-6}$ alkynyl, aryl, heteroaryl, cycloalkyl, heterocycloalkyl, arylalkyl, heteroarylalkyl, cycloalkylalkyl, or heterocycloalkylalkyl is optionally substituted with H, OH, amino, halo, $C_{1-6}$ alkyl, $C_{1-6}$ haloalkyl, $C_{1-6}$ haloalkyl, aryl, arylalkyl, heteroaryl, heteroarylalkyl, cycloalkyl, or heterocycloalkyl;

or $R^{c''}$ and $R^{d''}$ together with the N atom to which they are attached form a 4-, 5-, 6- or 7-membered heterocycloalkyl group;

$R^e$ and $R^f$ are independently selected from H, $C_{1-10}$ alkyl, $C_{1-6}$ haloalkyl, $C_{2-6}$ alkenyl, $C_{2-6}$ alkynyl, aryl, heteroaryl, cycloalkyl, heterocycloalkyl, arylalkyl, heteroarylalkyl, cycloalkylalkyl, and heterocycloalkylalkyl, wherein said $C_{1-10}$ alkyl, $C_{1-6}$ haloalkyl, $C_{2-6}$ alkenyl, $C_{2-6}$ alkynyl, aryl, heteroaryl, cycloalkyl, heterocycloalkyl, arylalkyl, heteroarylalkyl, cycloalkylalkyl, or heterocycloalkylalkyl is optionally substituted with H, OH, amino, halo, $C_{1-6}$ alkyl, $C_{1-6}$ haloalkyl, $C_{1-6}$ haloalkyl, aryl, arylalkyl, heteroaryl, heteroarylalkyl, cycloalkyl or heterocycloalkyl;

or $R^e$ and $R^f$ together with the N atom to which they are attached form a 4-, 5-, 6- or 7-membered heterocycloalkyl group;

$R^i$ is H, CN, or $NO_2$;
m is 0, 1, 2 or 3;
n1 is 1, 2, 3 or 4;
n2 is 0, 1, 2, 3 or 4;
p is 0, 1 or 2;
q is 1, 2 or 3;
q1 is 0, 1 or 2;
q2 is 0, 1 or 2; and
r is 1 or 2.

In some embodiments, when Q is other than cycloalkyl substituted by 1, 2, 3, 4 or 5 OH, then L is other than $CH_2$, $CH_2CH_2$, $CH_2CH_2CH_2$, $CH_2CHOH$ or $CH_2CO$.

In some embodiments, when E is $CONR^{3c}$ and m is 1, then A is other than optionally substituted heteroaryl.

In some embodiments, Cy is aryl or heteroaryl, each optionally substituted with 1, 2, 3, 4 or 5 —W—X—Y—Z.

In some embodiments, Cy is aryl or heteroaryl, each optionally substituted with 1, 2, 3, 4 or 5 —W—X—Y—Z wherein W is O or absent, X is absent, and Y is absent.

In some embodiments, Cy is phenyl, naphthyl, pyridyl, pyrimidinyl, triazinyl, furanyl, thiazolyl, pyrazinyl, purinyl, quinazolinyl, quinolinyl, isoquinolinyl, pyrrolo[2,3-d]pyrimidinyl, or 1,3-benzothiazolyl, each optionally substituted with 1, 2, 3, 4 or 5 —W—X—Y—Z.

In some embodiments, Cy is phenyl, naphthyl, pyridyl, pyrimidinyl, triazinyl, furanyl thiazolyl, pyrazinyl, purinyl, quinazolinyl, quinolinyl, isoquinolinyl, pyrrolo[2,3-d]pyrimidinyl, or 1,3-benzothiazolyl, each optionally substituted by 1, 2, 3 or 4 halo, CN, NO$_2$, C$_{1-4}$ alkoxy, heteroaryloxy, C$_{2-6}$ alkynyl, C$_{1-4}$ haloalkoxy, NR$^c$C(O)R$^d$, NR$^c$C(O)OR$^a$, C(O)NR$^c$R$^d$, NR$^c$R$^d$, NR$^e$S(O)$_2$R$^b$, C$_{1-4}$ haloalkyl, C$_{1-6}$ alkyl, heterocycloalkyl, aryl or heteroaryl, wherein each of said C$_{1-6}$ alkyl, aryl or heteroaryl is optionally substituted by 1, 2 or 3 halo, C$_{1-6}$ alkyl, C$_{1-4}$ haloalkyl, CN, NO$_2$, OR$^a$, SR, C(O)NR$^c$R$^d$, NR$^c$C(O)R$^d$ or COOR$^a$.

In some embodiments, Cy is phenyl, pyridyl, pyrimidinyl, pyrazinyl or 1,3-benzothiazolyl, each optionally substituted by 1, 2, 3, 4 or 5 —W—X—Y—Z.

In some embodiments, Cy is phenyl, pyridyl, pyrimidinyl, pyrazinyl or 1,3-benzothiazolyl, each optionally substituted by 1, 2, 3 or 4 halo, CN, NO$_2$, C$_{1-4}$ alkoxy, heteroaryloxy, C$_{2-6}$ alkynyl, C$_{1-4}$ haloalkoxy, NR$^c$C(O)R$^d$, NR$^c$C(O)OR$^a$, C(O)NR$^c$R$^d$, NR$^c$R$^d$, NR$^e$S(O)$_2$R$^b$, C$_{1-4}$ haloalkyl, C$_{1-6}$ alkyl, heterocycloalkyl, aryl or heteroaryl, wherein each of said C$_{1-6}$ alkyl, aryl or heteroaryl is optionally substituted by 1, 2 or 3 halo, C$_{1-6}$ alkyl, C$_{1-4}$ haloalkyl, CN, NO$_2$, OR$^a$, SR$^a$, C(O)NR$^c$R$^d$, NR$^c$C(O)R$^d$ or COOR$^a$.

In some embodiments, Cy is phenyl, pyridyl, pyrimidinyl, pyrazinyl or 1,3-benzothiazolyl, each optionally substituted by 1, 2, 3 or 4 halo, CN, C$_{1-4}$ haloalkyl, C$_{1-6}$ alkyl or aryl, wherein each of said C$_{1-6}$ alkyl or aryl is optionally substituted by 1, 2 or 3 halo, C$_{1-6}$ alkyl, C$_{1-4}$ haloalkyl or CN.

In some embodiments, Cy is cycloalkyl or heterocycloalkyl, each optionally substituted by 1, 2, 3, 4 or 5 —W—X—Y—Z.

In some embodiments, Cy is cycloalkyl or heterocycloalkyl, each optionally substituted by 1, 2, 3, 4 or 5 —W—X—Y—Z wherein W is O or absent, X is absent, and Y is absent.

In some embodiments, Cy is cyclopropyl, cyclobutyl, cyclopentyl, cyclohexyl, cycloheptyl, adamantyl, aziridinyl, azetidinyl, pyrrolidine, piperidinyl, piperizinyl or morpholinyl, each optionally substituted by 1, 2, 3, 4 or 5 —W—X—Y—Z.

In some embodiments, Cy is cyclopropyl, cyclobutyl, cyclopentyl, cyclohexyl, cycloheptyl, adamantyl, aziridinyl, azetidinyl, pyrrolidine, piperidinyl, piperizinyl or morpholinyl, each optionally substituted by 1, 2, 3 or 4 halo, CN, NO$_2$, C$_{1-4}$ alkoxy, heteroaryloxy, C$_{2-6}$ alkynyl, C$_{1-4}$ haloalkoxy, NR$^c$C(O)R$^d$, NR$^c$C(O)OR$^a$, C(O)NR$^c$R$^d$, NR$^c$R$^d$, NR$^e$S(O)$_2$R$^b$, C$_{1-4}$ haloalkyl, C$_{1-6}$ alkyl, heterocycloalkyl, aryl or heteroaryl, wherein each of said C$_{1-6}$ alkyl, aryl or heteroaryl is optionally substituted by 1, 2 or 3 halo, C$_{1-6}$ alkyl, C$_{1-4}$ haloalkyl, CN, NO$_2$, OR$^a$, SR$^a$, C(O)NR$^c$R$^d$, NR$^c$C(O)R$^d$ or COOR$^a$.

In some embodiments, Cy is cyclohexyl or piperidinyl each optionally substituted by 1, 2, 3, 4 or 5 —W—X—Y—Z.

In some embodiments, L is absent.

In some embodiments, L is (CR$^{12}$R$^{13}$)$_{q1}$S(CR$^{12}$R$^{13}$)$_{q2}$, (CR$^{12}$R$^{13}$)$_{q1}$SO$_2$(CR$^{12}$R$^{13}$)$_{q2}$, or (CR$^{12}$R$^{13}$)$_{q1}$SO(CR$^{12}$R$^{13}$)$_{q2}$.

In some embodiments, L is (CR$^{12}$R$^{13}$)$_{q1}$SO$_2$(CR$^{12}$R$^{13}$)$_{q2}$.

In some embodiments, L is S, SO or SO$_2$.

In some embodiments, L is SO$_2$.

In some embodiments, L is CO.

In some embodiments, Q is A (i.e., m is 0).

In some embodiments, Q is —(CR$^1$R$^2$)$_m$-A and m is 1, 2 or 3.

In some embodiments, A is cycloalkyl, heterocycloalkyl or heteroaryl, each optionally substituted by 1, 2, 3, 4 or 5 —W'—X'—Y'—Z', wherein W' is O or absent, X' is absent, and Y' is absent.

In some embodiments, A is cycloalkyl or heterocycloalkyl, each optionally substituted with 1, 2, 3, 4 or 5 —W'—X'—Y'—Z'.

In some embodiments, A is cycloalkyl or heterocycloalkyl, each optionally substituted with 1 or 2 —W'—X'—Y'—Z'.

In some embodiments, A is cycloalkyl or heterocycloalkyl, each optionally substituted by 1, 2, 3, 4 or 5 OH, C$_{1-4}$ alkoxy, CN, C$_{1-4}$ alkyl, O-heteroaryl, —(C$_{1-4}$ alkyl)-OH, —(C$_{1-4}$ alkyl)-CN, COOR$^a$, C(O)NR$^c$R$^d$ or NR$^c$C(O)OR$^a$.

In some embodiments, A is cycloalkyl optionally substituted by 1, 2, 3, 4 or 5 OH, C$_{1-4}$ alkoxy, CN, C$_{1-4}$ alkyl, —O-heteroaryl, —(C$_{1-4}$ alkyl)-OH, —(C$_{1-4}$ alkyl)-CN, COOR$^a$, C(O)NR$^c$R$^d$ or NR$^c$C(O)OR$^a$.

In some embodiments, A is cyclopropyl, cyclobutyl, cyclopentyl, cyclohexyl, cycloheptyl or adamantyl, each optionally substituted by 1, 2, 3, 4 or 5 OH, C$_{1-4}$ alkoxy, CN, C$_{1-4}$ alkyl, —O—heteroaryl, —(C$_{1-4}$ alkyl)-OH, —(C$_{1-4}$ alkyl)-CN, COOR$^a$, C(O)NR$^c$R$^d$ or NR$^c$C(O)OR$^a$.

In some embodiments, A is cyclopentyl or cyclohexyl, each substituted by 1, 2, 3, 4 or 5 OH, C$_{1-4}$ alkoxy, —O-heteroaryl or —(C$_{1-4}$ alkyl)-OH.

In some embodiments, A is cyclohexyl substituted by 1, 2, 3, 4 or 5 OH.

In some embodiments, A is cyclohexyl substituted at the 4-position by at least one —W'—X'—Y'—Z'.

In some embodiments, A is cyclohexyl substituted at the 4-position by at least one OH, CN, or —O—X'—Y'—Z'.

In some embodiments, A is cyclohexyl substituted at the 4-position by 1 or 2 OH.

In some embodiments, A is cyclohexyl substituted at the 4-position by 1 OH.

In some embodiments, A is cycloalkyl or heterocycloalkyl, each substituted with at least two —W'—X'—Y'—Z', wherein two of said at least two —W'—X'—Y'—Z' are attached to the same atom and together with the atom to which they are attached form a 3-20 membered cycloalkyl or heterocycloalkyl group, each optionally substituted by 1, 2 or 3 —W"—X"—Y"—Z".

In some embodiments, A is heteroaryl optionally substituted with 1, 2, 3, 4 or 5 —W'—X'—Y'—Z'.

In some embodiments, A is pyridyl, pyrimidinyl, triazinyl, furanyl thiazolyl, pyrazinyl, purinyl, quinazolinyl, quinolinyl, isoquinolinyl, pyrrolo[2,3-d]pyrimidinyl, or 1,3-benzothiazolyl, each optionally substituted by 1, 2, 3 or 4 OR$^a$, SR$^a$, halo, CN, NO$_2$, C$_{1-4}$ alkoxy, heteroaryloxy, C$_{2-6}$ alkynyl, C$_{1-4}$ haloalkoxy, NR$^c$C(O)R$^d$, NR$^c$C(O)OR$^a$, C(O)NR$^c$R$^d$, NR$^c$R$^d$, NR$^e$S(O)$_2$R$^b$, C$_{1-4}$haloalkyl, C$_{1-6}$ alkyl, heterocycloalkyl, aryl or heteroaryl, wherein each of said C$_{1-6}$ alkyl, aryl or heteroaryl is optionally substituted by 1, 2 or 3 halo, C$_{1-6}$ alkyl, C$_{1-4}$ haloalkyl, CN, NO$_2$, OR$^a$, SR$^a$, C(O)NR$^c$R$^d$, NR$^c$C(O)R$^d$ or COOR$^a$.

In some embodiments, E is methylene, ethylene, or propylene.

In some embodiments, E is ethylene.

In some embodiments, E is a group of formula:

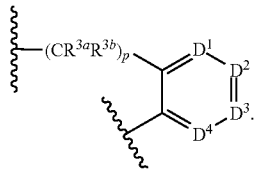

In some embodiments, $D^1$, $D^2$, $D^3$ and $D^4$ are each $CR^{15}$.

In some embodiments, one or two or $D^1$, $D^2$, $D^3$ and $D^4$ is N.

In some embodiments, $R^4$, $R^5$, $R^6$, $R^7$, $R^8$, $R^9$, $R^{10}$ and $R^{11}$ are independently selected from H, $OC(O)R^a$, $OC(O)OR^{b'}$, $C(O)OR^{b'}$, $OC(O)NR^cR^{d'}$, $NR^cR^{d'}$, $NR^cC(O)R^a$, $NR^cC(O)OR^{b'}$, $S(O)R^{a'}$, $S(O)NR^cR^{d'}$, $S(O)_2R^{a'}$, $S(O)_2NR^cR^{d'}$, $OR^{b'}$, $SR^{b'}$, halo, $C_{1-10}$ alkyl, $C_{1-10}$ haloalkyl, $C_{2-10}$ alkenyl, $C_{2-10}$ alkynyl, aryl, cycloalkyl, heteroaryl, heterocycloalkyl, arylalkyl, heteroarylalkyl, cycloalkylalkyl, and heterocycloalkylalkyl, wherein said $C_{1-10}$ alkyl, $C_{1-10}$ haloalkyl, $C_{2-10}$ alkenyl, $C_{2-10}$ alkynyl, aryl, cycloalkyl, heteroaryl, heterocycloalkyl, arylalkyl, heteroarylalkyl, cycloalkylalkyl or heterocycloalkylalkyl is optionally substituted by $R^{14}$.

In some embodiments, $R^4$, $R^5$, $R^6$, $R^7$, $R^8$, $R^9$, $R^{10}$ and $R^{11}$ are each, independently, H, $OC(O)R^{a'}$, $OC(O)OR^{b'}$, $C(O)OR^{b'}$, $OC(O)NR^cR^{d'}$, $NR^cR^{d'}$, $NR^cC(O)R^{a'}$, $NR^cC(O)OR^{b'}$, $S(O)R^{a'}$, $S(O)NR^cR^{d'}$, $S(O)_2R^{a'}$, $S(O)_2NR^cR^{d'}$, $OR^b$, $SR^{b'}$, $C_{1-10}$alkyl, $C_{1-10}$haloalkyl, $C_{2-10}$ alkenyl, $C_{2-10}$ alkynyl, aryl, cycloalkyl, heteroaryl, heterocycloalkyl, arylalkyl, heteroarylalkyl, cycloalkylalkyl or heterocycloalkylalkyl.

In some embodiments, $R^4$, $R^5$, $R^6$, $R^7$, $R^8$, $R^9$, $R^{10}$ and $R^{11}$ are each, independently, H, $C_{1-10}$ alkyl or $C_{1-10}$ haloalkyl.

In some embodiments, $R^4$, $R^5$, $R^6$, $R^7$, $R^8$, $R^9$, $R^{10}$ and $R^{11}$ are each H.

In some embodiments, $R^{3a}$ and $R^{3b}$ are each H.

In some embodiments, $R^{2a}$ is H.

In some embodiments, r is 1.

In some embodiments, r is 2.

In some embodiments, the sum of q1 and q2 is 0, 1 or 2.

In some embodiments, the sum of q1 and q2 is 0.

In some embodiments, the sum of q1 and q2 is 1.

In some embodiments, $R^{12}$ and $R^{13}$ are each H.

In some embodiments, at least one of $R^1$ and $R^2$ is $C_{1-4}$ alkyl.

In some embodiments, n1 is 2.

In some embodiments, each —W—X—Y—Z is, independently, —$NR^eC(O)O$—Z, —C(O)O—Z, —$NR^eC(O)$—Z, —CO—Z, —SO—Z, —$SO_2$—Z, —$SONR^e$—Z, —$NR^e$-$CONR^f$—Z, halo, CN, $NO_2$, OH, $C_{1-4}$ alkoxy, $C_{1-4}$ haloalkoxy, amino, $C_{1-4}$ alkylamino, $C_{2-8}$ dialkylamino, $C_{1-6}$ alkyl, $C_{2-6}$ alkenyl, $C_{2-6}$ alkynyl, aryl, cycloalkyl, heteroaryl or heterocycloalkyl, wherein said $C_{1-6}$ alkyl, $C_{2-6}$ alkenyl, $C_{2-6}$ alkynyl, aryl, cycloalkyl, heteroaryl or heterocycloalkyl is optionally substituted by 1, 2 or 3 halo, oxo, $C_{1-6}$ alkyl, $C_{2-6}$ alkenyl, $C_{2-6}$ alkynyl, $C_{1-4}$ haloalkyl, aryl, cycloalkyl, heteroaryl, heterocycloalkyl, CN, $NO_2$, $OR^a$, $SR^a$, $C(O)R^b$, $C(O)NR^cR^d$, $C(O)OR^a$, $OC(O)R^b$, $OC(O)NR^cR^d$, $NR^cR^d$, $NR^cC(O)R^d$, $NR^cC(O)OR^a$, $S(O)R^b$, $S(O)NR^cR^d$, $S(O)_2R^b$, or $S(O)_2NR^cR^d$.

In some embodiments, each —W—X—Y—Z is, independently, —$NHC(O)O$—$C_{1-4}$ alkyl, —$NHC(O)O$—$C_{1-4}$ alkynyl, —$C(O)O$—$C_{1-4}$ alkyl, —$NHC(O)$—$C_{1-4}$ alkyl, —$NHC(O)$—$C_{3-9}$cycloalkyl, halo, CN, $NO_2$, OH, $C_1$-4 alkoxy, $C_{1-4}$ haloalkoxy, amino, $C_{1-4}$ alkylamino, $C_{2-8}$ dialkylamino, $C_{1-6}$ alkyl, $C_{2-6}$ alkenyl, $C_{2-6}$ alkynyl, aryl, cycloalkyl, heteroaryl or heterocycloalkyl, wherein said $C_{1-6}$ alkyl, $C_{2-6}$ alkenyl, $C_{2-6}$ alkynyl, aryl, cycloalkyl, heteroaryl or heterocycloalkyl is optionally substituted by 1, 2 or 3 halo, oxo, $C_{1-6}$ alkyl, $C_{2-6}$ alkenyl, $C_{2-6}$ alkynyl, $C_{1-4}$haloalkyl, aryl, cycloalkyl, heteroaryl, heterocycloalkyl, CN, $NO_2$, $OR^a$, $SR^a$, $C(O)R^b$, $C(O)NR^cR^d$, $C(O)OR^a$, $OC(O)R^b$, $OC(O)NR^cR^d$, $NR^cR^d$, $NR^cC(O)R^d$, $NR^cC(O)OR^a$, $S(O)R^b$, $S(O)NR^cR^d$, $S(O)_2R^b$, or $S(O)_2NR^cR^d$.

In some embodiments, each —W—X—Y—Z is, independently, halo, CN, $C_{1-6}$ alkyl, $C_{1-6}$ haloalkyl, $C_{1-6}$ alkoxy, —$NR^eC(O)O$—Z, —C(O)O—Z, —$NR^eC(O)$—Z or aryl, wherein said aryl is optionally substituted by 1, 2 or 3 halo or $C_{1-4}$ haloalkyl.

In some embodiments, each —W—X—Y—Z is, independently, halo, CN, $C_{1-4}$ alkyl, $C_{1-4}$ haloalkyl, $C_{1-4}$ alkoxy, —$NHC(O)O$—($C_{1-4}$ alkyl), —$NHC(O)O$—($C_{1-4}$ alkynyl), —$C(O)O$—($C_{1-4}$ alkyl), —$NHC(O)$—($C_{1-4}$ alkyl), —NHC(O)—($C_{3-9}$ cycloalkyl) or phenyl, wherein said phenyl is optionally substituted by 1, 2 or 3 halo or $C_{1-4}$ haloalkyl.

In some embodiments, each —W—X—Y—Z is, independently, halo, CN, $NO_2$, $C_{1-4}$ alkoxy, heteroaryloxy, $C_{2-6}$ alkynyl, $C_{1-4}$ haloalkoxy, $NR^cC(O)R^d$, $NR^cC(O)OR^a$, $C(O)NR^cR^d$, $NR^cR^d$, $NR^eS(O)_2R^b$, $C_{1-4}$ haloalkyl, $C_{1-6}$ alkyl, heterocycloalkyl, aryl or heteroaryl, wherein each of said $C_{1-6}$ alkyl, aryl or heteroaryl is optionally substituted by 1, 2 or 3 halo, $C_{1-6}$ alkyl, $C_{1-4}$ haloalkyl, CN, $NO_2$, OR, $SR^a$, $C(O)NR^cR^d$, $NR^cC(O)R^d$ or $COOR^a$.

In some embodiments, each —W—X—Y—Z is, independently, halo, CN, $NO_2$, $C_{1-4}$ alkoxy, pyridin-2-yloxy, pyridin-3-yloxy, pyridin-4-yloxy, $C_{2-6}$ alkynyl, $C_{1-4}$ haloalkoxy, $NR^c$-$C(O)R^d$, $NR^cC(O)OR^a$, $C(O)NR^cR^d$, $NR^cR^d$, $NR^eS(O)_2R^b$, $C_{1-4}$ haloalkyl, $C_{1-6}$ alkyl, phenyl, pyridyl, pyrimidinyl, isoxazolyl, pyrazolyl, 1,2,3,6-tetrahydro-pyridinyl, 2-oxo-(2H)-pyridinyl, 2-oxo-[1,3]oxazolidinyl, 2-oxo-pyrrolidinyl, pyrrolidinyl, 2-oxopiperidinyl, or 2-oxo-[1,3]oxazinanyl, wherein each of said $C_{1-6}$ alkyl, phenyl, pyridyl, pyrimidinyl, isoxazolyl, pyrazolyl, 1,2,3,6-tetrahydro-pyridinyl, 2-oxo-(2H)-pyridinyl, 2-oxo-[1,3]oxazolidinyl, 2-oxo-pyrrolidinyl, pyrrolidinyl, 2-oxopiperidinyl, or 2-oxo-[1,3]oxazinanyl is optionally substituted by 1, 2 or 3 halo, $C_{1-6}$ alkyl, $C_{1-4}$ haloalkyl, CN, $NO_2$, $OR^a$, $SR^a$, $C(O)NR^cR^d$, $NR^cC(O)R^d$ or $COOR^a$.

In some embodiments, each —W—X—Y—Z is, independently, aryl or heteroaryl, wherein each of said aryl or heteroaryl is optionally substituted by 1, 2 or 3 halo, CN, $C_{1-4}$ alkyl, phenyl, pyridyl, $C_{1-4}$ alkoxy, or $C_{1-4}$ haloalkyl.

In some embodiments, each —W—X—Y—Z is, independently, phenyl, pyridyl or quinolinyl, wherein each of said phenyl, pyridyl, quinolinyl is optionally substituted by 1, 2 or 3 halo, CN, $C_{1-4}$ alkyl, phenyl, $C_{1-4}$ alkoxy, or $C_{1-4}$ haloalkyl.

In some embodiments, each —W'—X'—Y'—Z' is, independently, OH, CN, halo, $C_{1-6}$ alkyl, C, 6 haloalkyl, aryl, heteroaryl, cycloalkyl, heterocycloalkyl, —O—Z',—C(O)—Z' or —C(O)O—Z', wherein said $C_{1-6}$ alkyl, aryl, heteroaryl, cycloalkyl, or heterocycloalkyl are each optionally substituted by 1, 2 or 3 halo, oxo, $C_{1-6}$ alkyl, $C_{2-6}$ alkenyl, $C_{2-6}$ alkynyl, $C_{1-4}$ haloalkyl, aryl, cycloalkyl, heteroaryl, heterocycloalkyl, CN, $NO_2$, $OR^a$, $SR^a$, $C(O)R^b$, $C(O)NR^cR^d$, $C(O)OR^a$, $OC(O)R^b$, $OC(O)NR^cR^d$, $NR^cR^d$, $NR^cC(O)R^d$, $NR^cC(O)OR^a$, $S(O)R^b$, $S(O)NR^cR^d$, $S(O)_2R^b$, or $S(O)_2NR^cR^d$.

In some embodiments, each —W'—X'—Y'—Z' is, independently, OH, $C_{1-4}$ alkoxy, CN, $C_{1-4}$ alkyl, —O-heteroaryl, —($C_{1-4}$ alkyl)-CN, COOR$^a$, C(O)NR$^c$R$^d$ or NR$^c$C(O)OR$^a$.

In some embodiments, each —W'—X'—Y'—Z' is, independently, halo, $C_{1-4}$ alkyl, CN, NR$^c$C(O)R$^d$ or NR$^e$S(O)$_2$R$^b$.

In some embodiments, each —W'—X'—Y'—Z' is, independently, OH, CN, halo, $C_{1-6}$ alkyl, —O-heteroaryl, or C(O)O—Z'.

In some embodiments, each —W'—X'—Y'—Z' is, independently, OH, CN, halo, $C_{1-6}$ alkyl, —O-heteroaryl, or —C(O)O—$C_{1-4}$ alkyl.

In some embodiments, each —W"—X"—Y"—Z" is halo, CN, NO$_2$, OH, $C_{1-4}$ alkoxy, $C_{1-4}$ haloalkoxy, amino, $C_{1-4}$ alkylamino, $C_{2-8}$ dialkylamino, NR$^e$S(O)$_2$R$^b$, $C_{1-6}$ alkyl, $C_{2-6}$ alkenyl, $C_{2-6}$ alkynyl, aryl, cycloalkyl, heteroaryl or heterocycloalkyl, wherein said $C_{1-6}$ alkyl, $C_{2-6}$ alkenyl, $C_{2-6}$ alkynyl, aryl, cycloalkyl, heteroaryl or heterocycloalkyl is optionally substituted by 1, 2 or 3 halo, oxo, $C_{1-6}$ alkyl, $C_{2-6}$ alkenyl, $C_{2-6}$ alkynyl, $C_{1-4}$ haloalkyl, aryl, cycloalkyl, heteroaryl, heterocycloalkyl, CN, NO$_2$, OR$^a$, SR$^a$, C(O)R$^b$, C(O)NR$^c$R$^d$, C(O)OR$^a$, OC(O)R$^b$, OC(O)NR$^c$R$^d$, NR$^c$R$^d$, NR$^c$C(O)R$^d$, NR$^c$C(O)OR$^a$, NR$^e$S(O)$_2$R$^b$, S(O)R$^b$, S(O)NR$^c$R$^d$, S(O)$_2$R$^b$, or S(O)$_2$NR$^c$R$^d$.

In some embodiments, each —W"—X"—Y"—Z" is halo, CN, NO$_2$, OH, $C_{1-4}$ alkoxy, $C_{1-4}$ haloalkoxy, amino, $C_{1-4}$ alkylamino, $C_{2-8}$ dialkylamino, $C_{1-6}$ alkyl, $C_{2-6}$ alkenyl, $C_{2-6}$ alkynyl, aryl, cycloalkyl, heteroaryl or heterocycloalkyl, wherein said $C_{1-6}$alkyl, $C_{2-6}$ alkenyl, $C_{2-6}$ alkynyl, aryl, cycloalkyl, heteroaryl or heterocycloalkyl is optionally substituted by 1, 2 or 3 halo, oxo, $C_{1-6}$ alkyl, $C_{2-6}$ alkenyl, $C_{2-6}$ alkynyl, $C_{1-4}$ haloalkyl, aryl, cycloalkyl, heteroaryl, heterocycloalkyl, CN, NO$_2$, OR$^a$, SR$^a$, C(O)R$^b$, C(O)NR$^c$R$^d$, C(O)OR$^a$, OC(O)R$^b$, OC(O)NR$^c$R$^d$, NR$^c$R$^d$, NR$^c$C(O)R$^d$, NR$^c$C(O)OR$^a$, S(O)R$^b$, S(O)NR$^c$R$^d$, S(O)$_2$R$^b$, or S(O)$_2$NR$^c$R$^d$.

In some embodiments, each —W"—X"—Y"—Z" is halo, CN, NO$_2$, OH, $C_{1-4}$ alkoxy, $C_{1-4}$ haloalkoxy, amino, $C_{1-4}$ alkylamino, $C_{2-8}$ dialkylamino, $C_{1-6}$ alkyl, $C_{2-6}$ alkenyl, $C_{2-6}$ alkynyl, aryl, cycloalkyl, heteroaryl or heterocycloalkyl.

In some embodiments, Z, Z' and Z" are independently selected from H, halo, CN, NO$_2$, OH, $C_{1-4}$ alkoxy, $C_{1-4}$ haloalkoxy, amino, $C_{1-4}$ alkylamino, $C_{2-8}$ dialkylamino, $C_{1-6}$ alkyl, $C_{2-6}$ alkenyl, $C_{2-6}$ alkynyl, aryl, cycloalkyl, heteroaryl, and heterocycloalkyl, wherein said $C_{1-6}$ alkyl, $C_{2-6}$ alkenyl, $C_{2-6}$ alkynyl, aryl, cycloalkyl, heteroaryl, or heterocycloalkyl is optionally substituted by 1, 2 or 3 halo, oxo, $C_{1-6}$ alkyl, $C_{2-6}$ alkenyl, $C_{2-6}$ alkynyl, $C_{1-4}$ haloalkyl, aryl, cycloalkyl, heteroaryl, heterocycloalkyl, CN, NO$_2$, OR$^a$, SR$^a$, C(O)R$^b$, C(O)NR$^c$R$^d$, C(O)OR$^a$, OC(O)R$^b$, OC(O)NR$^c$R$^d$, NR$^c$R$^d$, NR$^c$C(O)R$^d$, NR$^c$C(O)OR$^a$, NR$^e$S(O)$_2$R$^b$, S(O)R$^b$, S(O)NR$^c$R$^d$, S(O)$_2$R$^b$, or S(O)$_2$NR$^c$R$^d$.

In some embodiments, compounds of the invention have Formula II:

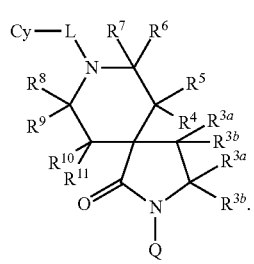

In some embodiments, compounds of the invention have Formula III:

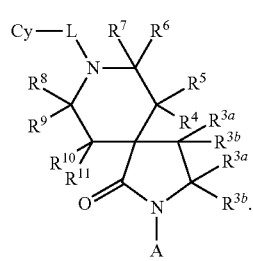

In some embodiments, compounds of the invention have Formula III wherein L is absent, SO$_2$ or CO$_2$.

In some embodiments, compounds of the invention have Formula III wherein L is absent; and R$^4$, R$^5$, R$^6$, R$^7$, R$^8$, R$^9$, R$^{10}$, R$^{11}$, R$^{3a}$ and R$^{3b}$ are each, independently, H, $C_{1-4}$ alkyl or $C_{1-4}$ haloalkyl. In some further embodiments, R$^4$, R$^5$, R$^6$, R$^7$, R$^8$, R$^9$, R$^{10}$, R$^{11}$, R$^{3a}$ and R$^{3b}$ are each, independently H. In yet further embodiments, A is cyclohexyl substituted by 1 or 2 OH.

In some embodiments, compounds of the invention have Formula IV:

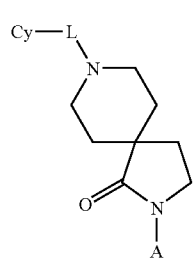

In some embodiments, compounds of the invention have Formula IV wherein L is absent, SO$_2$ or CO$_2$. In some further embodiments, A is cyclohexyl substituted by 1 or 2 OH. In yet further embodiments, L is absent and Cy is aryl or heteroaryl, each optionally substituted with 1, 2, 3, 4 or 5 —W—X—Y—Z.

At various places in the present specification, substituents of compounds of the invention are disclosed in groups or in ranges. It is specifically intended that the invention include each and every individual subcombination of the members of such groups and ranges. For example, the term "$C_{1-6}$ alkyl" is specifically intended to individually disclose methyl, ethyl, $C_3$ alkyl, $C_4$ alkyl $C_5$ alkyl, and $C_6$ alkyl.

It is further appreciated that certain features of the invention, which are, for clarity, described in the context of separate embodiments, can also be provided in combination in a single embodiment. Conversely, various features of the invention which are, for brevity, described in the context of a single embodiment, can also be provided separately or in any suitable subcombination.

At various places in the present specification, linking substituents are described. It is specifically intended that each linking substituent include both the forward and backward forms of the linking substituent. For example, —NR(CR'R")$_n$— includes both NR(CRR)$_n$ and —(CR'R")$_n$NR—. Where the structure clearly requires a linking group, the Markush variables listed for that group are understood to be linking groups. For example, if the structure requires a linking group (e.g., X of Formula I) and the Markush group definition for that variable lists "alkyl," then it is understood that the "alkyl" represents a linking alkylene group.

The term "n-membered" where n is an integer typically describes the number of ring-forming atoms in a moiety where the number of ring-forming atoms is n. For example, piperidinyl is an example of a 6-membered heterocycloalkyl ring and 1,2,3,4-tetrahydro-naphthalene is an example of a 10-membered cycloalkyl group.

As used herein, the term "alkyl" refers to a saturated hydrocarbon group which is straight-chained or branched. Example alkyl groups include methyl (Me), ethyl (Et), propyl (e.g., n-propyl and isopropyl), butyl (e.g., n-butyl, isobutyl, t-butyl), pentyl (e.g., n-pentyl, isopentyl, neopentyl), and the like. An alkyl group can contain from 1 to about 20, from 2 to about 20, from 1 to about 10, from 1 to about 8, from 1 to about 6, from 1 to about 4, or from 1 to about 3 carbon atoms. The term "alkylenyl" refers to a divalent alkyl linking group.

As used herein, "alkenyl" refers to an alkyl group having one or more carbon-carbon double bonds. Example alkenyl groups include ethenyl, propenyl, cyclohexenyl, and the like. The term "alkenylenyl" refers to a divalent linking alkenyl group.

As used herein, "alkynyl" refers to an alkyl group having one or more carbon-carbon triple bonds. Example alkynyl groups include ethynyl, propynyl, and the like. The term "alkynylenyl" refers to a divalent linking alkynyl group.

As used herein, "haloalkyl" refers to an alkyl group having one or more halogen substituents. Example haloalkyl groups include $CF_3$, $C_2F_5$, $CHF_2$, $CCl_3$, $CHCl_2$, $C_2Cl_5$, and the like.

As used herein, "aryl" refers to monocyclic or polycyclic (e.g., having 2, 3 or 4 fused rings) aromatic hydrocarbons such as, for example, phenyl, naphthyl, anthracenyl, phenanthrenyl, indanyl, indenyl, and the like. In some embodiments, aryl groups have from 6 to about 20 carbon atoms.

As used herein, "cycloalkyl" refers to non-aromatic cyclic hydrocarbons including cyclized alkyl, alkenyl, and alkynyl groups. Cycloalkyl groups can include mono- or polycyclic (e.g., having 2, 3 or 4 fused rings) groups as well as spirocycles. Ring-forming carbon atoms of a cycloalkyl group can be optionally substituted by oxo or sulfido. Example cycloalkyl groups include cyclopropyl, cyclobutyl, cyclopentyl, cyclohexyl, cycloheptyl, cyclopentenyl, cyclohexenyl, cyclohexadienyl, cycloheptatrienyl, norbornyl, norpinyl, norcarnyl, adamantyl, and the like. Also included in the definition of cycloalkyl are moieties that have one or more aromatic rings fused (i.e., having a bond in common with) to the cycloalkyl ring, for example, benzo or thienyl derivatives of cyclopentane, cyclohexane, and the like.

As used herein, "heteroaryl" refers to an aromatic heterocycle having at least one heteroatom ring member such as sulfur, oxygen, or nitrogen. Heteroaryl groups include monocyclic and polycyclic (e.g., having 2, 3 or 4 fused rings) systems. Examples of heteroaryl groups include without limitation, pyridyl, pyrimidinyl, pyrazinyl, pyridazinyl, triazinyl, furyl, quinolyl, isoquinolyl, thienyl, imidazolyl, thiazolyl, indolyl, pyrryl, oxazolyl, benzofuryl, benzothienyl, benzthiazolyl, isoxazolyl, pyrazolyl, triazolyl, tetrazolyl, indazolyl, 1,2,4-thiadiazolyl, isothiazolyl, benzothienyl, purinyl, carbazolyl, benzimidazolyl, indolinyl, and the like. In some embodiments, the heteroaryl group has from 1 to about 20 carbon atoms, and in further embodiments from about 3 to about 20 carbon atoms. In some embodiments, the heteroaryl group contains 3 to about 14, 4 to about 14, 3 to about 7, or 5 to 6 ring-forming atoms. In some embodiments, the heteroaryl group has 1 to about 4, 1 to about 3, or 1 to 2 heteroatoms.

As used herein, "heterocycloalkyl" refers to non-aromatic heterocycles including cyclized alkyl, alkenyl, and alkynyl groups where one or more of the ring-forming carbon atoms is replaced by a heteroatom such as an O, N, or S atom. Heterocycloalkyl groups include monocyclic and polycyclic (e.g., having 2, 3 or 4 fused rings) systems as well as spirocycles. Example "heterocycloalkyl" groups include morpholino, thiomorpholino, piperazinyl, tetrahydrofuranyl, tetrahydrothienyl, 2,3-dihydrobenzofuryl, 1,3-benzodioxole, benzo-1,4-dioxane, piperidinyl, pyrrolidinyl, isoxazolidinyl, isothiazolidinyl, pyrazolidinyl, oxazolidinyl, thiazolidinyl, imidazolidinyl, and the like. Ring-forming carbon atoms and heteroatoms of a heterocycloalkyl group can be optionally substituted by oxo or sulfido. Also included in the definition of heterocycloalkyl are moieties that have one or more aromatic rings fused (i.e., having a bond in common with) to the nonaromatic heterocyclic ring, for example phthalimidyl, naphthalimidyl, and benzo derivatives of heterocycles. In some embodiments, the heterocycloalkyl group has from 1 to about 20 carbon atoms, and in further embodiments from about 3 to about 20 carbon atoms. In some embodiments, the heterocycloalkyl group contains 3 to about 14, 4 to about 14, 3 to about 7, or 5 to 6 ring-forming atoms. In some embodiments, the heterocycloalkyl group has 1 to about 4, 1 to about 3, or 1 to 2 heteroatoms. In some embodiments, the heterocycloalkyl group contains 0 to 3 double or triple bonds. In some embodiments, the heterocycloalkyl group contains 0 to 2 double or triple bonds.

As used herein, "halo" or "halogen" includes fluoro, chloro, bromo, and iodo.

As used herein, "alkoxy" refers to an —O-alkyl group. Example alkoxy groups include methoxy, ethoxy, propoxy (e.g., n-propoxy and isopropoxy), t-butoxy, and the like.

As used here, "haloalkoxy" refers to an —O-haloalkyl group. An example haloalkoxy group is $OCF_3$.

As used herein, "heteroaryloxy" refers to —O-heteroaryl. An example heteroaryloxy is pyridin-2-yloxy [i.e., —O-(pyridin-2-yl)].

As used herein, "arylalkyl" refers to alkyl substituted by aryl and "cycloalkylalkyl" refers to alkyl substituted by cycloalkyl. An example arylalkyl group is benzyl.

As used herein, "heteroarylalkyl" refers to alkyl substituted by heteroaryl and "heterocycloalkylalkyl" refers to alkyl substituted by heterocycloalkyl.

As used herein, "halosulfanyl" refers to a sulfur group having one or more halogen substituents. Example halosulfanyl groups include pentahalosulfanyl groups such as $SF_5$.

As used herein, "amino" refers to $NH_2$.

As used herein, "alkylamino" refers to an amino group substituted by an alkyl group.

As used herein, "dialkylamino" refers to an amino group substituted by two alkyl groups.

The compounds described herein can be asymmetric (e.g., having one or more stereocenters). All stereoisomers, such as enantiomers and diastereomers, are intended unless otherwise indicated. Compounds of the present invention that contain asymmetrically substituted carbon atoms can be isolated in optically active or racemic forms. Methods on how to prepare optically active forms from optically active starting materials are known in the art, such as by resolution of racemic mixtures or by stereoselective synthesis. Many geometric isomers of olefins, C=N double bonds, and the like can also be present in the compounds described herein, and all such stable isomers are contemplated in the present invention. Cis and trans geometric isomers of the compounds of the present invention are described and may be isolated as a mixture of isomers or as separated isomeric forms.

Resolution of racemic mixtures of compounds can be carried out by any of numerous methods known in the art. An example method includes fractional recrystallization using a chiral resolving acid which is an optically active, salt-forming organic acid. Suitable resolving agents for fractional recrystallization methods are, for example, optically active acids, such as the D and L forms of tartaric acid, diacetyltartaric acid, dibenzoyltartaric acid, mandelic acid, malic acid, lactic acid or the various optically active camphorsulfonic acids such as β-camphorsulfonic acid. Other resolving agents suitable for fractional crystallization methods include stereoisomerically pure forms of x-methylbenzylamine (e.g., S and R forms, or diastereomerically pure forms), 2-phenylglycinol, norephedrine, ephedrine, N-methylephedrine, cyclohexylethylamine, 1,2-diaminocyclohexane, and the like.

Resolution of racemic mixtures can also be carried out by elution on a column packed with an optically active resolving agent (e.g., dinitrobenzoylphenylglycine). Suitable elution solvent composition can be determined by one skilled in the art.

Compounds of the invention also include all tautomeric forms. Tautomeric forms result from the swapping of a single bond with an adjacent double bond together with the concomitant migration of a proton. Tautomeric forms include prototropic tautomers which are isomeric protonation states having the same empirical formula and total charge. Example prototropic tautomers include ketone-enol pairs, amide-imidic acid pairs, lactam-lactim pairs, amide-imidic acid pairs, enamine-imine pairs, and annular forms where a proton can occupy two or more positions of a heterocyclic system, for example, 1H- and 3H-imidazole, 1H-, 2H- and 4H-1,2,4-triazole, 1H- and 2H-isoindole, and 1H- and 2H-pyrazole. Tautomeric forms can be in equilibrium or sterically locked into one form by appropriate substitution.

Compounds of the invention further include hydrates and solvates, as well as anhydrous and non-solvated forms.

Compounds of the invention can also include all isotopes of atoms occurring in the intermediates or final compounds. Isotopes include those atoms having the same atomic number but different mass numbers. For example, isotopes of hydrogen include tritium and deuterium.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The present invention also includes pharmaceutically acceptable salts of the compounds described herein. As used herein, "pharmaceutically acceptable salts" refers to derivatives of the disclosed compounds wherein the parent compound is modified by converting an existing acid or base moiety to its salt form. Examples of pharmaceutically acceptable salts include, but are not limited to, mineral or organic acid salts of basic residues such as amines; alkali or organic salts of acidic residues such as carboxylic acids; and the like. The pharmaceutically acceptable salts of the present invention include the conventional non-toxic salts of the parent compound formed, for example, from non-toxic inorganic or organic acids. The pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in Remington's Pharmaceutical Sciences, 17th ed., Mack Publishing Company, Easton, Pa., 1985, p. 1418 and Journal of Pharmaceutical Science, 66, 2 (1977), each of which is incorporated herein by reference in its entirety.

The present invention also includes prodrugs of the compounds described herein. As used herein, "prodrugs" refer to any covalently bonded carriers which release the active parent drug when administered to a mammalian subject. Prodrugs can be prepared by modifying functional groups present in the compounds in such a way that the modifications are cleaved, either in routine manipulation or in vivo, to the parent compounds. Prodrugs include compounds wherein hydroxyl, amino, sulfhydryl, or carboxyl groups are bonded to any group that, when administered to a mammalian subject, cleaves to form a free hydroxyl, amino, sulfhydryl, or carboxyl group respectively. Examples of prodrugs include, but are not limited to, acetate, formate and benzoate derivatives of alcohol and amine functional groups in the compounds of the invention. Preparation and use of prodrugs is discussed in T. Higuchi and V. Stella, "Pro-drugs as Novel Delivery Systems," Vol. 14 of the A.C.S. Symposium Series, and in Bioreversible Carriers in Drug Design, ed. Edward B. Roche, American Pharmaceutical Association and Pergamon Press, 1987, both of which are hereby incorporated by reference in their entirety.

Synthesis

The novel compounds of the present invention can be prepared in a variety of ways known to one skilled in the art of organic synthesis. The compounds of the present invention can be synthesized using the methods as hereinafter described below, together with synthetic methods known in the art of synthetic organic chemistry or variations thereon as appreciated by those skilled in the art.

The compounds of this invention can be prepared from readily available starting materials using the following general methods and procedures. It will be appreciated that where typical or preferred process conditions (i.e., reaction temperatures, times, mole ratios of reactants, solvents, pressures, etc.) are given; other process conditions can also be used unless otherwise stated. Optimum reaction conditions may vary with the particular reactants or solvent used, but such conditions can be determined by one skilled in the art by routine optimization procedures.

The processes described herein can be monitored according to any suitable method known in the art. For example, product formation can be monitored by spectroscopic means, such as nuclear magnetic resonance spectroscopy (e.g., $^1$H or $^{13}$C) infrared spectroscopy, spectrophotometry (e.g., UV-visible), or mass spectrometry, or by chromatography such as high performance liquid chromatography (HPLC) or thin layer chromatography.

Preparation of compounds can involve the protection and deprotection of various chemical groups. The need for protection and deprotection, and the selection of appropriate protecting groups can be readily determined by one skilled in the art. The chemistry of protecting groups can be found, for example, in Greene, et al., Protective Groups in Organic Synthesis, 2d. Ed., Wiley & Sons, 1991, which is incorporated herein by reference in its entirety.

The reactions of the processes described herein can be carried out in suitable solvents which can be readily selected by one of skill in the art of organic synthesis. Suitable solvents can be substantially nonreactive with the starting materials (reactants), the intermediates, or products at the temperatures at which the reactions are carried out, i.e., temperatures which can range from the solvent's freezing temperature to the solvent's boiling temperature. A given reaction can be carried out in one solvent or a mixture of more than one solvent. Depending on the particular reaction step, suitable solvents for a particular reaction step can be selected.

The compounds of the invention can be prepared, for example, using the reaction pathways and techniques described below.

Compounds of the invention can be generally prepared by the method outlined in Scheme 1. A reagent 1-1 (X is a leaving group such as halo) can be reacted with an amine 1-2 (or a salt thereof) in a suitable solvent (e.g., $CH_2Cl_2$) and optionally in the presence of a base such as diisopropyl ethyl amine to provide the desired product 1-3. As an example, a sulfonyl chloride 1-4 can be reacted with amine 1-2 to provide a sulfonyl linked compound 1-5.

base such as LDA at low temperature in a solvent such as tetrahydrofuran (THF) followed by addition of 1-bromo-3-methyl-2-butene 2-2. The resulting intermediate 2-3 can be treated with ozone and then reduced with methyl sulfide to provide the aldehyde 2-4. Reductive amination of 2-4 with an amine 2-5 can be conducted in a solvent such as methanol and with a reducing agent such as sodium triacetoxyborohydride. Then the amination product 2-6 can be cyclized in the presence of a base such as isopropylmagnesium bromide to provide the lactam 2-7 which upon acidic cleavage of the Boc group yields the desired amine 2-8 as a HCl salt.

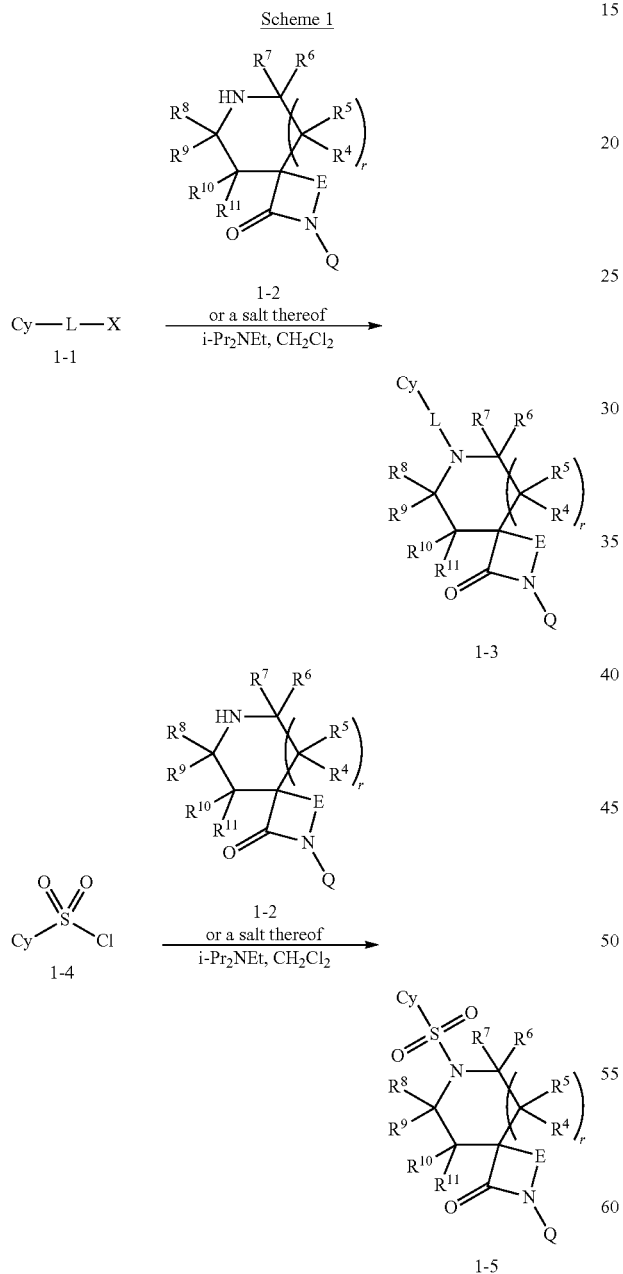

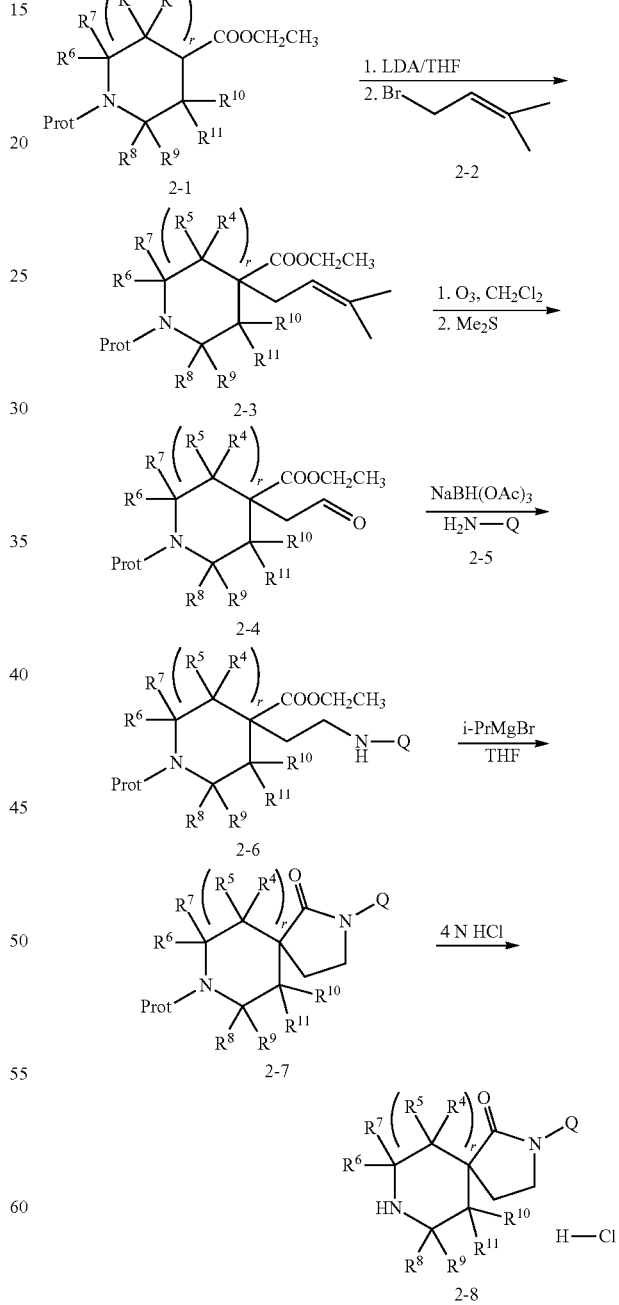

A series of spirocyclyl amines of formula 2-8 can be prepared according to the procedure outlined in Scheme 2. N-protected amine 2-1 (Prot is an amino protecting group such as tert-butyloxycarbonyl (Boc)) can be treated with a A series of amines of formula 3-7 can be prepared according to the procedure outlined in Scheme 3. Treatment of Boc protected ethyl ester 3-1 with a base such as lithium diisopropyl amide (LDA) at low temperature in a solvent such as tetrahydrofuran followed by addition of 1-bromo-3-methyl-2-butene can result in intermediate 3-2 which can be treated with ozone followed by reduction with methyl sulfide to provide the aldehyde 3-3. Reductive amination of 3-3 with an amine 3-4 (where $Q^1$ is, e.g., substituted or unsubstituted cycloalkyl, heterocycloalkyl or heteroaryl) can be conducted in a solvent such as methanol and with a reducing agent such as sodium triacetoxyborohydride. The resulting intermediate 3-5 can be cyclized in the presence of a base such as isopropylmagnesium bromide to provide the lactam 3-6 which upon acidic cleavage of the Boc group yields the desired piperidine 3-7 as a HCl salt.

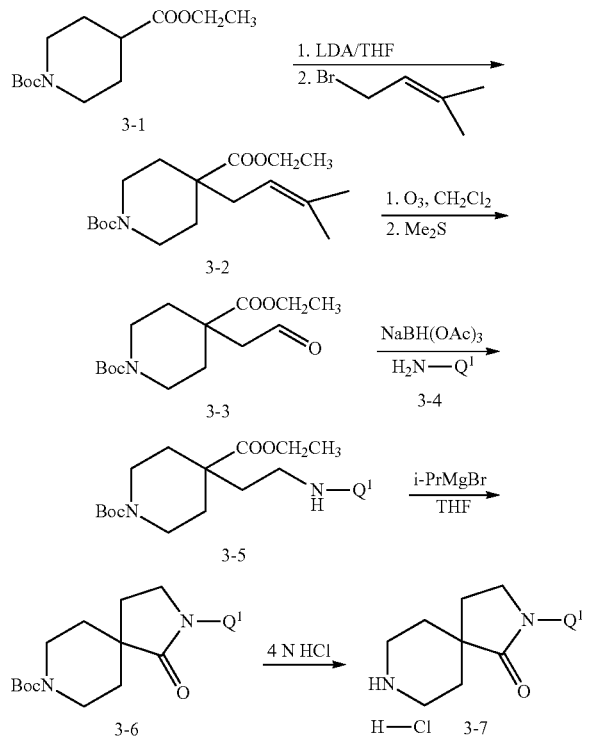

Alternatively, a series of amines of formula 3A-1-3A-7 can be prepared according to the procedure outlined in Scheme 3A.

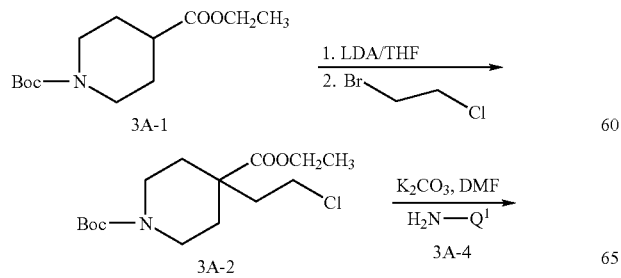

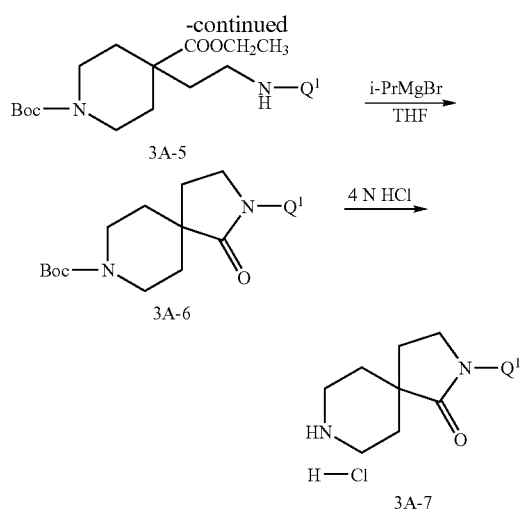

A series of piperidine derivatives 4-4 can be prepared by the methods outlined in Scheme 4. Compound 4-1 can be readily converted to the spirohydantoin 4-2 under Bucherer-Bergs conditions, using, e.g., ammonium carbonate and either sodium cyanide or potassium cyanide in aqueous ethanol. Alkylation of compound 4-2 with one equivalent of alkyl halide QX (X is a leaving group such as halo) in the presence of potassium carbonate in N,N-dimethylformamide (DMF), followed by a second alkylation with $R^{3c}X$ (X is a leaving group such as halo) in the presence of sodium hydride in DMF provides a substituted hydantoin 4-3, which upon acidic cleavage of the Boc group yields the desired piperidine derivative 4-4.

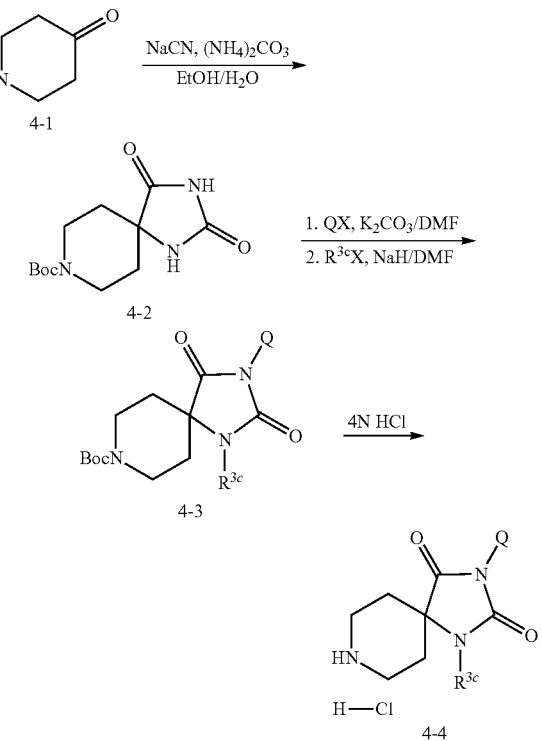

As shown in Scheme 5, alternatively, treatment of a compound 5-1 with an alkyl amine R³ᶜNH₂ and sodium cyanide can provide an alkylated hydantoin derivative 5-2. Heteroaryl substituted hydantoins 5-4 can be obtained by coupling compounds 5-2 with an aromatic boronic acid or aromatic halide 5-3 (wherein Het is an heteroaryl group which is optionally substituted by one or more substituents such as alkyl) in the presence of catalyst. Acidic cleavage of the Boc group yields the desired piperidine derivative 5-5.

Scheme 5

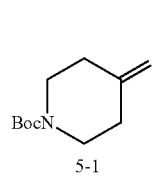
5-1

NaCN, R³ᶜNH₂
⎯⎯⎯⎯⎯⎯⎯→
EtOH/H₂O

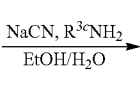
5-2

Het—X¹
5-3
⎯⎯⎯⎯⎯⎯⎯→
Pd catalyst
X¹ = B(OH)₂ or halide

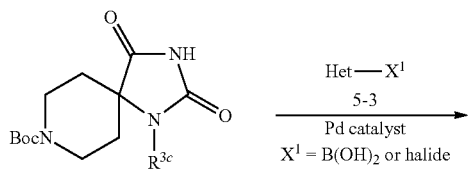
5-4

4N HCl
⎯⎯⎯⎯→

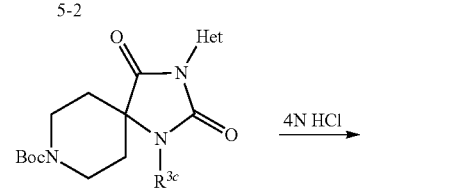
5-5

In a further alternative route, piperidine derivatives 6-6 can be prepared by the method outlined in Scheme 6. A carbobenzyloxy (Cbz) protected amino acid 6-1 can be coupled to an amine Q-NH₂ using a coupling agent such as benzotriazol-1-yloxy)tris(dimethylamino)-phosphonium hexafluorophosphate (BOP) to provide an amide 6-2 which, in turn, can be hydrogenated under Pd catalyst to yield compound 6-3. Compound 6-3 can be treated with methyl chloroformate and a base such as triethyl amine in CH₂Cl₂ to complete the ring closure and form the hydantoin 6-4. N-alkylation of the hydantoin 6-4 with R³ᶜX (X is a leaving group such as halo) can yield compounds of formula 6-5. Acidic cleavage of the Boc group can yield the compound 6-6.

Scheme 6

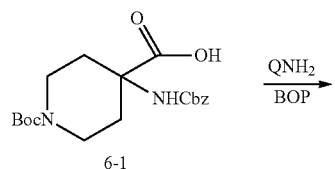
6-1

QNH₂
⎯⎯⎯→
BOP

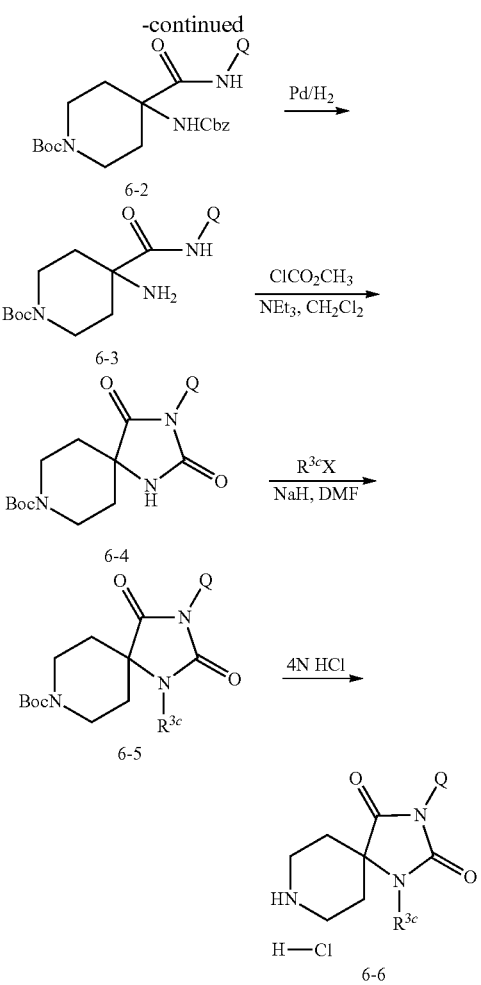

Methods

Compounds of the invention can modulate activity of 11βHSD1. The term "modulate" is meant to refer to an ability to increase or decrease activity of an enzyme. Accordingly, compounds of the invention can be used in methods of modulating 11βHSD1 by contacting the enzyme with any one or more of the compounds or compositions described herein. In some embodiments, compounds of the present invention can act as inhibitors of 11βHSD1. In further embodiments, the compounds of the invention can be used to modulate activity of 11βHSD1 in an individual in need of modulation of the enzyme by administering a modulating amount of a compound of the invention.

The present invention further provides methods of inhibiting the conversion of cortisone to cortisol in a cell, or inhibiting the production of cortisol in a cell, where conversion to or production of cortisol is mediated, at least in part, by 11βHSD1 activity. Methods of measuring conversion rates of cortisone to cortisol and vice versa, as well as methods for measuring levels of cortisone and cortisol in cells, are routine in the art.

The present invention further provides methods of increasing insulin sensitivity of a cell by contacting the cell with a compound of the invention. Methods of measuring insulin sensitivity are routine in the art.

The present invention further provides methods of treating disease associated with activity or expression, including abnormal activity and overexpression, of 11βHSD1 in an individual (e.g., patient) by administering to the individual in need of such treatment a therapeutically effective amount or dose of a compound of the present invention or a pharmaceutical composition thereof.

Example diseases can include any disease, disorder or condition that is directly or indirectly linked to expression or activity of the enzyme or receptor. An 11βHSD1-associated disease can also include any disease, disorder or condition that can be prevented, ameliorated, or cured by modulating enzyme activity.

Examples of 11βHSD1-associated diseases include obesity, diabetes, glucose intolerance, insulin resistance, hyperglycemia, atherosclerosis, hypertension, hyperlipidemia, cognitive impairment, dementia, depression (e.g., psychotic depression), glaucoma, cardiovascular disorders, osteoporosis, and inflammation. Further examples of 11βHSD1-associated diseases include metabolic syndrome, coronary heart disease, type 2 diabetes, hypercortisolemia, androgen excess (hirsutism, menstrual irregularity, hyperandrogenism) and polycystic ovary syndrome (PCOS).

As used herein, the term "cell" is meant to refer to a cell that is in vitro, ex vivo or in vivo. In some embodiments, an ex vivo cell can be part of a tissue sample excised from an organism such as a mammal. In some embodiments, an in vitro cell can be a cell in a cell culture. In some embodiments, an in vivo cell is a cell living in an organism such as a mammal. In some embodiments, the cell is an adipocyte, a pancreatic cell, a hepatocyte, a neuron, or an ocular cell.

As used herein, the term "contacting" refers to the bringing together of indicated moieties in an in vitro system or an in vivo system. For example, "contacting" the 11βHSD1 enzyme with a compound of the invention includes the administration of a compound of the present invention to an individual or patient, such as a human, having 11βHSD1, as well as, for example, introducing a compound of the invention into a sample containing a cellular or purified preparation containing the 11βHSD1 enzyme.

As used herein, the term "individual" or "patient," used interchangeably, refers to any animal, including mammals, preferably mice, rats, other rodents, rabbits, dogs, cats, swine, cattle, sheep, horses, or primates, and most preferably humans.

As used herein, the phrase "therapeutically effective amount" refers to the amount of active compound or pharmaceutical agent that elicits the biological or medicinal response that is being sought in a tissue, system, animal, individual or human by a researcher, veterinarian, medical doctor or other clinician, which includes one or more of the following:

(1) preventing the disease; for example, preventing a disease, condition or disorder in an individual who may be predisposed to the disease, condition or disorder but does not yet experience or display the pathology or symptomatology of the disease;

(2) inhibiting the disease; for example, inhibiting a disease, condition or disorder in an individual who is experiencing or displaying the pathology or symptomatology of the disease, condition or disorder (i.e., arresting further development of the pathology and/or symptomatology); and (3) ameliorating the disease; for example, ameliorating a disease, condition or disorder in an individual who is experiencing or displaying the pathology or symptomatology of the disease, condition or disorder (i.e., reversing the pathology and/or symptomatology).

Pharmaceutical Formulations and Dosage Forms

When employed as pharmaceuticals, the compounds of the invention can be administered in the form of pharmaceutical compositions. These compositions can be prepared in a manner well known in the pharmaceutical art, and can be administered by a variety of routes, depending upon whether local or systemic treatment is desired and upon the area to be treated. Administration may be topical (including ophthalmic and administration to mucous membranes including intranasal, vaginal and rectal delivery), pulmonary (e.g., by inhalation or insufflation of powders or aerosols, including by nebulizer; intratracheal, intranasal, epidermal and transdermal), ocular, oral or parenteral. Methods for ocular delivery can include topical administration (eye drops), subconjunctival, periocular or intravitreal injection or introduction by balloon catheter or ophthalmic inserts surgically placed in the conjunctival sac. Parenteral administration includes intravenous, intraarterial, subcutaneous, intraperitoneal or intramuscular injection or infusion; or intracranial, e.g., intrathecal or intraventricular, administration. Parenteral administration can be in the form of a single bolus dose, or may be, for example, by a continuous perfusion pump. Pharmaceutical compositions and formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable.

This invention also includes pharmaceutical compositions which contain, as the active ingredient, one or more of the compounds of the invention above in combination with one or more pharmaceutically acceptable carriers. In making the compositions of the invention, the active ingredient is typically mixed with an excipient, diluted by an excipient or enclosed within such a carrier in the form of, for example, a capsule, sachet, paper, or other container. When the excipient serves as a diluent, it can be a solid, semi-solid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, suppositories, sterile injectable solutions, and sterile packaged powders.

In preparing a formulation, the active compound can be milled to provide the appropriate particle size prior to combining with the other ingredients. If the active compound is substantially insoluble, it can be milled to a particle size of less than 200 mesh. If the active compound is substantially water soluble, the particle size can be adjusted by milling to provide a substantially uniform distribution in the formulation, e.g. about 40 mesh.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup, and methyl cellulose. The formulations can additionally include: lubricating agents such as talc, magnesium stearate, and mineral oil; wetting agents; emulsifying and suspending agents; preserving agents such as methyl- and propylhydroxy-benzoates; sweetening agents; and flavoring agents. The compositions of the invention can be formulated so as to provide quick, sustained or delayed release of the active ingredient after administration to the patient by employing procedures known in the art.

The compositions can be formulated in a unit dosage form, each dosage containing from about 5 to about 100 mg, more usually about 10 to about 30 mg, of the active ingredient. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient.

The active compound can be effective over a wide dosage range and is generally administered in a pharmaceutically effective amount. It will be understood, however, that the amount of the compound actually administered will usually be determined by a physician, according to the relevant circumstances, including the condition to be treated, the chosen route of administration, the actual compound administered, the age, weight, and response of the individual patient, the severity of the patient's symptoms, and the like.

For preparing solid compositions such as tablets, the principal active ingredient is mixed with a pharmaceutical excipient to form a solid preformulation composition containing a homogeneous mixture of a compound of the present invention. When referring to these preformulation compositions as homogeneous, the active ingredient is typically dispersed evenly throughout the composition so that the composition can be readily subdivided into equally effective unit dosage forms such as tablets, pills and capsules. This solid preformulation is then subdivided into unit dosage forms of the type described above containing from, for example, 0.1 to about 500 mg of the active ingredient of the present invention.

The tablets or pills of the present invention can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

The liquid forms in which the compounds and compositions of the present invention can be incorporated for administration orally or by injection include aqueous solutions, suitably flavored syrups, aqueous or oil suspensions, and flavored emulsions with edible oils such as cottonseed oil, sesame oil, coconut oil, or peanut oil, as well as elixirs and similar pharmaceutical vehicles.

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as described supra. In some embodiments, the compositions are administered by the oral or nasal respiratory route for local or systemic effect. Compositions can be nebulized by use of inert gases. Nebulized solutions may be breathed directly from the nebulizing device or the nebulizing device can be attached to a face masks tent, or intermittent positive pressure breathing machine. Solution, suspension, or powder compositions can be administered orally or nasally from devices which deliver the formulation in an appropriate manner.

The amount of compound or composition administered to a patient will vary depending upon what is being administered, the purpose of the administration, such as prophylaxis or therapy, the state of the patient, the manner of administration, and the like. In therapeutic applications, compositions can be administered to a patient already suffering from a disease in an amount sufficient to cure or at least partially arrest the symptoms of the disease and its complications. Effective doses will depend on the disease condition being treated as well as by the judgment of the attending clinician depending upon factors such as the severity of the disease, the age, weight and general condition of the patient, and the like.

The compositions administered to a patient can be in the form of pharmaceutical compositions described above. These compositions can be sterilized by conventional sterilization techniques, or may be sterile filtered. Aqueous solutions can be packaged for use as is, or lyophilized, the lyophilized preparation being combined with a sterile aqueous carrier prior to administration. The pH of the compound preparations typically will be between 3 and 11, more preferably from 5 to 9 and most preferably from 7 to 8. It will be understood that use of certain of the foregoing excipients, carriers, or stabilizers will result in the formation of pharmaceutical salts.

The therapeutic dosage of the compounds of the present invention can vary according to, for example, the particular use for which the treatment is made, the manner of administration of the compound, the health and condition of the patient, and the judgment of the prescribing physician. The proportion or concentration of a compound of the invention in a pharmaceutical composition can vary depending upon a number of factors including dosage, chemical characteristics (e.g., hydrophobicity), and the route of administration. For example, the compounds of the invention can be provided in an aqueous physiological buffer solution containing about 0.1 to about 10% w/v of the compound for parenteral administration. Some typical dose ranges are from about 1 μg/kg to about 1 g/kg of body weight per day. In some embodiments, the dose range is from about 0.01 mg/kg to about 100 mg/kg of body weight per day. The dosage is likely to depend on such variables as the type and extent of progression of the disease or disorder, the overall health status of the particular patient, the relative biological efficacy of the compound selected, formulation of the excipient, and its route of administration. Effective doses can be extrapolated from dose-response curves derived from in vitro or animal model test systems.

The compounds of the invention can also be formulated in combination with one or more additional active ingredients which can include any pharmaceutical agent such as antiviral agents, antibodies, immune suppressants, anti-inflammatory agents and the like.

Labeled Compounds and Assay Methods

Another aspect of the present invention relates to labeled compounds of the invention (radio-labeled, fluorescent-labeled, etc.) that would be useful not only in radio-imaging but also in assays, both in vitro and in vivo, for localizing and quantitating the enzyme in tissue samples, including human, and for identifying ligands by inhibition binding of a labeled compound. Accordingly, the present invention includes enzyme assays that contain such labeled compounds.

The present invention further includes isotopically-labeled compounds of the invention. An "isotopically" or "radio-labeled" compound is a compound of the invention where one or more atoms are replaced or substituted by an atom having an atomic mass or mass number different from the atomic mass or mass number typically found in nature (i.e., naturally occurring). Suitable radionuclides that may be incorporated in compounds of the present invention include but are not limited to $^{2}H$ (also written as D for deuterium), $^{3}H$ (also written as T for tritium), $^{11}C$, $^{13}C$, $^{14}C$, $^{13}N$, $^{15}N$, $^{15}O$, $^{17}O$, $^{18}O$, $^{18}F$, $^{35}S$, $^{36}Cl$, $^{82}Br$, $^{75}Br$, $^{76}Br$, $^{77}Br$, $^{123}I$, $^{124}I$, $^{125}I$ and $^{131}I$. The radionuclide that is incorporated in the instant radio-labeled compounds will depend on the specific application of that radio-labeled compound. For example, for in vitro receptor labeling and competition assays, compounds that incorporate $^{3}H$, $^{14}C$, $^{82}Br$, $^{125}I$, $^{131}I$, $^{35}S$ or will generally be most useful. For radio-imaging applications $^{11}C$, $^{18}F$, $^{125}I$, $^{123}I$, $^{124}I$, $^{131}I$, $^{75}Br$, $^{76}Br$ or $^{77}Br$ will generally be most useful.

It is understood that a "radio-labeled compound" is a compound that has incorporated at least one radionuclide. In some embodiments the radionuclide is selected from the group consisting of $^{3}H$, $^{14}C$, $^{125}I$, $^{35}S$ and $^{82}Br$.

In some embodiments, the labeled compounds of the present invention contain a fluorescent label.

Synthetic methods for incorporating radio-isotopes and fluorescent labels into organic compounds are well known in the art.

A labeled compound of the invention (radio-labeled, fluorescent-labeled, etc.) can be used in a screening assay to identify/evaluate compounds. For example, a newly synthesized or identified compound (i.e., test compound) which is labeled can be evaluated for its ability to bind a 11βHSD1 by monitoring its concentration variation when contacting with the 11βHSD1, through tracking the labeling. For another example, a test compound (labeled) can be evaluated for its ability to reduce binding of another compound which is known to bind to 11βHSD1 (i.e., standard compound). Accordingly, the ability of a test compound to compete with the standard compound for binding to the 11βHSD1 directly correlates to its binding affinity. Conversely, in some other screening assays, the standard compound is labeled and test compounds are unlabeled. Accordingly, the concentration of the labeled standard compound is monitored in order to evaluate the competition between the standard compound and the test compound, and the relative binding affinity of the test compound is thus ascertained.

Kits

The present invention also includes pharmaceutical kits useful, for example, in the treatment or prevention of 11βHSD1-associated diseases or disorders, obesity, diabetes and other diseases referred to herein which include one or more containers containing a pharmaceutical composition comprising a therapeutically effective amount of a compound of the invention. Such kits can further include, if desired, one or more of various conventional pharmaceutical kit components, such as, for example, containers with one or more pharmaceutically acceptable carriers, additional containers, etc., as will be readily apparent to those skilled in the art. Instructions, either as inserts or as labels, indicating quantities of the components to be administered, guidelines for administration, and/or guidelines for mixing the components, can also be included in the kit.

The invention will be described in greater detail by way of specific examples. The following examples are offered for illustrative purposes, and are not intended to limit the invention in any manner. Those of skill in the art will readily recognize a variety of noncritical parameters which can be changed or modified to yield essentially the same results. Certain compounds of the Examples were found to be inhibitors of 11βHSD1 according to one or more of the assays provided herein.

EXAMPLES

Example 1

8-(3-Chloropyridin-2-yl)-2-cyclohexyl-2,8-diazaspiro[4.5]decan-1-one

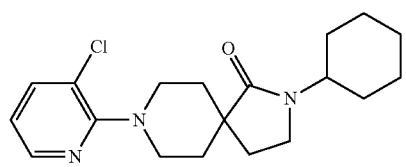

1) 1-Benzyl 4-methylpiperidine-1,4-dicarboxylate

Benzyl chloroformate (11.0 mL, 0.0768 mol) was added into a solution of methyl piperidine-4-carboxylate (10.0 g, 0.0698 mol) and 4-methylmorpholine (15.4 mL, 0.140 mol) in acetonitrile (20.0 mL). After 30 min, the mixture was diluted with NaHCO$_3$ (7.5%), extracted with ethyl acetate (AcOEt) (3×30 mL). The combined organic layers were dried over Na$_2$SO$_4$, filtered, concentrated to afford 1-benzyl 4-methyl piperidine-1,4-dicarboxylate (12 gram) which was directly used in next step without further purification.

2) 1-Benzyl 4-methyl 4-(2-chloroethyl)piperidine-1,4-dicarboxylate

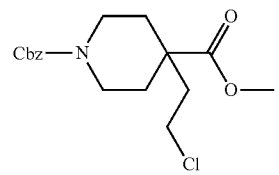

Lithium bis(trimethylsilyl)amide (LiHMDS) in THF (1.0 M, 7.2 mL, 0.0072 mol) was added to a solution of 1-benzyl 4-methyl piperidine-1,4-dicarboxylate (1.00 g, 0.00360 mol) in tetrahydrofuran (10.0 mL) at −78° C. The reaction mixture had been stirred at −78° C. for 1 hr, then 1-bromo-2-chloroethane (0.45 mL, 0.0054 mol) was slowly added to the mixture. The reaction mixture was allowed to warm to room temperature and stirred for 2 hrs. The reaction was quenched with saturated NH$_4$Cl, extracted with ethyl acetate. The combined organic layers were dried over Na$_2$SO$_4$, filtered, concentrated. The residue was flash chromatographed (ethyl acetate in hexane: 20%) to afford 1-benzyl 4-methyl 4-(2-chloroethyl)piperidine-1,4-dicarboxylate.

3) Benzyl 2-cyclohexyl-1-oxo-2,8-diazaspiro[4.5] decane-8-carboxylate

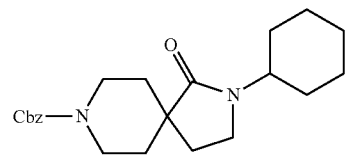

A mixture of 1-benzyl 4-methyl 4-(2-chloroethyl)piperidine-1,4-dicarboxylate (0.5 g, 0.001 mol), cyclohexanamine (0.18 mL, 0.0016 mol), sodium iodide (0.22 g, 0.0015 mol) and potassium carbonate (0.61 g, 0.0044 mol) in DMF (5.0 mL) was stirred and heated at 120° C. for overnight. Then the reaction mixture was diluted with brine, and extracted with ethyl acetate (3X). The combined organic layers were dried over Na$_2$SO$_4$, filtered, and concentrated. The residue was purified by combiflash (ethyl acetate in hexanes: 40%) to give 180 mg of benzyl 2-cyclohexyl-1-oxo-2,8-diazaspiro[4.5]decane-8-carboxylate.

4) 2-Cyclohexyl-2,8-diazaspiro[4.5]decan-1-one

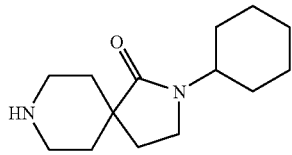

Pd/C (100 mg) was added into a solution of benzyl 2-cyclohexyl-1-oxo-2,8-diazaspiro[4.5]decane-8-carboxylate (1.0 g, 0.0027 mol) in methanol (10 mL) under N$_2$. The reaction mixture was stirred under an atmosphere of hydrogen for 2 hrs. The mixture was filtered. The filtrate was concentrated to give 2-cyclohexyl-2,8-diazaspiro[4.5]decan-1-one which was directly used in next step reaction without further purification.

5) 8-(3-Chloropyridin-2-yl)-2-cyclohexyl-2,8-diazaspiro[4.5]decan-1-one

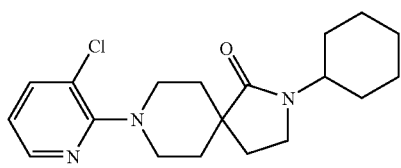

A mixture of 2-cyclohexyl-2,8-diazaspiro[4.5]decan-1-one (20 mg, 0.00008 mol), 2,3-dichloropyridine (15.0 mg, 0.000102 mol) and N,N-diisopropylethylamine (44 µL, 0.00025 mol) in N-methylpyrrolidin-2-one (1.0 mL) was irradiated under microwave at 200° C. for 15 min. The mixture was adjusted acidic (pH to −2.0) with trifluoroacetic acid (TFA), and was diluted with methanol (0.8 mL). The resulting solution was purified by Prep-HPLC to give 8-(3-chloropyridin-2-yl)-2-cyclohexyl-2,8-diazaspiro[4.5]decan-1-one. LCMS: (M+H)$^+$=348.20/350.20.

Example 2

8-(5-Chloro-3-fluoropyridin-2-yl)-2-cyclohexyl-2,8-diazaspiro[4.5]decan-1-one

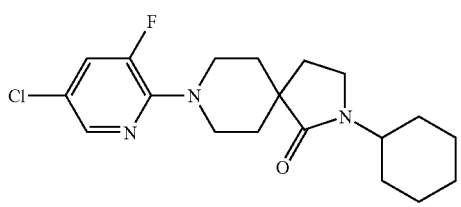

This compound was prepared using procedures analogous to those for Example 1. LCMS: (M+H)$^+$=366.20/368.20.

Example 3

2-(2-Cyclohexyl-1-oxo-2,8-diazaspiro[4.5]dec-8-yl)nicotinonitrile

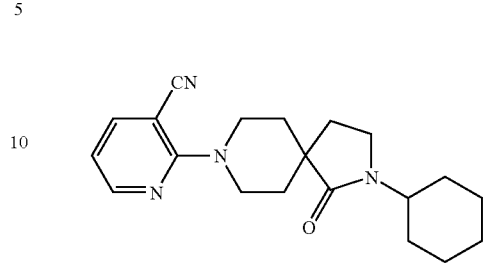

This compound was prepared using procedures analogous to those for Example 1. LCMS: (M+H)$^+$=339.20.

Example 4

2-Cyclohexyl-8-[3-(trifluoromethyl)pyridin-2-yl]-2,8-diazaspiro[4.5]decan-1-one

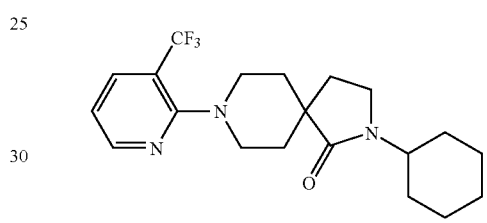

This compound was prepared using procedures analogous to those for Example 1. LCMS: (M+H)$^+$=382.20.

Example 5

8-[5-(4-Chlorophenyl)pyridin-2-yl]2-cyclohexyl-2,8-diazaspiro[4.5]decan-1-one

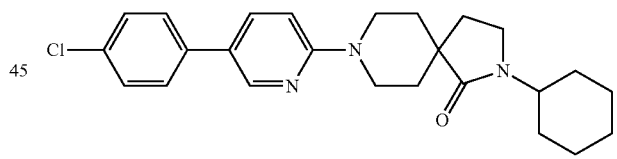

This compound was prepared using procedures analogous to those for Example 1. LCMS: (M+H)$^+$=424.2/426.2.

Example 6

8-Benzoyl-2-cyclohexyl-2,8-diazaspiro[4.5]decan-1-one

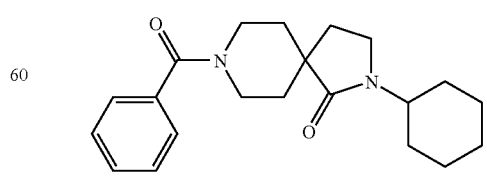

Benzoyl chloride (15 µL, 0.00013 mol) was added to a solution of 2-cyclohexyl-2,8-diazaspiro[4.5]decan-1-one (20.0 mg, 0.0000846 mol) and N,N-diisopropylethylamine (44 μL, 0.00025 mol) in N,N-dimethylformamide (1.0 mL). The mixture was stirred at room temperature for 30 min, then adjusted to be acidic (pH to −2.0) with TFA, and diluted with methanol (0.8 mL). The resulting solution was purified by Prep-HPLC to give 8-benzoyl-2-cyclohexyl-2,8-diazaspiro[4.5]decan-1-one. LCMS: (M+H)$^+$=341.20.

Example 7

2-Cyclohexyl-8-(cyclohexylcarbonyl)-2,8-diazaspiro[4.5]decan-1-one

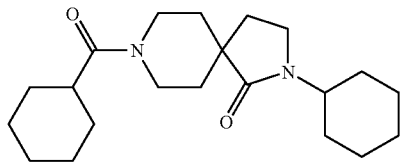

This compound was prepared using procedures analogous to those for Example 6. LCMS: (M+H)$^+$=347.3.

Example 8

2-Cyclohexyl-8-(piperidin-1-ylcarbonyl)-2,8-diazaspiro[4.5]decan-1-one

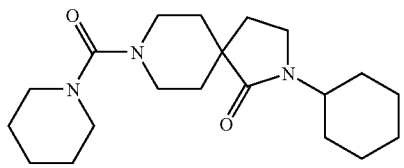

This compound was prepared using procedures analogous to those for Example 6. LCMS: (M+H)$^+$=348.30.

Example 9

8-[(3-Chloro-2-methylphenyl)sulfonyl]2-cyclohexyl-2,8-diazaspiro[4.5]decan-1-one

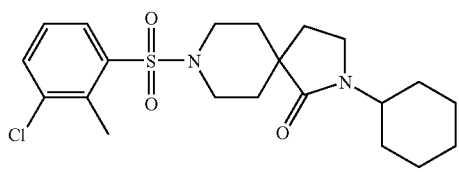

This compound was prepared using procedures analogous to those for Example 6. LCMS: (M+H)$^+$=425.1/427.1.

Example 10

4-[2-(trans-4-Hydroxycyclohexyl)-1-oxo-2,8-diazaspiro[4.5]dec-8-yl]benzonitrile

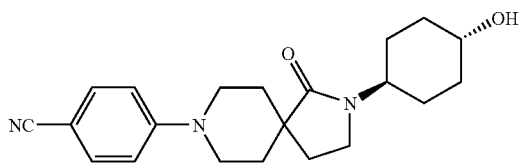

1) 1-Benzyl 4-methyl 4-allylpiperidine-1,4-dicarboxylate

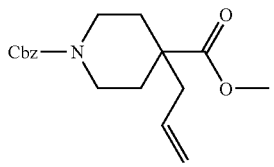

Lithium bis(trimethylsilyl)amide (LiHMDS) in THF (1.0 M, 45 mL) was added to a solution of 1-benzyl 4-methyl piperidine-1,4-dicarboxylate (10.0 g, 0.0360 mol) at −78° C. The reaction mixture was slowly warmed to −50° C. and kept at this temperature for 10 min, and then re-cooled to −78° C. 3-Iodo-1-propene (4.95 mL, 0.0541 mol) was added slowly. After the addition, the mixture was allowed to warm slowly to room temperature and kept at room temperature for 3 hours. The mixture was carefully quenched (the pH was adjusted to 4) with 1N HCl solution, and ethyl acetate (200 mL) was added. The organic layer was separated and washed with water, NaHCO$_3$ (7.5%), brine, dried over MgSO$_4$, and filtered. The filtrate was concentrated. The residue was purified by flash chromatography with 20% ethyl acetate in hexane to give 1-benzyl 4-methyl 4-allylpiperidine-1,4-dicarboxylate (10.4 g, 90.9%).

2) 1-Benzyl 4-methyl 4-(2-oxoethyl)piperidine-1,4-dicarboxylate

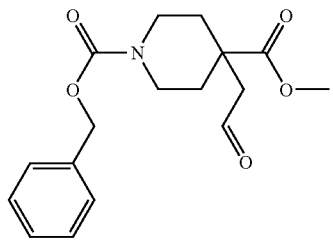

Ozone was passed through a solution of 1-benzyl 4-methyl 4-allylpiperidine-1,4-dicarboxylate (10.0 g, 0.0315 mol) in methylene chloride (200.0 mL) at −78° C. until the color of the solution turned to steel blue. The reaction mixture was flushed with an atmosphere of nitrogen. Then to the solution was added dimethyl sulfate (6.0 mL, 0.063 mol) followed by triethylamine (8.8 mL, 0.063 mol). The mixture was stirred at room temperature for overnight, and then concentrated. The residue was dissolved in ethyl acetate, and the resulting solution was washed with saturated NH$_4$Cl solution, NaHCO$_3$ (7.5%), brine, dried over Na₂SO₄, filtered and concentrated to give 1-benzyl 4-methyl 4-(2-oxoethyl)piperidine-1,4-dicarboxylate.

3) Benzyl 2-(trans-4-hydroxycyclohexyl)-1-oxo-2,8-diazaspiro[4.5]decane-8-carboxylate

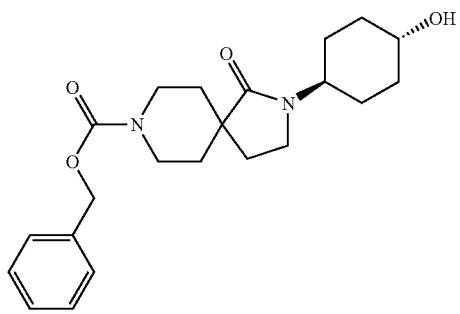

A mixture of 1-benzyl 4-methyl 4-(2-oxoethyl)piperidine-1,4-dicarboxylate (4.80 g, 0.0150 mol), trans-4-aminocyclohexanol hydrochloride (2.5 g, 0.016 mol) and triethylamine (3.3 mL, 0.024 mol) in 1,2-dichloroethane (30.0 mL) was stirred at room temperature for 30 min. To the mixture was added sodium triacetoxyborohydride (7.9 g, 0.038 mol) with stirring. The mixture was stirred at room temperature for 1 h, then was heated at 80° C. for 2 h. After cooling, the mixture was diluted with dichloromethane, and washed with 1N HCl solution, NaHCO₃ (7.5%), water, and brine successively, dried over Na₂SO₄, filtered, and concentrated. The residue was purified by flash chromatography to give benzyl 2-(trans-4-hydroxycyclohexyl)-1-oxo-2,8-diazaspiro[4.5]decane-8-carboxylate (4.20 g, 72.0%).

4) 2-(trans-4-Hydroxycyclohexyl)-2,8-diazaspiro[4.5]decan-1-one

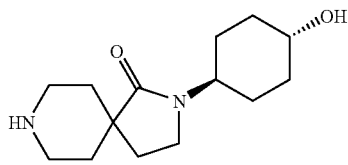

200 mg of Pd/C was added a solution of benzyl 2-(trans-4-hydroxycyclohexyl)-1-oxo-2,8-diazaspiro[4.5]decane-8-carboxylate (2.13 g, 0.00551 mol) in methanol (50 mL) under nitrogen. The reaction mixture was stirred under an atmosphere of hydrogen for 3 hrs. The mixture was filtered, and the filtrate was concentrated to give 2-(trans-4-hydroxycyclohexyl)-2,8-diazaspiro[4.5]decan-1-one (1.29 g, 93%).

5) 4-[2-(trans-4-Hydroxycyclohexyl)-1-oxo-2,8-diazaspiro[4.5]dec-8-yl]benzonitrile

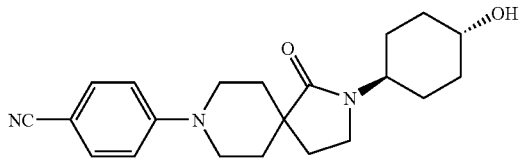

A mixture of 2-(trans-4-hydroxycyclohexyl)-2,8-diazaspiro[4.5]decan-1-one (20 mg, 0.00008 mol), 4-fluorobenzonitrile (12.3 mg, 0.000102 mol) and N,N-diisopropylethylamine (44 µL, 0.00025 mol) in N-methylpyrrolidinone (0.5 mL) was irradiated under microwave at 200° C. for 15 min. The mixture was diluted with methanol (1.3 mL), and purified by Prep-HPLC to give 4-[2-(trans-4-hydroxycyclohexyl)-1-oxo-2,8-diazaspiro[4.5]dec-8-yl]benzonitrile. LCMS: (M+H)⁺=354.2.

Example 11

3-Fluoro-4-[2-(trans-4-hydroxycyclohexyl)-1-oxo-2,8-diazaspiro[4.5]dec-8-yl]benzonitrile

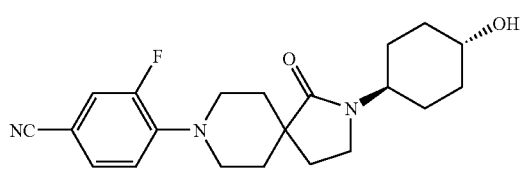

This compound was prepared using procedures analogous to those for Example 10. LCMS: (M+H)⁺=372.20.

Example 12

3,5-Difluoro-4-[2-(trans-4-hydroxycyclohexyl)-1-oxo-2,8-diazaspiro[4.5]dec-8-yl]benzonitrile

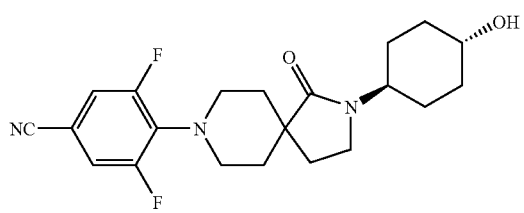

This compound was prepared using procedures analogous to those for Example 10. LCMS: (M+H)⁺=390.20.

Example 13

8-(3-Fluoropyridin-2-yl)-2-(trans-4-hydroxycyclohexyl)-2,8-diazaspiro[4.5]decan-1-one:

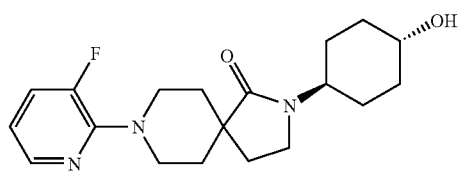

This compound was prepared using procedures analogous to those for Example 10. LCMS: (M+H)⁺=348.20.

Example 14

8-(3-Chloropyridin-2-yl)-2-(trans-4-hydroxycylohexyl)-2,8-diazaspiro[4.5]decan-1-one

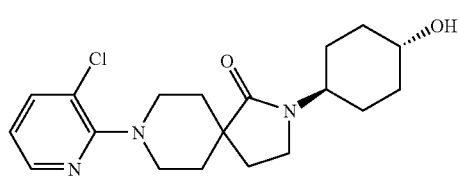

This compound was prepared using procedures analogous to those for Example 10. LCMS: (M+H)⁺=364.20, 366.20.

Example 15

2-[2-(trans-4-Hydroxycyclohexyl)-1-oxo-2,8-diaza-spiro[4.5]dec-8-yl]nicotinonitrile

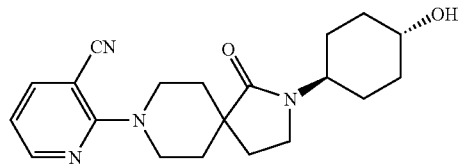

This compound was prepared using procedures analogous to those for Example 10. LCMS: (M+H)$^+$=355.20.

Example 16

2-(trans-4-Hydroxycyclohexyl)-8-[3-(trifluoromethyl)pyridin-2-yl]2,8-diazaspiro[4.5]decan-1-one

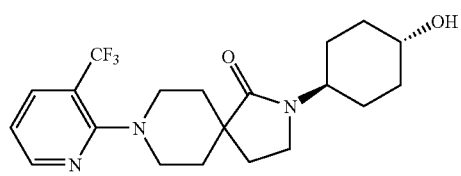

This compound was prepared using procedures analogous to those for Example 10. LCMS: (M+H)$^+$=398.20.

Example 17

2-(trans-4-Hydroxycyclohexyl)-8-[4-(trifluoromethyl)pyridin-2-yl]2,8-diazaspiro[4.5]decan-1-one

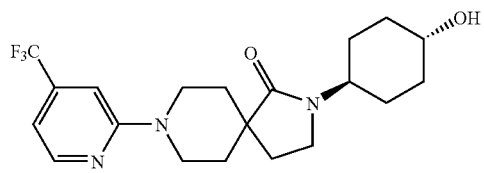

This compound was prepared using procedures analogous to those for Example 10. LCMS: (M+H)$^+$=398.20.

Example 18

2-[2-(trans-4-Hydroxycyclohexyl)-1-oxo-2,8-diaza-spiro[4.5]dec-8-yl]isonicotinonitrile

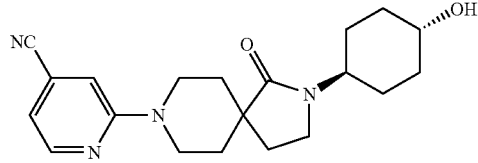

This compound was prepared using procedures analogous to those for Example 10. LCMS: (M+H)$^+$=355.20.

Example 19

8-(2-Chloropyridin-4-yl)-2-(trans-4-hydroxynyclo-hexyl)-2,8-diazaspiro[4.5]decan-1-one

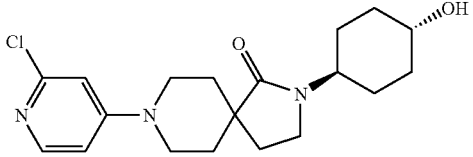

This compound was prepared using procedures analogous to those for Example 10. LCMS: (M+H)$^+$=364.20/366.20.

Example 20

8-(5-Fluoropyridin-2-yl)-2-(trans-4-hydroxycyclo-hexyl)-2,8-diazaspiro[4.5]decan-1-one

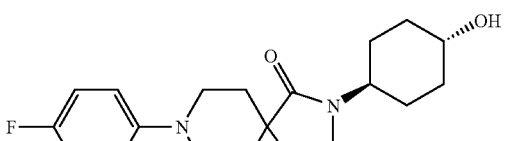

This compound was prepared using procedures analogous to those for Example 10. LCMS: (M+H)$^+$=348.20.

Example 21

8-(5-Chloropyridin-2-yl)-2-(trans-4-hydroxynyclo-hexyl)-2,8-diazaspiro[4.5]decan-1-one

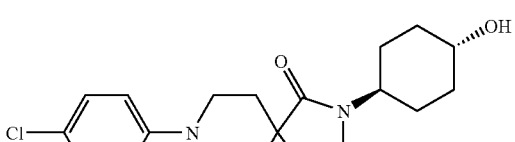

This compound was prepared using procedures analogous to those for Example 10. LCMS: (M+H)$^+$=364.20/366.20.

Example 22

8-(5-Bromopyridin-2-yl)-2-(trans-4-hydroxycyclo-hexyl)-2,8-diazaspiro[4.5]decan-1-one

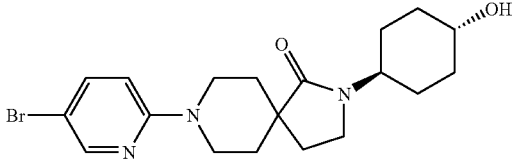

This compound was prepared using procedures analogous to those for Example 10. LCMS: (M+H)$^+$=408.1/410.1.

Example 23

6-[2-(trans-4-Hydroxycyclohexyl)-1-oxo-2,8-diaza-spiro[4.5]dec-8-yl]nicotinonitrile

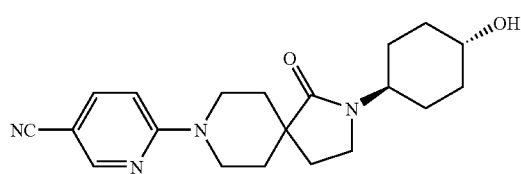

This compound was prepared using procedures analogous to those for Example 10. LCMS: $(M+H)^+=355.20$.

Example 24

2-(trans-4-Hydroxycyclohexyl)-8-[5-(trifluoromethyl)pyridin-2-yl]2,8-diazaspiro[4.5]decan-1-one

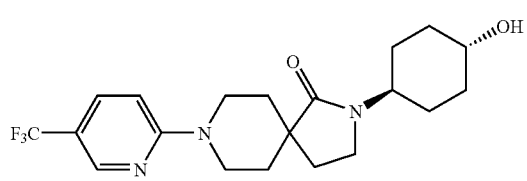

This compound was prepared using procedures analogous to those for Example 10. LCMS: $(M+H)^+=398.20$.

Example 25

8-(3,5-Difluoropyridin-2-yl)-2-(trans-4-hydroxycyclohexyl)-2,8-diazaspiro[4.5]decan-1-one

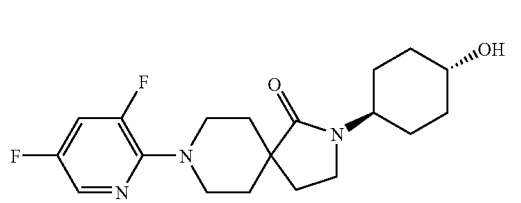

This compound was prepared using procedures analogous to those for Example 10. LCMS: $(M+H)^+=366.20$.

Example 26

8-(5-Chloro-3-fluoropyridin-2-yl)-2-(trans-4-hydroxycyclohexyl)-2,8-diazaspiro[4.5]decan-1-one

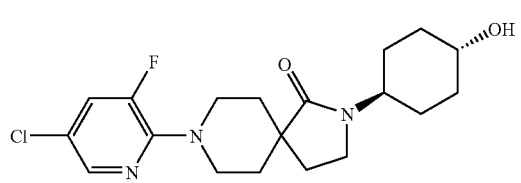

This compound was prepared using procedures analogous to those for Example 10. LCMS: $(M+H)^+=382.2/384.2$.

Example 27

8-(3,5-Dichloropyridin-2-yl)-2-(trans-4-hydroxycyclohexyl)-2,8-diazaspiro[4.5]decan-1-one

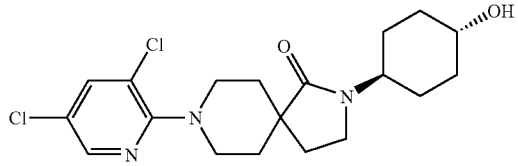

This compound was prepared using procedures analogous to those for Example 10. LCMS: $(M+H)^+=398.1, 400.2/402.1$.

Example 28

8-(5-Bromo-3-fluoropyridin-2-yl)-2-(trans-4-hydroxynyclohexyl)-2,8-diazaspiro[4.5]decan-1-one

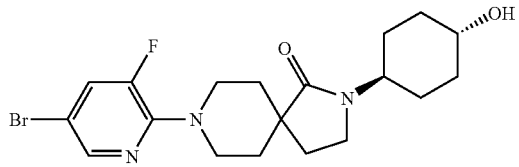

This compound was prepared using procedures analogous to those for Example 10. LCMS: $(M+H)^+=426.10/428.1$.

Example 29

8-(5-Bromo-3-chloropyridin-2-yl)-2-(trans-4-hydroxynyclohexyl)-2,8-diazaspiro[4.5]decan-1-one

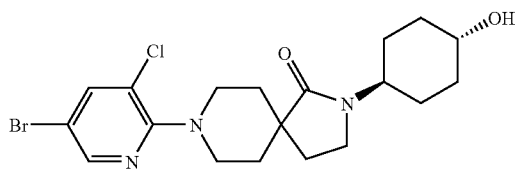

This compound was prepared using procedures analogous to those for Example 10. LCMS: $(M+H)^+=442.0/444.1/446.0$.

Example 30

8-[3-Chloro-5-(trifluoromethyl)pyridin-2-yl]2-(trans-4-hydroxycyclohexyl)-2,8-diazaspiro[4.5]decan-1-one

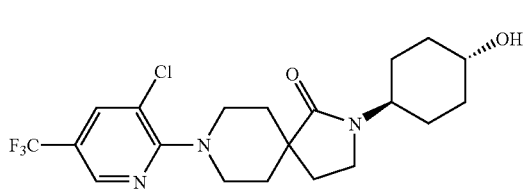

This compound was prepared using procedures analogous to those for Example 10. LCMS: $(M+H)^+=432.2/434.2$.

Example 31

2-(trans-4-Hydroxycyclohexyl)-8-[(trifluoromethyl)pyridin-2-yl]2,8-diazaspiro[4.5]decan-1-one

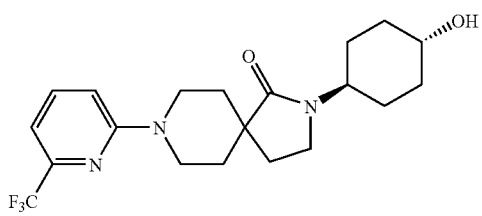

This compound was prepared using procedures analogous to those for Example 10. LCMS: (M+H)$^+$=398.20.

Example 32

8-(6-Fluoropyridin-2-yl)-2-(trans-4-hydroxycyclohexyl)-2,8-diazaspiro[4.5]decan-1-one

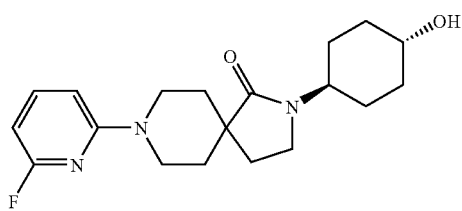

This compound was prepared using procedures analogous to those for Example 10. LCMS: (M+H)$^+$=348.20.

Example 33

2-(trans-4-Hydroxycyclohexyl)-8-(3,5,6-trifluoro-4-methylpyridin-2-yl)-2,8-diazaspiro[4.5]decan-1-one

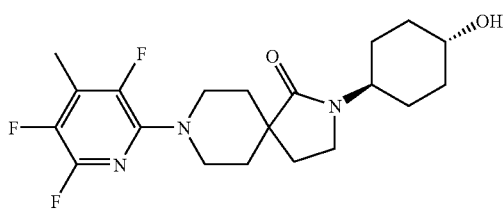

This compound was prepared using procedures analogous to those for Example 10. LCMS: (M+H)$^+$=398.20.

Example 34

6-[2-(trans-4-Hydroxycyclohexyl)-1-oxo-2,8-diazaspiro[4.5]dec-8-yl]-2-methylnicotinonitrile

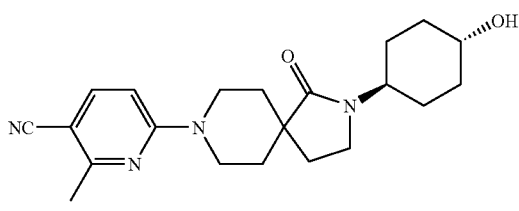

This compound was prepared using procedures analogous to those for Example 10. LCMS: (M+H)$^+$=369.20.

Example 35

2-(trans-4-Hydroxycyclohexyl)-8-[6-methyl-4-(trifluoromethyl)pyridin-2-yl]-2,8-diazaspiro[4.5]decan-1-one

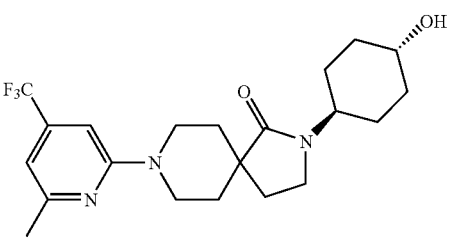

This compound was prepared using procedures analogous to those for Example 10. LCMS: (M+H)$^+$=412.10.

Example 36

8-[3-Fluoro-4-(trifluoromethyl)pyridin-2-yl]2-(trans-4-hydroxycyclohexyl)-2,8-diazaspiro[4.5]decan-1-one

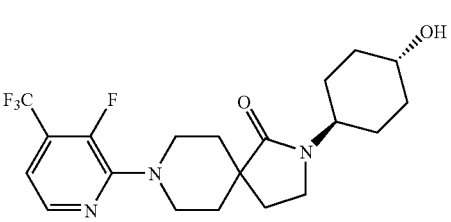

This compound was prepared using procedures analogous to those for Example 10. LCMS: (M+H)$^+$=416.20.

Example 37

8-(3-Fluoropyridin-4-yl)-2-(trans-4-hydroxycyclohexyl)-2,8-diazaspiro[4.5]decan-1-one

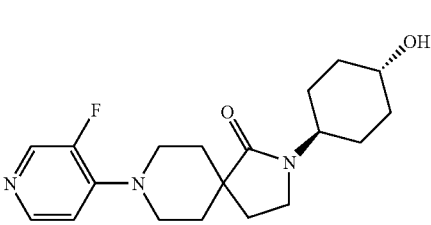

This compound was prepared using procedures analogous to those for Example 10. LCMS: (M+H)$^+$=348.20.

Example 38

8-(5-Fluoropyrimidin-2-yl)-2-(trans-4-hydroxycyclohexyl)-2,8-diazaspiro[4.5]decan-1-one

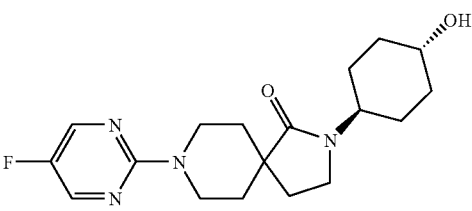

This compound was prepared using procedures analogous to those for Example 10. LCMS: (M+H)$^+$=349.20.

Example 39

8-(5-Ethylpyrimidin-2-yl)-2-(trans-4-trans-4-hydroxycylohexyl)-2,8-diazaspiro[4.5]decan-1-one

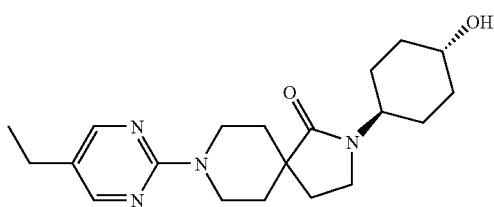

This compound was prepared using procedures analogous to those for Example 10. LCMS: (M+H)$^+$=359.30.

Example 40

8-(5-Bromopyrimidin-2-yl)-2-(trans-4-hydroxycyclohexyl)-2,8-diazaspiro[4.5]decan-1-one

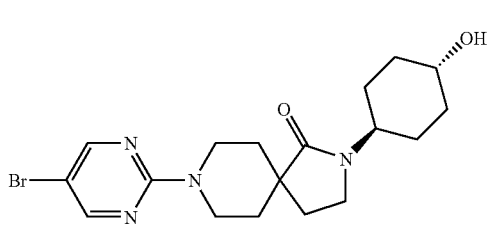

This compound was prepared using procedures analogous to those for Example 10. LCMS: (M+H)$^+$=409.10/411.10.

Example 41

3-[2-(trans-4-Hydroxycyclohexyl)-1-oxo-2,8-diazaspiro[4.5]dec-8-yl]pyrazine-2-carbonitrile

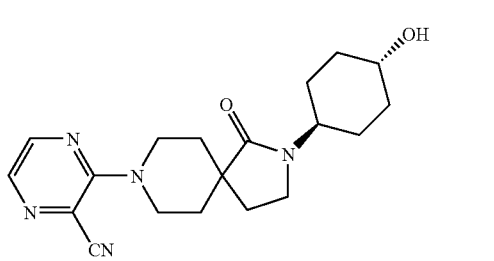

This compound was prepared using procedures analogous to those for Example 10. LCMS: (M+H)$^+$=356.20.

Example 42

8-(1,3-Benzothiazol-2-yl)-2-(trans-4-hydroxycyclohexyl)-2,8-diazaspiro[4.5]decan-1-one

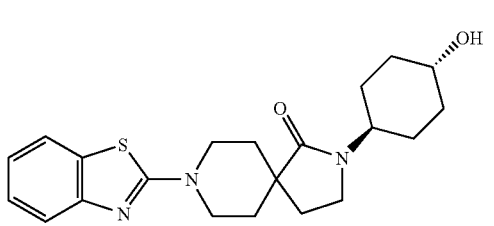

This compound was prepared using procedures analogous to those for Example 10. LCMS: (M+H)$^+$=386.20.

Example 43

8-(3-Fluoropyridin-2-yl)-2-(cis-4-hydroxycyclohexyl)-2,8-diazaspiro[4.5]decan-1-one

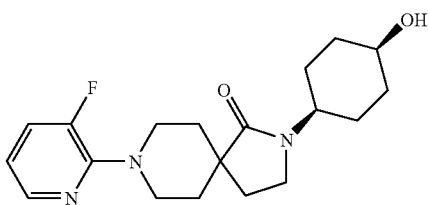

1) Benzyl 2-(cis-4-hydroxycyclohexyl)-1-oxo-2,8-diazaspiro[4.5]decane-8-carboxylate

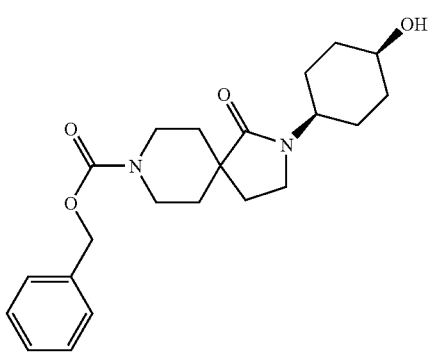

A mixture of 1-benzyl 4-methyl 4-(2-oxoethyl)piperidine-1,4-dicarboxylate (4.80 g, 0.0150 mol), cis-4-aminocyclohexanol hydrochloride (2.5 g, 0.016 mol) and triethylamine (3.3 mL, 0.024 mol) in 1,2-dichloroethane (30.0 mL) was stirred at room temperature for 30 min. To the mixture was added sodium triacetoxyborohydride (7.9 g, 0.038 mol) with stirring. The mixture was stirred at room temperature for 1 h, then was heated at 80° C. for 2 h. After cooling, the mixture was diluted with dichloromethane, and washed with 1N HCl solution, NaHCO$_3$ (7.5%), water, and brine successively, dried over Na$_2$SO$_4$, filtered, and concentrated. The residue was purified by flash chromatography to give benzyl 2-(cis-4-hydroxycyclohexyl)-1-oxo-2,8-diazaspiro[4.5]decane-8-carboxylate (4.20 g, 72.0%).

2) 2-(cis-4-Hydroxycyclohexyl)-2,8-diazaspiro[4.5]decan-1-one

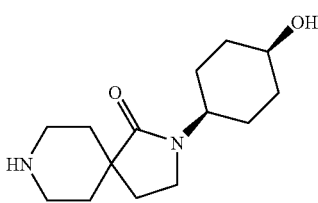

200 mg of Pd/C was added a solution of benzyl 2-(cis-4-hydroxycyclohexyl)-1-oxo-2,8-diazaspiro[4.5]decane-8-carboxylate (2.13 g, 0.00551 mol) in methanol (50 mL) under nitrogen. The reaction mixture was stirred under an atmosphere of hydrogen for 3 hrs. The mixture was filtered, and the 3) 8-(3-fluoropyridin-2-yl)-2-(cis-4-hydroxycyclo-hexyl)-2,8-diazaspiro[4.5]decan-1-one

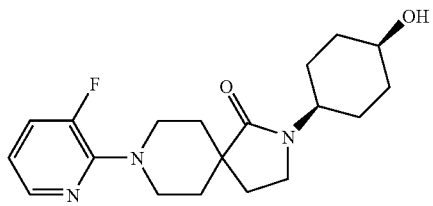

A mixture of 2-(cis-4-hydroxycyclohexyl)-2,8-diazaspiro[4.5]decan-1-one (20 mg, 0.08 mmol), 4-fluorobenzonitrile (12.3 mg, 0.102 mmol) and N,N-diisopropylethylamine (44 μL, 0.25 mmol) in N-methylpyrrolidinone (0.5 mL) was irradiated under microwave at 200° C. for 15 min. The mixture was diluted with methanol (1.3 mL), and purified by Prep-HPLC to give 8-(3-fluoropyridin-2-yl)-2-(cis-4-hydroxycyclohexyl)-2,8-diazaspiro[4.5]decan-1-one. LCMS: (M+H)$^+$=348.2.

Example 44

8-(3-Chloropyridin-2-yl)-2-(cis-4-hydroxycyclo-hexyl)-2,8-diazaspiro[4.5]decan-1-one

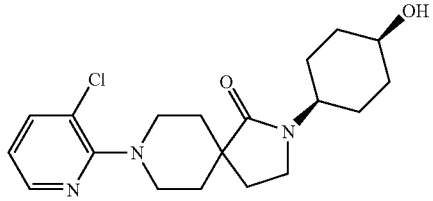

This compound was prepared using procedures analogous to those for Example 43. LCMS: (M+H)$^+$=364.2/266.2.

Example 45

2-[2-(Cis-4-hydroxycyclohexyl)-1-oxo-2,8-diaza-spiro[4.5]dec-8-yl]nicotinonitrile

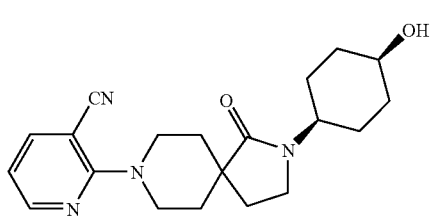

This compound was prepared using procedures analogous to those for Example 43. LCMS: (M+H)$^+$=355.2.

Example 46

8-(3,5-Difluoropyridin-2-yl)-2-(cis-4-hydroxycyclo-hexyl)-2,8-diazaspiro[4.5]decan-1-one

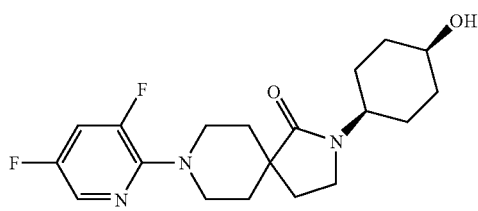

This compound was prepared using procedures analogous to those for Example 43. LCMS: (M+H)$^+$=366.2.

Example 47

8-(2,5-Difluoropyridin-3-yl)-2-(cis-4-hydroxycyclo-hexyl)-2,8-diazaspiro[4.5]decan-1-one

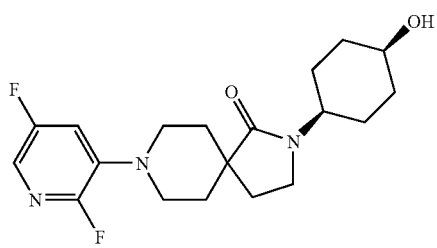

This compound was prepared using procedures analogous to those for Example 43. LCMS: (M+H)$^+$=366.2.

Example 48

8-(5-Chloro-3-fluoropyridin-2-yl)-2-(cis-4-hydroxy-cyclohexyl)-2,8-diazaspiro[4.5]decan-1-one

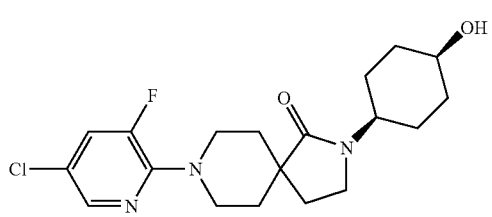

This compound was prepared using procedures analogous to those for Example 43. LCMS: (M+H)$^+$=382.2/384.2.

Example 49

8-(5-Chloro-2-fluoropyridin-3-yl)-2-(cis-4-hydroxy-cyclohexyl)-2,8-diazaspiro[4.5]decan-1-one

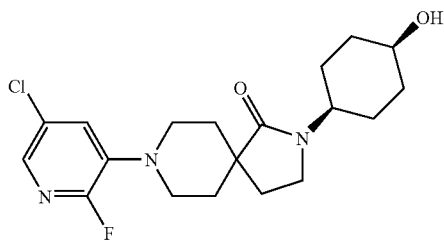

This compound was prepared using procedures analogous to those for Example 43. LCMS: (M+H)$^+$=382.2/384.2.

Example 50

8-(3,5-Dichloropyridin-2-yl)-2-(cis-4-hydroxycyclo-hexyl)-2,8-diazaspiro[4.5]decan-1-one

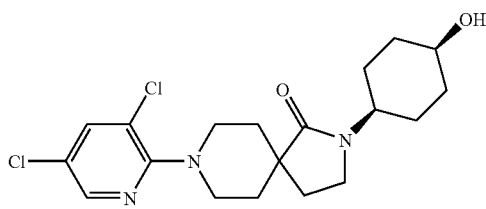

This compound was prepared using procedures analogous to those for Example 43. LCMS: (M+H)$^+$=398.2/400.2.

Example 51

8-(5-Bromo-3-fluoropyridin-2-yl)-2-(cis-4-hydroxy-cyclohexyl)-2,8-diazaspiro[4.5]decan-1-one

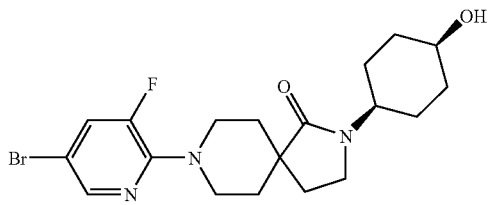

This compound was prepared using procedures analogous to those for Example 43. LCMS: (M+H)$^+$=426.1/428.1.

Example 52

8-(5-Bromo-3-chloropyridin-2-yl)-2-(cis-4-hydroxy-cyclohexyl)-2,8-diazaspiro[4.5]decan-1-one

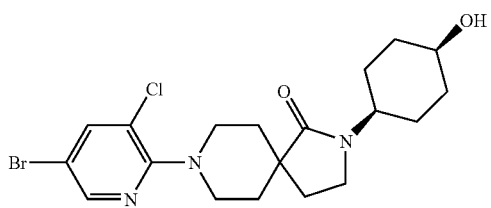

This compound was prepared using procedures analogous to those for Example 43. LCMS: (M+H)$^+$=442.1/444.1.

Example 53

2-(Cis-4-hydroxycyclohexyl)-8-[4-(trifluoromethyl)pyridin-2-yl]2,8-diazaspiro[4.5]decan-1-one

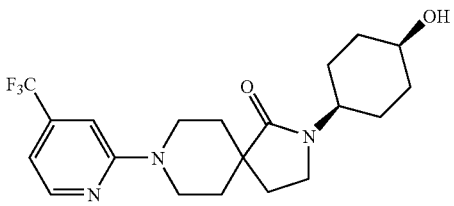

This compound was prepared using procedures analogous to those for Example 43. LCMS: (M+H)$^+$=398.2.

Example 54

2-[2-(Cis-4-hydroxycyclohexyl)-1-oxo-2,8-diaza-spiro[4.5]dec-8-yl]isonicotinonitrile

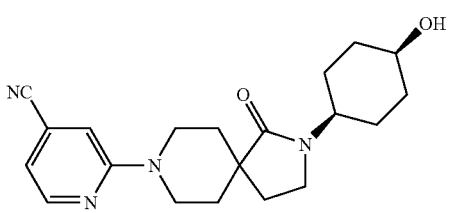

This compound was prepared using procedures analogous to those for Example 43. LCMS: (M+H)$^+$=355.2.

Example 55

8-[3-Fluoro-4-(trifluoromethyl)pyridin-2-yl]-2-(cis-4-hydroxycyclohexyl)-2,8-diazaspiro[4.5]decan-1-one

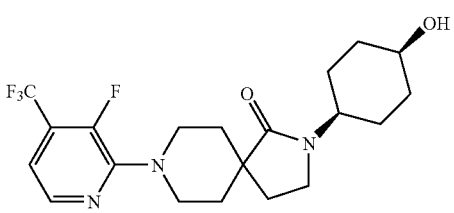

This compound was prepared using procedures analogous to those for Example 43. LCMS: (M+H)$^+$=416.2.

Example 56

2-(Cis-4-hydroxycyclohexyl)-8-pyrazin-2-yl-2,8-diazaspiro[4.5]decan-1-one

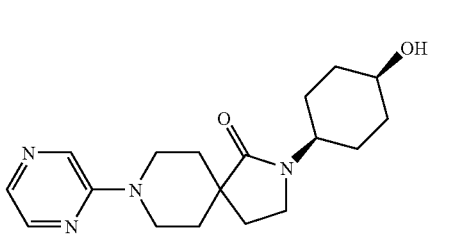

This compound was prepared using procedures analogous to those for Example 43. LCMS: (M+H)+=331.2.

Example 57

8-(6-Chloropyrazin-2-yl)-2-(cis-4-hydroxycyclohexyl)-2,8-diazaspiro[4.5]decan-1-one

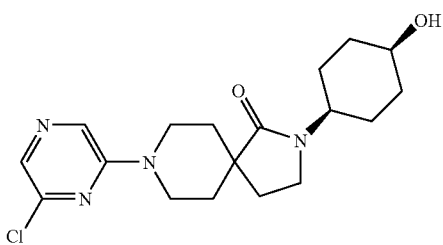

This compound was prepared using procedures analogous to those for Example 43. LCMS: (M+H)+=365.2/367.2.

Example 58

8-(3,6-Dimethylpyrazin-2-yl)-2-(cis-4-hydroxycyclohexyl)-2,8-diazaspiro[4.5]decan-1-one

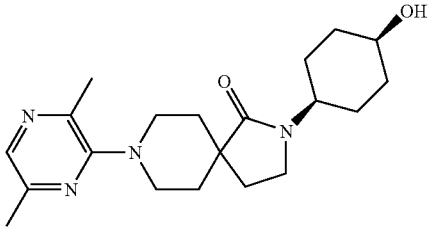

This compound was prepared using procedures analogous to those for Example 43. LCMS: (M+H)+=359.3.

Example 59

Methyl {6-[2-(cis-4-hydroxycyclohexyl)-1-oxo-2,8-diazaspiro[4.5]dec-8-yl]5-methylpyridin-3-yl}carbamate

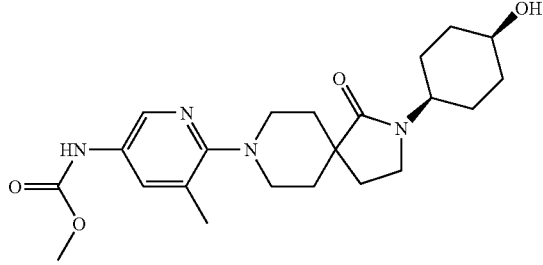

1) 2-(cis-4-Hydroxycyclohexyl)-8-(3-methyl-5-nitropyridin-2-yl)-2,8-diazaspiro[4.5]decan-1-one

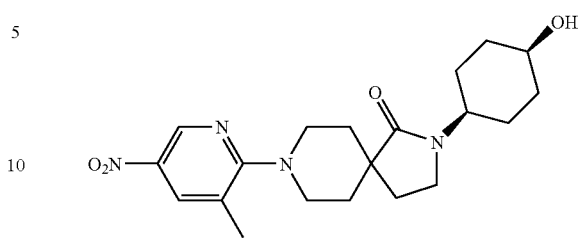

A mixture of 2-(cis-4-hydroxycyclohexyl)-2,8-diazaspiro[4.5]decan-1-one (0.10 g, 0.40 mmol), 2-chloro-3-methyl-5-nitropyridine (0.0718 g, 0.416 mmol) and potassium carbonate (0.11 g, 0.79 mmol) in N,N-dimethylformamide (2.0 mL) was heated at 90° C. overnight. After cooled to room temperature, the mixture was diluted with ethyl acetate, washed with water and brine. The organic phase was dried over Na$_2$SO$_4$, filtered, and concentrated. The residue was used directly in next step without further purification.

2) 8-(5-Amino-3-methylpyridin-2-yl)-2-(cis-4-hydroxycyclohexyl)-2,8-diazaspiro[4.5]decan-1-one

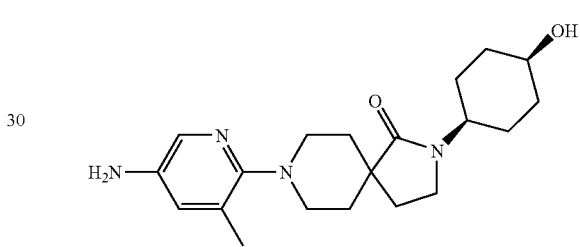

Pd/C (15 mg) was added to a solution of 2-(cis-4-hydroxycyclohexyl)-8-(3-methyl-5-nitropyridin-2-yl)-2,8-diazaspiro[4.5]decan-1-one in methanol (5.0 mL) under an atmosphere of nitrogen. The mixture was stirred under an atmosphere of hydrogen for 2 hrs, and filtered. The filtrate was concentrated to give 8-(5-amino-3-methylpyridin-2-yl)-2-(cis-4-hydroxycyclohexyl)-2,8-diazaspiro[4.5]decan-1-one.

3) Methyl {6-[2-(cis-4-hydroxycyclohexyl)-1-oxo-2,8-diazaspiro[4.5]dec-8-yl]-5-methylpyridin-3-yl}carbamate

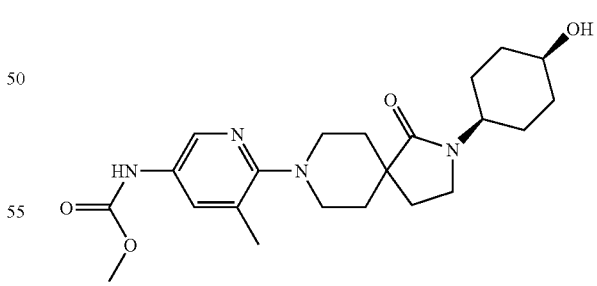

Methyl chloroformate (6.0 μL) was added to a mixture of 8-(5-amino-3-methylpyridin-2-yl)-2-(cis-4-hydroxycyclohexyl)-2,8-diazaspiro[4.5]decan-1-one (18.0 mg) and N,N-diisopropylethylamine (20.0 μL) in acetonitrile (1.0 mL). The mixture was stirred for 2 h, and was diluted with methanol. The resulting solution was purified by prep-HPLC under basic condition to afford methyl {6-[2-(cis-4-hydroxycyclohexyl)-1-oxo-2,8-diazaspiro[4.5]dec-8-yl]-5-methylpyridin-3-yl}carbamate. LCMS: (M+H)+=416.2.

Example 60

Ethyl {6-[2-(cis-4-hydroxycyclohexyl)-1-oxo-2,8-diazaspiro[4.5]dec-8-yl]5-methylpyridin-3-yl}carbamate

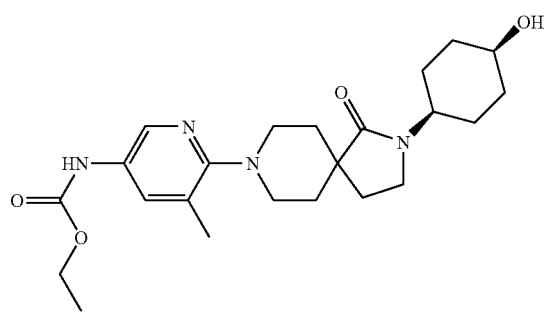

This compound was prepared using procedures analogous to those for Example 59. LCMS: (M+H)$^+$=431.3.

Example 61

Ethynyl {6-[2-(cis-4-hydroxycyclohexyl)-1-oxo-2,8-diazaspiro[4.5]dec-8-yl]5-methylpyridin-3-yl}carbamate

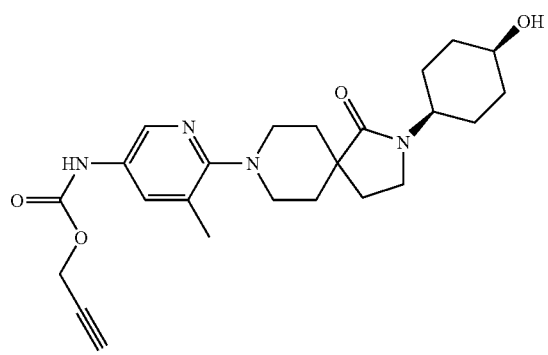

This compound was prepared using procedures analogous to those for Example 59. LCMS: (M+H)$^+$=441.2.

Example 62

Propyl {6-[2-(cis-4-hydroxycyclohexyl)-1-oxo-2,8-diazaspiro[4.5]dec-8-yl]-5-methylpyridin-3-yl}carbamate

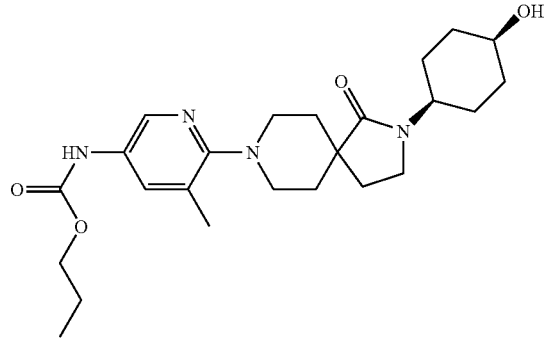

This compound was prepared using procedures analogous to those for Example 59. LCMS: (M+H)$^+$=445.30.

Example 63

N-{6-[2-(cis-4-hydroxycyclohexyl)-1-oxo-2,8-diazaspiro[4.5]dec-8-yl]-5-methylpyridin-3-yl}cyclopropanecarboxamide

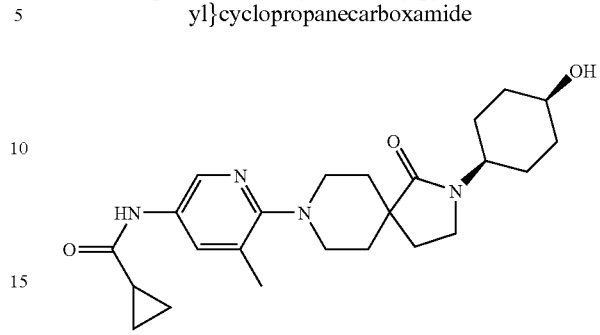

This compound was prepared using procedures analogous to those for Example 59. LCMS: (M+H)$^+$=427.20.

Example 64

2-(Cis-4-hydroxycyclohexyl)-8-[3-methyl-5-(2-oxopyrrolidin-1-yl)pyridin-2-yl]2,8-diazaspiro[4.5]decan-1-one

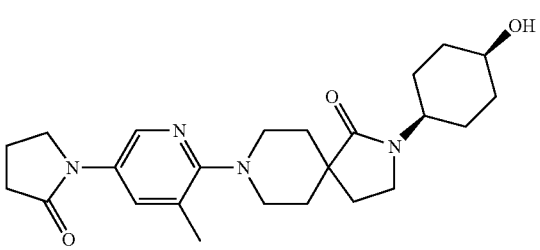

4-Bromobutanoyl chloride (13.0 μL) was added to a mixture of 8-(5-amino-3-methylpyridin-2-yl)-2-(cis-4-hydroxycyclohexyl)-2,8-diazaspiro[4.5]decan-1-one (18.0 mg) and 4-dimethylaminopyridine (14.5 mg) in dichloromethane (1.0 mL). The mixture was stirred for 3 h. Then potassium tert-butoxide in tetrahydrofuran (1.0 M, 0.20 mL) was added. The mixture was stirred for an additional hour. The solvent was evaporated. The residue was dissolved in methanol (1.8 mL), and purified by prep.-HPLC under basic condition to afford 2-(cis-4-hydroxycyclohexyl)-8-[3-methyl-5-(2-oxopyrrolidin-1-yl)pyridin-2-yl]-2,8-diazaspiro[4.5]decan-1-one. LCMS: (M+H)$^+$=427.20.

Example 65

2-(Cis-4-hydroxycyclohexyl)-8-[3-methyl-5-(2-oxo-1,3-oxazolidin-3-yl)pyridin-2-yl]-2,8-diazaspiro[4.5]decan-1-one

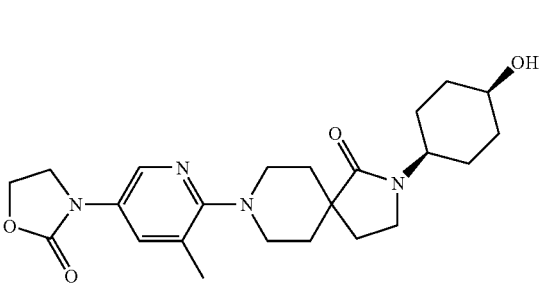

This compound was prepared using procedures analogous to those for Example 64. LCMS: (M+H)$^+$=429.25.

Example 66

2-(Cis-4-hydroxycyclohexyl)-8-[3-methyl-5-(2-oxopiperidin-1-yl)pyridin-2-yl]2,8-diazaspiro[4.5]decan-1-one

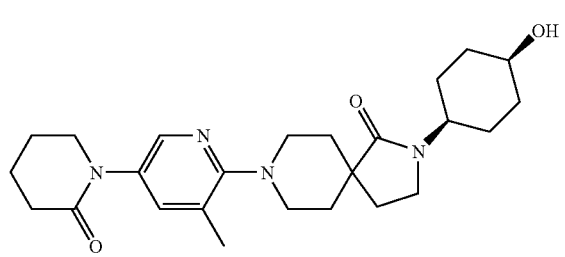

This compound was prepared using procedures analogous to those for Example 64. LCMS: (M+H)$^+$=441.30.

Example 67

2-(Cis-4-hydroxycyclohexyl)-8-[3-methyl-5-(2-oxo-1,3-oxazinan-3-yl)pyridin-2-yl]-2,8-diazaspiro[4.5]decan-1-one

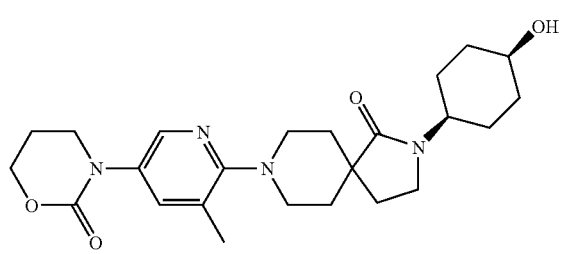

This compound was prepared using procedures analogous to those for Example 64. LCMS: (M+H)$^+$=443.20.

Example 68

Methyl {5-chloro-6-[2-(cis-4-hydroxycyclohexyl)-1-oxo-2,8-diazaspiro[4.5]dec-8-yl]pyridin-3-yl}carbamate

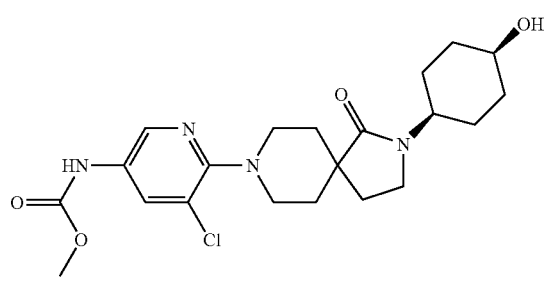

This compound was prepared using procedures analogous to those for Example 59. LCMS: (M+H)$^+$=437.2/439.2.

Example 69

Methyl {6-[2-(cis-4-hydroxycyclohexyl)-1-oxo-2,8-diazaspiro 14.51 dec-8-yl]pyridin-3-yl}carbamate

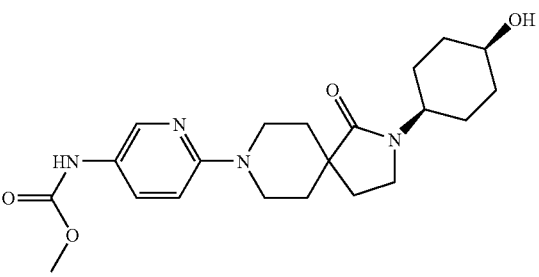

This compound was prepared using procedures analogous to those for Example 59. LCMS: (M+H)$^+$=403.3.

Example 70

Ethyl {5-chloro-6-[2-(cis-4-hydroxycyclohexyl)-1-oxo-2,8-diazaspiro[4.5]dec-8-yl]pyridin-3-yl}carbamate

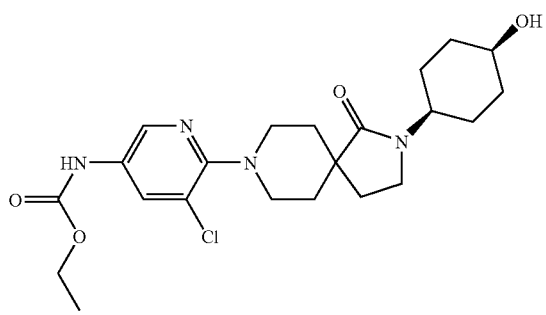

This compound was prepared using procedures analogous to those for Example 59. LCMS: (M+H)$^+$=451.2/453.2.

Example 71

Ethyl {6-[2-(cis-4-hydroxycyclohexyl)-1-oxo-2,8-diazaspiro[4.51]dec-8-yl]pyridin-3-yl}carbamate

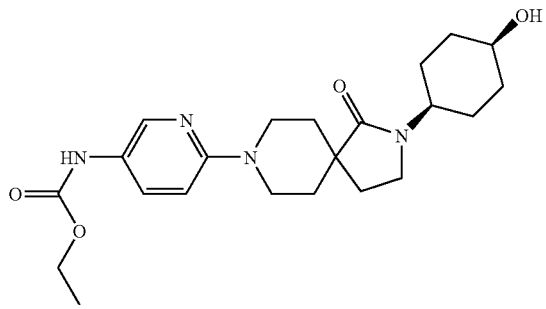

This compound was prepared using procedures analogous to those for Example 59. LCMS: (M+H)$^+$=417.2.

Example 72

Prop-2-yn-1-yl {5-chloro-6-[2-(cis-4-hydroxycyclohexyl)-1-oxo-2,8-diazaspiro[4.5]dec-8-yl]pyridin-3-yl}carbamate

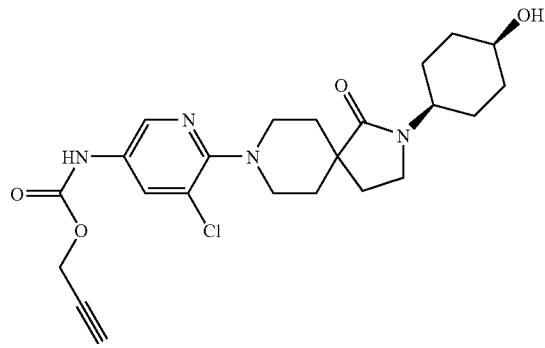

This compound was prepared using procedures analogous to those for Example 59. LCMS: $(M+H)^+=461.1/463.1$.

Example 73

Ethynyl {6-[2-(cis-4-hydroxycyclohexyl)-1-oxo-2,8-diazaspiro[4.5]dec-8-yl]pyridin-3-yl}carbamate

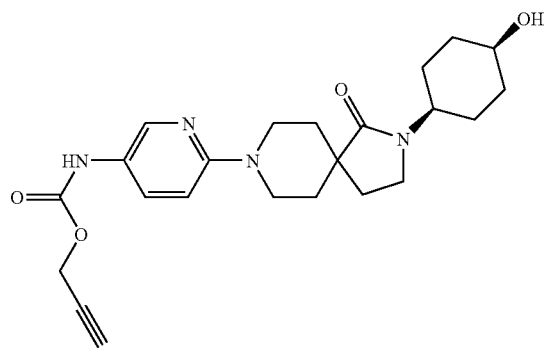

This compound was prepared using procedures analogous to those for Example 59. LCMS: $(M+H)^+=427.2$.

Example 74

Propyl {5-chloro-6-[2-(cis-4-hydroxycyclohexyl)-1-oxo-2,8-diazaspiro[4.5]dec-8-yl]pyridin-3-yl}carbamate

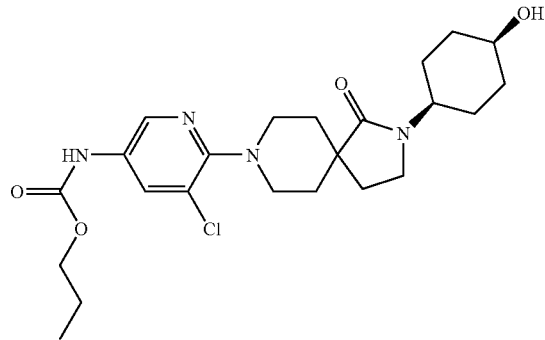

This compound was prepared using procedures analogous to those for Example 59. LCMS: $(M+H)^+=465.2/467.2$.

Example 75

Propyl {6-[2-(cis-4-hydroxycyclohexyl)-1-oxo-2,8-diazaspiro[4.5]dec-8-yl]pyridin-3-yl}carbamate

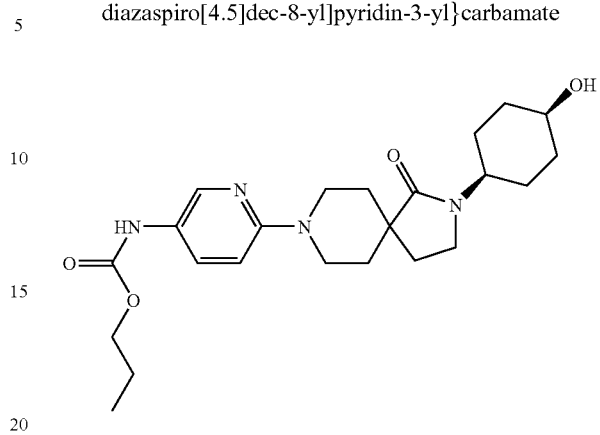

This compound was prepared using procedures analogous to those for Example 59. LCMS: $(M+H)^+=431.3$.

Example 76

3-Fluoro-4-[2-(cis-4-hydroxycyclohexyl)-1-oxo-2,8-diazaspiro[4.5]dec-8-yl]benzonitrile

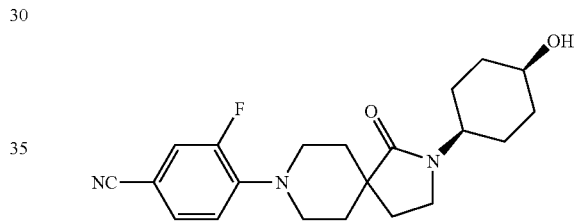

This compound was prepared using procedures analogous to those for Example 43. LCMS: $(M+H)^+=372.2$.

Example 77

4-Fluoro-3-[2-(cis-4-hydroxycyclohexyl)-1-oxo-2,8-diazaspiro 14.51 dec-8-yl]benzonitrile

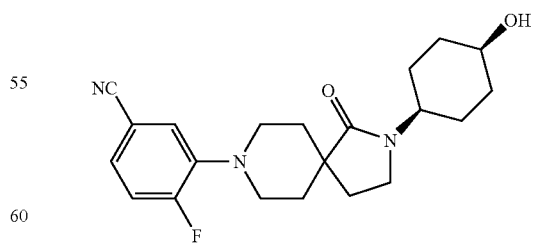

This compound was prepared using procedures analogous to those for Example 43. LCMS: $(M+H)^+=372.2$.

Example 78

3,5-Difluoro-4-[2-(cis-4-hydroxycyclohexyl)-1-oxo-2,8-diazaspiro[4.5]dec-8-yl]benzonitrile

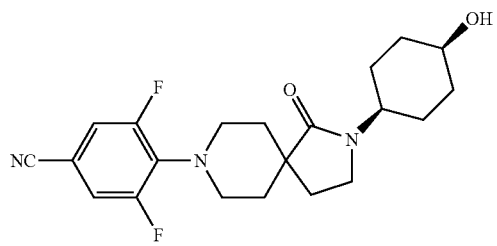

This compound was prepared using procedures analogous to those for Example 43. LCMS: (M+H)$^+$=390.2.

Example 79

3,4-Difluoro-5-[2-(cis-4-hydroxycyclohexyl)-1-oxo-2,8-diazaspiro[4.5]dec-8-yl]benzonitrile

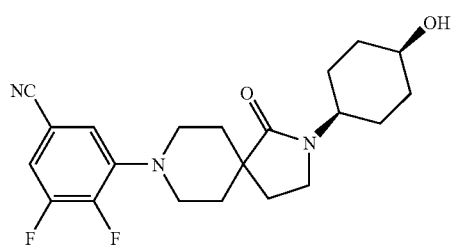

This compound was prepared using procedures analogous to those for Example 43. LCMS: (M+H)$^+$=390.2.

Example 80

3-{5-Chloro-6-[2-(cis-4-hydroxycyclohexyl)-1-oxo-2,8-diazaspiro[4.5]dec-8-yl]pyridin-3-yl}-N-methyl-benzamide

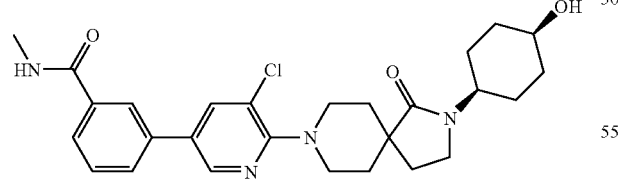

Potassium phosphate (0.017 g, 0.078 mmol) in water (0.10 mL) was added to a mixture of 8-(5-bromo-3-chloropyridin-2-yl)-2-(cis-4-hydroxycyclohexyl)-2,8-diazaspiro[4.5]decan-1-one (11.6 mg, 0.0262 mmol), 3-[(methylamino)carbonyl]phenylboronic acid (7.0 mg, 0.039 mmol) and tetrakis(triphenylphosphine)palladium(0) (0.9 mg, 0.0008 mmol) in 1,4-dioxane (0.78 mL). The resulting mixture was heated and stirred at 120° C. for 2 h. The mixture was diluted with ethyl acetate and washed with water and brine. The organic layer was dried over Na$_2$SO$_4$, filtered, concentrated under reduced pressure. The residue was purified by Prep-HPLC to afford the desired product. LCMS: (M+H)$^+$=497.1/499.1.

Example 81

8-(5-Bromo-2-fluorophenyl)-2-(cis-4-hydroxycyclohexyl)-2,8-diazaspiro[4.5]decan-1-one

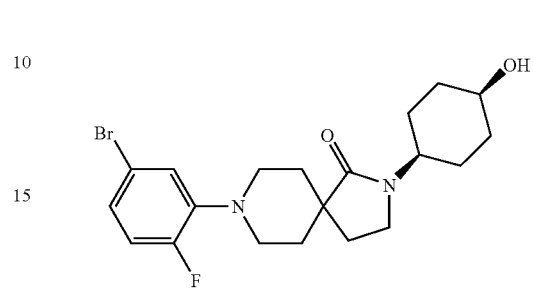

A mixture of 2-(cis-4-hydroxycyclohexyl)-2,8-diazaspiro[4.5]decan-1-one (0.50 g, 2.0 mmol), 4-bromo-1-fluoro-2-iodobenzene (0.894 g, 2.97 mmol), copper(I) iodide (0.0586 g, 0.308 mmol), potassium phosphate (1.26 g, 0.596 mmol) and 1,2-ethanediol (0.23 mL, 4.1 mmol) in 1-butanol (2.5 mL) was heated at 100° C. overnight. The reaction mixture was treated with water, extracted with ether. The combined organic layers were washed with brine, dried over MgSO$_4$ and filtered. The filtrate was concentrated under reduced pressure. The residue was purified on a silica gel column with ethyl acetate in hexane (gradient: 0 to 50%) to give the desired product (0.59 g, 70%). LCMS: (M+H)$^+$=425.0/427.0.

Example 82

8-{2-Fluoro-5-[6-(pyrrolidin-1-ylcarbonyl)pyridin-3-yl]phenyl}-2-(cis-4-hydroxycyclohexyl)-2,8-diazaspiro[4.5]decan-1-one

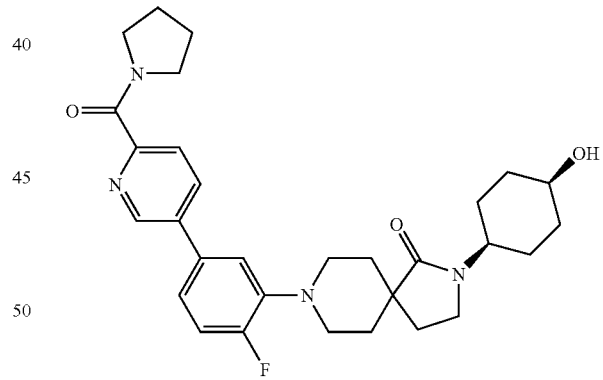

1) 5-Bromopyridine-2-carbonyl chloride

To a mixture of 5-bromopyridine-2-carboxylic acid (2.5 g, 12 mmol) in methylene chloride (10.0 mL) was added oxalyl chloride (1.6 mL, 18 mmol), followed by N,N-dimethylformamide (0.020 mL, 0.26 mmol). After stirred at RT for 2 h, the mixture was evaporated under reduced pressure. The residue was the acid chloride which was used directly in next step reaction.

2) 5-Bromo-2-(pyrrolidin-1-ylcarbonyl)pyridine

The above acid chloride was dissolved in methylene chloride (20.0 mL). To the solution was added a mixture of pyrrolidine (1.2 mL, 15 mmol) and triethylamine (5.2 mL, 37 mmol) in methylene chloride (5 mL). The reaction mixture was stirred at room temperature for 30 min, quenched with aqueous sodium bicarbonate. The mixture was extracted with methylene chloride (3×20 mL). The combined organic layers were washed with brine, dried over MgSO$_4$, and filtered. The filtrate was evaporated under reduced pressure. The residue was purified on a silica gel column with ethyl acetate in hexane (gradient: 0 to 60%) to yield the desired product.

3) 2-(Pyrrolidin-1-ylcarbonyl)-5-(4,4,5,5-tetramethyl-1,3,2-dioxaborolan-2-yl)pyridine To a mixture of 5-bromo-2-(pyrrolidin-1-ylcarbonyl)pyridine (1.0 g, 4.1 mmol) and 4,4,5,5,4',4',5',5'-octamethyl-[2,2']bi[[1,3,2]dioxaborolanyl](1.2 g, 4.6 mol) in 1,4-dioxane (10.0 mL) was added [1,1'-bis(diphenylphosphino)ferrocene]dichloropalladium(II), complex with dichloromethane (1:1) (0.2 g, 0.2 mol), potassium acetate (1.2 g, 12 mmol), and 1,1'-bis(diphenylphosphino)ferrocene (0.1 g, 0.2 mmol) under an atmosphere of nitrogen. The reaction mixture was stirred at 80° C. overnight. After cooled to room temperature, the mixture was filtered through a pad of celite, washed with ethyl acetate, and concentrated. The residue was purified on a silica gel column with ethyl acetate in hexane gradient: (0 to 40%) to afford the desired product.

4) 8-{2-Fluoro-5-[6-(pyrrolidin-1-ylcarbonyl)pyridin-3-yl]phenyl}-2-(cis-4-hydroxycyclohexyl)-2,8-diazaspiro[4.5]decan-1-one Potassium phosphate (0.017 g, 0.078 mmol) in water (0.10 mL) was added to a mixture of 8-(5-bromo-2-fluorophenyl)-2-(cis-4-hydroxycyclohexyl)-2,8-diazaspiro[4.5]decan-1-one (15.0 mg, 0.0353 mmol), 2-(pyrrolidin-1-ylcarbonyl)-5-(4,4,5,5-tetramethyl-1,3,2-dioxaborolan-2-yl)pyridine (16 mg, 0.053 mmol), and tetrakis(triphenylphosphine)palladium(0) (1.0 mg, 0.001 mmol) in 1,4-dioxane (0.30 mL). The resulting mixture was heated and stirred at 120° C. for 20 min. The mixture was filtered. The filtrate was diluted with methanol, and was purified by mass-guided reverse phase chromatography to afford the desired product. LCMS: (M+H)$^+$= 521.2.

Example 83

8-(5-[6-(Azetidin-1-ylcarbonyl)pyridin-3-yl]2-fluorophenyl)-2-(cis-4-hydroxycyclohexyl)-2,8-diazaspiro[4,5]decan-1-one

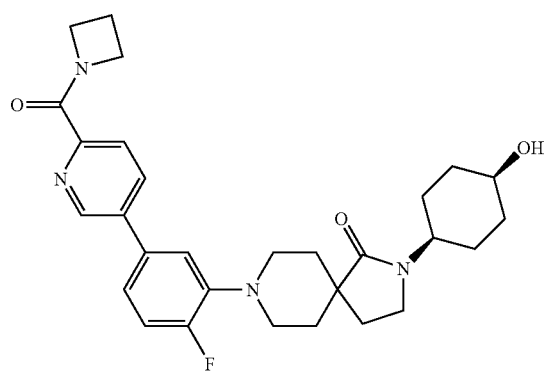

This compound was prepared using procedures analogous to those for Example 82. LCMS: (M+H)$^+$=507.1.

Example 84

4'-Fluoro-3'-[2-(cis-4-hydroxycyclohexyl)-1-oxo-2,8-diazaspiro[4.5]dec-8-yl]biphenyl-4-carboxamide

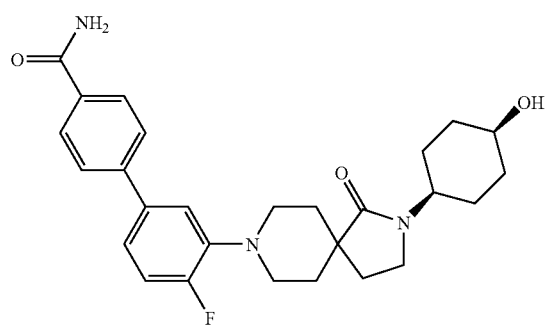

This compound was prepared using procedures analogous to those for Example 82. LCMS: (M+H)$^+$=466.0.

Example 85

4'-Fluoro-3'-[2-(cis-4-hydroxycyclohexyl)-1-oxo-2,8-diazaspiro[4.5]dec-8-yl]N-methylbiphenyl-4-carboxamide

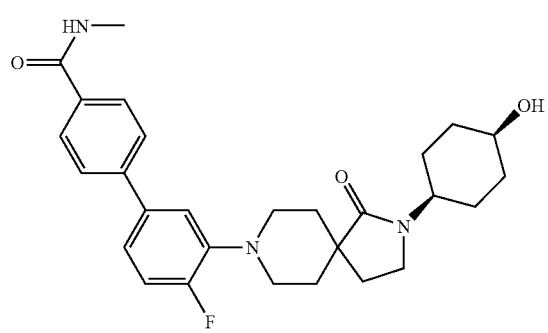

This compound was prepared using procedures analogous to those for Example 82. LCMS: (M+H)$^+$=480.1.

Example 86

4'-Fluoro-3'-[2-(cis-4-hydroxycyclohexyl)-1-oxo-2,8-diazaspiro[4.5]dec-8-yl]biphenyl-3-carboxamide

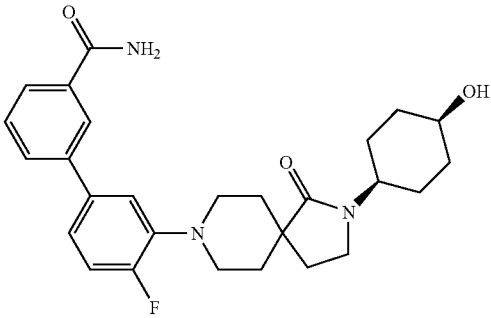

This compound was prepared using procedures analogous to those for Example 82. LCMS: (M+H)$^+$=466.1.

Example 87

4'-Fluoro-3'-[2-(cis-4-hydroxycyclohexyl)-1-oxo-2,8-diazaspiro[4.5]dec-8-yl]-N,N-dimethylbiphenyl-3-carboxamide

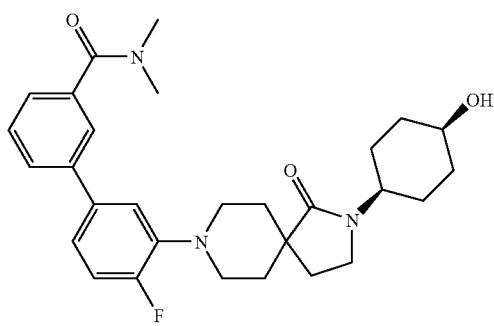

This compound was prepared using procedures analogous to those for Example 82. LCMS: $(M+H)^+=494.1$.

Example 88

4'-Fluoro-3'-[2-(cis-4-hydroxycyclohexyl)-1-oxo-2,8-diazaspiro[4.5]dec-8-yl]-N-isopropylbiphenyl-3-carboxamide

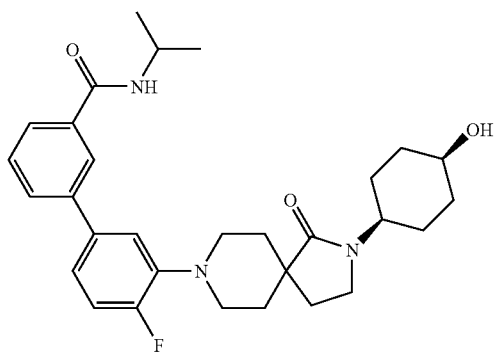

This compound was prepared using procedures analogous to those for Example 82. LCMS: $(M+H)^+=508.2$.

Example 89

N-Ethyl-5-{4-fluoro-3-[2-(cis-4-hydroxycyclohexyl)-1-oxo-2,8-diazaspiro[4.5]dec-8-yl]phenyl}pyridine-2-carboxamide

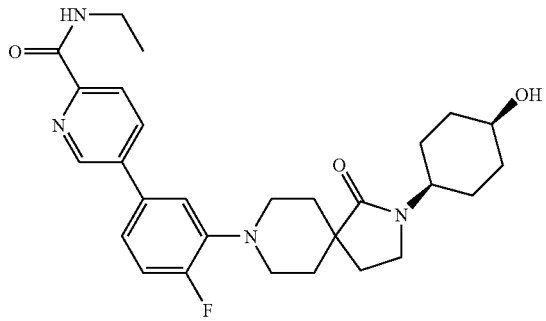

This compound was prepared using procedures analogous to those for Example 82. LCMS: $(M+H)^+=495.1$.

Example 90

8-(2-Fluoro-5-pyridin-4-ylphenyl)-2-(cis-4-hydroxycyclohexyl)-2,8-diazaspiro[4.5]decan-1-one

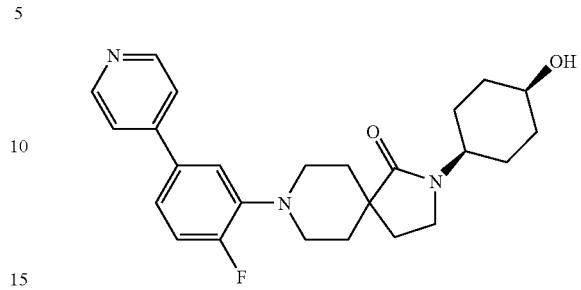

This compound was prepared using procedures analogous to those for Example 82. LCMS: $(M+H)^+=424.1$.

Example 91

8-[2-Fluoro-5-(1-methyl-1H-pyrazol-4-yl)phenyl]2-(cis-4-hydroxycyclohexyl)-2,8-diazaspiro[4.5]decan-1-one

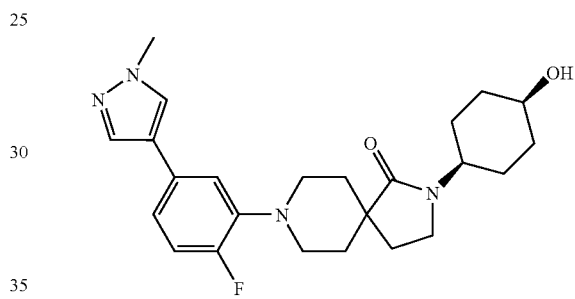

This compound was prepared using procedures analogous to those for Example 82. LCMS: $(M+H)^+=427.1$.

Example A

Enzymatic Assay of 11βHSD1

All in vitro assays were performed with clarified lysates as the source of 11βHSD1 activity. HEK-293 transient transfectants expressing an epitope-tagged version of full-length human 11βHSD1 were harvested by centrifugation. Roughly $2\times10^7$ cells were resuspended in 40 mL of lysis buffer (25 mM Tris-HCl, pH 7.5, 0.1 M NaCl, 1 mM $MgCl_2$ and 250 mM sucrose) and lysed in a microfluidizer. Lysates were clarified by centrifugation and the supernatants were aliquoted and frozen.

Inhibition of 11βHSD1 by test compounds was assessed in vitro by a Scintillation Proximity Assay (SPA). Dry test compounds were dissolved at 5 mM in DMSO. These were diluted in DMSO to suitable concentrations for the SPA assay. 0.8 μL of 2-fold serial dilutions of compounds were dotted on 384 well plates in DMSO such that 3 logs of compound concentration were covered. 20 μL of clarified lysate was added to each well. Reactions were initiated by addition of 20 μL of substrate-cofactor mix in assay buffer (25 mM Tris-HCl, pH 7.5, 0.1 M NaCl, 1 mM $MgCl_2$) to final concentrations of 400 μM NADPH, 25 nM $^3$H-cortisone and 0.007% Triton X-100. Plates were incubated at 37° C. for one hour. Reactions were quenched by addition of 40 μL of anti-mouse coated SPA beads that had been pre-incubated with 10 μM carbenoxolone and a cortisol-specific monoclonal antibody. Quenched plates were incubated for a minimum of 30 minutes at RT prior to reading on a Topcount scintillation counter. Controls with no lysate, inhibited lysate, and with no mAb were run routinely. Roughly 30% of input cortisone is reduced by 11βHSD1 in the uninhibited reaction under these conditions.

Test compounds having an $IC_{50}$ value less than about 20 μM according to this assay were considered active.

Example B

Cell-Based Assays for HSD Activity

Peripheral blood mononuclear cells (PBMCs) were isolated from normal human volunteers by Ficoll density centrifugation. Cells were plated at $4 \times 10^5$ cells/well in 200 μL of AIM V (Gibco-BRL) media in 96 well plates. The cells were stimulated overnight with 50 ng/ml recombinant human IL-4 (R&D Systems). The following morning, 200 nM cortisone (Sigma) was added in the presence or absence of various concentrations of compound. The cells were incubated for 48 hours and then supernatants were harvested. Conversion of cortisone to cortisol was determined by a commercially available ELISA (Assay Design).

Test compounds having an $IC_{50}$ value less than about 20 μM according to this assay were considered active.

Various modifications of the invention, in addition to those described herein, will be apparent to those skilled in the art from the foregoing description. Such modifications are also intended to fall within the scope of the appended claims. Each reference, including all patent, patent applications, and publications, cited in the present application is incorporated herein by reference in its entirety.

What is claimed is:

1. A compound of Formula I:

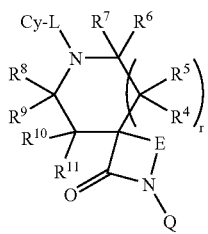

I or pharmaceutically acceptable salt thereof, wherein:

Cy is aryl, heteroaryl, cycloalkyl, or heterocycloalkyl, each optionally substituted with 1, 2, 3, 4 or 5 —W—X—Y—Z;

L is absent, CO or $SO_2$;

Q is —$(CR^1R^2)_m$-A;

A is cycloalkyl, heterocycloalkyl or heteroaryl, each optionally substituted with 1, 2, 3, 4 or 5 —W'—X'—Y'—Z';

E is —$(CR^{3a}R^{3b})_{n1}$—, $(CR^{3a}R^{3b})_{n2}OCO$—, —$(CR^{3a}R^{3b})_{n2}SO$—, —$(CR^{3a}R^{3b})_{n2}SO_2$—, —$(CR^{3a}R^{3b})_{n2}NR^{3c}$—, $R^1$ and $R^2$ are independently selected from H and $C_{1-8}$ alkyl;

$R^{3a}$ and $R^{3b}$ are independently selected from H, halo, $C_{1-4}$ alkyl, $C_{1-4}$ haloalkyl, $C_{2-4}$ alkenyl, and $C_{2-4}$ alkynyl;

$R^{3c}$ is H, $C_{1-4}$ alkyl, $C_{1-4}$ haloalkyl, $C_{2-4}$ alkenyl, $C_{2-4}$ alkynyl, or CO—($C_{1-4}$ alkyl);

$R^4$, $R^5$, $R^6$, $R^7$, $R^8$, $R^9$, $R^{10}$ and $R^{11}$ are independently selected from H, OC(O)$R^{a'}$, OC(O)O$R^{b'}$, C(O)O$R^{b'}$, OC(O)NR$^{c'}$R$^{d'}$, NR$^{c'}$R$^{d'}$, NR$^{c'}$C(O)$R^{a'}$, NR$^{c'}$C(O)O$R^{b'}$, S(O)$R^{a'}$, S(O)NR$^{c'}$R$^{d'}$, S(O)$_2$$R^{a'}$, S(O)$_2$NR$^{c'}$R$^{d'}$, O$R^{b'}$, S$R^{b'}$, halo, $C_{1-10}$ alkyl, $C_{1-10}$ haloalkyl, $C_{2-10}$ alkenyl, $C_{2-10}$ alkynyl, aryl, cycloalkyl, heteroaryl, heterocycloalkyl, arylalkyl, heteroarylalkyl, cycloalkylalkyl, and heterocycloalkylalkyl, wherein said $C_{1-10}$ alkyl, $C_{1-10}$ haloalkyl, $C_{2-10}$ alkenyl, $C_{2-10}$ alkynyl, aryl, cycloalkyl, heteroaryl, heterocycloalkyl, arylalkyl, heteroarylalkyl, cycloalkylalkyl or heterocycloalkylalkyl is optionally substituted by 1, 2, or 3 $R^{14}$;

or $R^4$ and $R^5$ together with the carbon atom to which they are attached form a 3-14 membered cycloalkyl or heterocycloalkyl group which is optionally substituted by $R^{14}$;

or $R^6$ and $R^7$ together with the carbon atom to which they are attached form a 3-14 membered cycloalkyl or heterocycloalkyl group which is optionally substituted by $R^{14}$;

or $R^8$ and $R^9$ together with the carbon atom to which they are attached form a 3-14 membered cycloalkyl or heterocycloalkyl group which is optionally substituted by $R^{14}$;

or $R^{10}$ and $R^{11}$ together with the carbon atom to which they are attached form a 3-14 membered cycloalkyl or heterocycloalkyl group which is optionally substituted by $R^{14}$;

or $R^4$ and $R^6$ together with the carbon atom to which they are attached form a 3-7 membered fused cycloalkyl group or 3-7 membered fused heterocycloalkyl group which is optionally substituted by $R^{14}$;

or $R^6$ and $R^8$ together with the carbon atom to which they are attached form a 3-7 membered fused cycloalkyl group or 3-7 membered fused heterocycloalkyl group which is optionally substituted by $R^{14}$;

or $R^4$ and $R^9$ together form a $C_{1-3}$ alkylene bridge which is optionally substituted by $R^{14}$;

or $R^4$ and $R^{10}$ together form a $C_{1-3}$ alkylene bridge which is optionally substituted by $R^{14}$;

or $R^6$ and $R^{10}$ together form a $C_{1-3}$ alkylene bridge which is optionally substituted by $R^{14}$;

or $R^9$ and $R^{10}$ together form a $C_{1-3}$ alkylene bridge which is optionally substituted by $R^{14}$;

$R^{14}$ is halo, $C_{1-4}$ alkyl, $C_{1-4}$ haloalkyl, aryl, cycloalkyl, heteroaryl, heterocycloalkyl, CN, $NO_2$, $OR^{a'}$, $SR^{a'}$, C(O)$R^{b'}$, C(O)NR$^{c'}$R$^{d'}$, C(O)O$R^{a'}$, OC(O)$R^{b'}$, OC(O)NR$^{c'}$R$^{d'}$, NR$^{c'}$R$^{d'}$, NR$^{c'}$C(O)$R^{d'}$, NR$^{c'}$C(O)O$R^{a'}$, S(O)$R^{b'}$, S(O)NR$^{c'}$R$^{d'}$, S(O)$_2$$R^{b'}$, or S(O)$_2$NR$^{c'}$R$^{d'}$;

W, W' and W" are independently selected from absent, $C_{1-6}$ alkylenyl, $C_{2-6}$ alkenylenyl, $C_{2-6}$ alkynylenyl, O, S, $NR^e$, CO, COO, $CONR^e$, SO, $SO_2$, $SONR^e$, and $NR^eCONR^f$, wherein said $C_{1-6}$ alkylenyl, $C_{2-6}$ alkenylenyl, $C_{2-6}$ alkynylenyl are each optionally substituted by 1, 2 or 3 substituents independently selected from halo, OH, $C_{1-4}$ alkoxy, $C_{1-4}$ haloalkoxy, amino, $C_{1-4}$ alkylamino, and $C_{2-8}$ dialkylamino;

X, X' and X" are independently selected from absent, $C_{1-6}$ alkylenyl, $C_{2-6}$ alkenylenyl, $C_{2-6}$ alkynylenyl, aryl, cycloalkyl, heteroaryl, and heterocycloalkyl, wherein said $C_{1-6}$ alkylenyl, $C_{2-6}$ alkenylenyl, $C_{2-6}$ alkynylenyl, aryl, cycloalkyl, heteroaryl, or heterocycloalkyl is optionally substituted by one or more substituents independently selected from halo, $C_{1-6}$ alkyl, oxo, CN, $NO_2$, OH, $C_{1-4}$ alkoxy, $C_{1-4}$ haloalkoxy, amino, $C_{1-4}$ alkylamino, and $C_{2-8}$ dialkylamino;

Y, Y' and Y" are independently selected from absent, $C_{1-6}$ alkylenyl, $C_{2-6}$ alkenylenyl, $C_{2-6}$ alkynylenyl, O, S, $NR^e$, CO, COO, $CONR^e$, SO, $SO_2$, $SONR^e$, and $NR^eCONR^f$, wherein said $C_{1-6}$ alkylenyl, $C_{2-6}$ alkenylenyl, $C_{2-6}$ alkynylenyl are each optionally substituted by 1, 2 or 3 substituents independently selected from halo, OH, $C_{1-4}$ alkoxy, $C_{1-4}$ haloalkoxy, amino, $C_{1-4}$ alkylamino, and $C_{2-8}$ dialkylamino;

Z, Z' and Z" are independently selected from H, halo, CN, $NO_2$, OH, $C_{1-4}$ alkoxy, $C_{1-4}$ haloalkoxy, amino, $C_{1-4}$ alkylamino, $C_{2-8}$ dialkylamino, $C_{1-6}$ alkyl, $C_{2-6}$ alkenyl, $C_{2-6}$ alkynyl, aryl, cycloalkyl, heteroaryl, and heterocycloalkyl, wherein said $C_{1-6}$ alkyl, $C_{2-6}$ alkenyl, $C_{2-6}$ alkynyl, aryl, cycloalkyl, heteroaryl, or heterocycloalkyl is optionally substituted by 1, 2 or 3 substituents independently selected from halo, oxo, $C_{1-6}$ alkyl, $C_{2-6}$ alkenyl, $C_{2-6}$ alkynyl, $C_{1-4}$ haloalkyl, aryl, cycloalkyl, heteroaryl, heterocycloalkyl, halosulfanyl, CN, $NO_2$, $OR^a$, $SR^a$, $C(O)R^b$, $C(O)NR^cR^d$, $C(O)OR^a$, $OC(O)R^b$, $OC(O)NR^cR^d$, $NR^cR^d$, $NR^cC(O)R^d$, $NR^cC(O)OR^a$, $NR^eS(O)_2R^b$, $C(=NR^i)NR^cR^d$, $NR^cC(=NR^i)NR^cR^d$, $S(O)R^b$, $S(O)NR^cR^d$, $S(O)_2R^b$, and $S(O)_2NR^cR^d$;

wherein two —W—X—Y—Z attached to the same atom optionally form a 3-20 membered cycloalkyl or heterocycloalkyl group, each optionally substituted by 1, 2 or 3 —W"—X"—Y"—Z";

wherein two attached to the same atom optionally form a 3-20 membered cycloalkyl or heterocycloalkyl group, each optionally substituted by 1, 2 or 3 —W"—X"—Y"—Z";

wherein —W—X—Y—Z is other than H;
wherein —W'—X'—Y'—Z' is other than H;
wherein —W"—X"—Y"—Z" is other than H;

$R^a$ and $R^{a'}$ are independently selected from H, $C_{1-6}$ alkyl, $C_{1-6}$ haloalkyl, $C_{2-6}$ alkenyl, $C_{2-6}$ alkynyl, aryl, cycloalkyl, heteroaryl, and heterocycloalkyl, wherein said $C_{1-6}$ alkyl, $C_{1-6}$ haloalkyl, $C_{2-6}$ alkenyl, $C_{2-6}$ alkynyl, aryl, cycloalkyl, heteroaryl, or heterocycloalkyl is optionally substituted with H, OH, amino, halo, $C_{1-6}$ alkyl, $C_{1-6}$ haloalkyl, aryl, arylalkyl, heteroaryl, heteroarylalkyl, cycloalkyl, or heterocycloalkyl;

$R^b$ and $R^{b'}$ are independently selected from H, $C_{1-6}$ alkyl, $C_{1-6}$ haloalkyl, $C_{2-6}$ alkenyl, $C_{2-6}$ alkynyl, aryl, cycloalkyl, heteroaryl, heterocycloalkyl, arylalkyl, heteroarylalkyl, cycloalkylalkyl, and heterocycloalkylalkyl, wherein said $C_{1-6}$ alkyl, $C_{1-6}$ haloalkyl, $C_{2-6}$ alkenyl, $C_{2-6}$ alkynyl, aryl, cycloalkyl, heteroaryl, heterocycloalkyl, arylalkyl, heteroarylalkyl, cycloalkylalkyl, or heterocycloalkylalkyl is optionally substituted with H, OH, amino, halo, $C_{1-6}$ alkyl, $C_{1-6}$ haloalkyl, $C_{1-6}$ haloalkyl, aryl, arylalkyl, heteroaryl, heteroarylalkyl, cycloalkyl or heterocycloalkyl;

$R^c$ and $R^d$ are independently selected from H, $C_{1-10}$ alkyl, $C_{1-6}$ haloalkyl, $C_{2-6}$ alkenyl, $C_{2-6}$ alkynyl, aryl, heteroaryl, cycloalkyl, heterocycloalkyl, arylalkyl, heteroarylalkyl, cycloalkylalkyl, and heterocycloalkylalkyl, wherein said $C_{1-10}$ alkyl, $C_{1-6}$ haloalkyl, $C_{2-6}$ alkenyl, $C_{2-6}$ alkynyl, aryl, heteroaryl, cycloalkyl, heterocycloalkyl, arylalkyl, heteroarylalkyl, cycloalkylalkyl, or heterocycloalkylalkyl is optionally substituted with H, OH, amino, halo, $C_{1-6}$ alkyl, $C_{1-6}$ haloalkyl, $C_{1-6}$ haloalkyl, aryl, arylalkyl, heteroaryl, heteroarylalkyl, cycloalkyl or heterocycloalkyl;

or $R^c$ and $R^d$ together with the N atom to which they are attached form a 4-, 5-, 6- or 7-membered heterocycloalkyl group;

$R^{c'}$ and $R^{d'}$ are independently selected from H, $C_{1-10}$ alkyl, $C_{1-6}$ haloalkyl, $C_{2-6}$ alkenyl, $C_{2-6}$ alkynyl, aryl, heteroaryl, cycloalkyl, heterocycloalkyl, arylalkyl, heteroarylalkyl, cycloalkylalkyl, and heterocycloalkylalkyl, wherein said $C_{1-40}$ alkyl, $C_{1-6}$ haloalkyl, $C_{2-6}$ alkenyl, $C_{2-6}$ alkynyl, aryl, heteroaryl, cycloalkyl, heterocycloalkyl, arylalkyl, heteroarylalkyl, cycloalkylalkyl, or heterocycloalkylalkyl is optionally substituted with H, OH, amino, halo, $C_{1-6}$ alkyl, $C_{1-6}$ haloalkyl, $C_{1-6}$ haloalkyl, aryl, arylalkyl, heteroaryl, heteroarylalkyl, cycloalkyl or heterocycloalkyl;

or $R^{c'}$ and $R^{d'}$ together with the N atom to which they are attached form a 4-, 5-, 6- or 7-membered heterocycloalkyl group;

$R^e$ and $R^f$ are independently selected from H, $C_{1-10}$ alkyl, $C_{1-6}$ haloalkyl, $C_{2-6}$ alkenyl, $C_{2-6}$ alkynyl, aryl, heteroaryl, cycloalkyl, heterocycloalkyl, arylalkyl, heteroarylalkyl, cycloalkylalkyl, heterocycloalkylalkyl, wherein said $C_{1-10}$ alkyl, $C_{1-6}$ haloalkyl, $C_{2-6}$ alkenyl, $C_{2-6}$ alkynyl, aryl, heteroaryl, cycloalkyl, heterocycloalkyl, arylalkyl, heteroarylalkyl, cycloalkylalkyl, or heterocycloalkylalkyl is optionally substituted with H, OH, amino, halo, $C_{1-6}$ alkyl, $C_{1-6}$ haloalkyl, $C_{1-6}$ haloalkyl, aryl, arylalkyl, heteroaryl, heteroarylalkyl, cycloalkyl or heterocycloalkyl;

or $R^e$ and $R^f$ together with the N atom to which they are attached form a 4-, 5-, 6- or 7-membered heterocycloalkyl group;

$R^i$ is H, CN, or $NO_2$;
m is 0, 1, 2 or 3;
n1 is 1, 2, 3 or 4;
n2 is 0, 1, 2, 3 or 4;
and
r is 1 or 2.

2. The compound of claim 1, or pharmaceutically acceptable salt thereof, wherein Cy is aryl or heteroaryl, each optionally substituted with 1, 2, 3, 4 or 5 —W—X—Y—Z.

3. The compound of claim 1, or pharmaceutically acceptable salt thereof, wherein Cy is aryl or heteroaryl, each optionally substituted with 1, 2, 3, 4 or 5 —W—X—Y—Z wherein W is O or absent, X is absent, and Y is absent.

4. The compound of claim 1, or pharmaceutically acceptable salt thereof, wherein Cy is phenyl, naphthyl, pyridyl, pyrimidinyl, triazinyl, furanyl, thiazolyl, pyrazinyl, purinyl, quinazolinyl, quinolinyl, isoquinolinyl, pyrrolo[2,3-d]pyrimidinyl, or 1,3-benzothiazolyl, each optionally substituted with 1, 2, 3, 4 or 5 —W—X—Y—Z.

5. The compound of claim 1, or pharmaceutically acceptable salt thereof, wherein Cy is phenyl, naphthyl, pyridyl, pyrimidinyl, triazinyl, furanyl thiazolyl, pyrazinyl, purinyl, quinazolinyl, quinolinyl, isoquinolinyl, pyrrolo[2,3-d]pyrimidinyl, or 1,3-benzothiazolyl, each optionally substituted by 1, 2, 3 or 4 halo, CN, $NO_2$, $C_{1-4}$ alkoxy, heteroaryloxy, $C_{2-6}$ alkynyl, $C_{1-4}$ haloalkoxy, $NR^cC(O)R^d$, $NR^cC(O)OR^a$, $C(O)NR^cR^d$, $NR^cR^d$, $NR^cS(O)_2R^b$, $C_{1-4}$ haloalkyl, $C_{1-6}$ alkyl, heterocycloalkyl, aryl or heteroaryl, wherein each of said $C_{1-6}$ alkyl, aryl or heteroaryl is optionally substituted by 1, 2 or 3 halo, $C_{1-6}$ alkyl, $C_{1-4}$ haloalkyl, CN, $NO_2$, $OR^a$, $SR^a$, $C(O)NR^cR^d$, $NR^cC(O)R^d$ or $COOR^a$.

6. The compound of claim 1, or pharmaceutically acceptable salt thereof, wherein Cy is phenyl, pyridyl, pyrimidinyl, pyrazinyl or 1,3-benzothiazolyl, each optionally substituted by 1, 2, 3, 4 or 5 —W—X—Y—Z.

7. The compound of claim 1, or pharmaceutically acceptable salt thereof, wherein Cy is phenyl, pyridyl, pyrimidinyl, pyrazinyl or 1,3-benzothiazolyl, each optionally substituted by 1, 2, 3 or 4 halo, CN, $NO_2$, $C_{1-4}$ alkoxy, heteroaryloxy, $C_{2-6}$ alkynyl, $C_{1-4}$ haloalkoxy, $NR^cC(O)R^d$, $NR^cC(O)OR^a$, $C(O)NR^cR^d$, $NR^cR^d$, $NR^cS(O)_2R^b$, $C_{1-4}$ haloalkyl, $C_{1-6}$ alkyl, heterocycloalkyl, aryl or heteroaryl, wherein each of said $C_{1-6}$ alkyl, aryl or heteroaryl is optionally substituted by 1, 2 or 3 halo, $C_{1-6}$ alkyl, $C_{1-4}$ haloalkyl, CN, $NO_2$, $OR^a$, $SR^a$, $C(O)NR^cR^d$, $NR^cC(O)R^d$ or $COOR^a$.

8. The compound of claim 1, or pharmaceutically acceptable salt thereof, wherein Cy is phenyl, pyridyl, pyrimidinyl, pyrazinyl or 1,3-benzothiazolyl, each optionally substituted by 1, 2, 3 or 4 halo, CN, $C_{1-4}$ haloalkyl, $C_{1-6}$ alkyl or aryl, wherein each of said $C_{1-6}$ alkyl or aryl is optionally substituted by 1, 2 or 3 halo, $C_{1-6}$ alkyl, $C_{1-4}$ haloalkyl or CN.

9. The compound of claim 1, or pharmaceutically acceptable salt thereof, wherein Cy is cycloalkyl or heterocycloalkyl, each optionally substituted by 1, 2, 3, 4 or 5 —W—X—Y—Z.

10. The compound of claim 1, or pharmaceutically acceptable salt thereof, wherein Cy is cycloalkyl or heterocycloalkyl, each optionally substituted by 1, 2, 3, 4 or 5 —W—X—Y—Z wherein W is O or absent, X is absent, and Y is absent.

11. The compound of claim 1, or pharmaceutically acceptable salt thereof, wherein Cy is cyclopropyl, cyclobutyl, cyclopentyl, cyclohexyl, cycloheptyl, adamantyl, aziridinyl, azetidinyl, pyrrolidine, piperidinyl, piperizinyl or morpholinyl, each optionally substituted by 1, 2, 3, 4 or 5 —W—X—Y—Z.

12. The compound of claim 1, or pharmaceutically acceptable salt thereof, wherein Cy is cyclopropyl, cyclobutyl, cyclopentyl, cyclohexyl, cycloheptyl, adamantyl, aziridinyl, azetidinyl, pyrrolidine, piperidinyl, piperizinyl or morpholinyl, each optionally substituted by 1, 2, 3 or 4 halo, CN, $NO_2$, $C_{1-4}$ alkoxy, heteroaryloxy, $C_{2-6}$ alkynyl, $C_{1-4}$ haloalkoxy, $NR^cC(O)R^d$, $NR^cC(O)OR^a$, $C(O)NR^cR^d$, $NR^eR^d$, $NR^eS(O)_2R^b$, $C_{1-4}$ haloalkyl, $C_{1-6}$ alkyl, heterocycloalkyl, aryl or heteroaryl, wherein each of said $C_{1-6}$ alkyl, aryl or heteroaryl is optionally substituted by 1, 2 or 3 halo, $C_{1-6}$ alkyl, $C_{1-4}$ haloalkyl, CN, $NO_2$, $OR^a$, $SR^a$, $C(O)NR^eR^d$, $NR^cC(O)R^d$ or $COOR^a$.

13. The compound of claim 1, or pharmaceutically acceptable salt thereof, wherein Cy is cyclohexyl or piperidinyl each optionally substituted by 1, 2, 3, 4 or 5 —W—X—Y—Z.

14. The compound of claim 1, or pharmaceutically acceptable salt thereof, wherein L is absent.

15. The compound of claim 1, or pharmaceutically acceptable salt thereof, wherein L is $SO_2$.

16. The compound of claim 1, or pharmaceutically acceptable salt thereof, wherein L is CO.

17. The compound of claim 1, or pharmaceutically acceptable salt thereof, wherein Q is A.

18. The compound of claim 1, or pharmaceutically acceptable salt thereof, wherein Q is —$(CR^1R^2)_m$-A and m is 1, 2 or 3.

19. The compound of claim 1, or pharmaceutically acceptable salt thereof, wherein A is cycloalkyl, heterocycloalkyl or heteroaryl, each optionally substituted by 1, 2, 3, 4 or 5 —W'—X'—Y'—Z', wherein W' is O or absent, X' is absent, and Y' is absent.

20. The compound of claim 1, or pharmaceutically acceptable salt thereof, wherein A is cycloalkyl or heterocycloalkyl, each optionally substituted with 1, 2, 3, 4 or 5 —W'—X'—Y'—Z'.

21. The compound of claim 1, or pharmaceutically acceptable salt thereof, wherein A is cycloalkyl or heterocycloalkyl, each optionally substituted with 1 or 2 —W'—X'—Y'—Z'.

22. The compound of claim 1, or pharmaceutically acceptable salt thereof, wherein A is cycloalkyl or heterocycloalkyl, each optionally substituted by 1, 2, 3, 4 or 5 OH, $C_{1-4}$ alkoxy, CN, $C_{1-4}$ alkyl, —O-heteroaryl, —($C_{1-4}$ alkyl)-OH, —($C_{1-4}$ alkyl)-CN, $COOR^a$, $C(O)NR^cR^d$ or $NR^cC(O)OR^a$.

23. The compound of claim 1, or pharmaceutically acceptable salt thereof, wherein A is cycloalkyl optionally substituted by 1, 2, 3, 4 or 5 OH, $C_{1-4}$ alkoxy, CN, $C_{1-4}$ alkyl, —O-heteroaryl, —($C_{1-4}$ alkyl)-OH, alkyl)-CN, $COOR^a$, $C(O)NR^cR^d$ or $NR^cC(O)OR^a$.

24. The compound of claim 1, or pharmaceutically acceptable salt thereof, wherein A is cyclopropyl, cyclobutyl, cyclopentyl, cyclohexyl, cycloheptyl or adamantyl, each optionally substituted by 1, 2, 3, 4 or 5 OH, $C_{1-4}$ alkoxy, CN, $C_{1-4}$ alkyl, —O-heteroaryl, —($C_{1-4}$ alkyl)-OH, —($C_{1-4}$ alkyl)-CN, $COOR^a$, $C(O)NR^cR^d$ or $NR^cC(O)OR^a$.

25. The compound of claim 1, or pharmaceutically acceptable salt thereof, wherein A is cyclopentyl or cyclohexyl, each substituted by 1, 2, 3, 4 or 5 OH, $C_{1-4}$ alkoxy, —O-heteroaryl or —($C_{1-4}$ alkyl)-OH.

26. The compound of claim 1, or pharmaceutically acceptable salt thereof, wherein A is cyclohexyl substituted by 1, 2, 3, 4 or 5 OH.

27. The compound of claim 1, or pharmaceutically acceptable salt thereof, wherein A is cyclohexyl substituted at the 4-position by at least one —W'—X'—Y'—Z'.

28. The compound of claim 1, or pharmaceutically acceptable salt thereof, wherein A is cyclohexyl substituted at the 4-position by at least one OH, CN, or —O—X'—Y'—Z'.

29. The compound of claim 1, or pharmaceutically acceptable salt thereof, wherein A is cyclohexyl substituted at the 4-position by 1 or 2 OH.

30. The compound of claim 1, or pharmaceutically acceptable salt thereof, wherein A is cyclohexyl substituted at the 4-position by 1 OH.

31. The compound of claim 1, or pharmaceutically acceptable salt thereof, wherein A is cycloalkyl or heterocycloalkyl, each substituted with at least two —W'—X'—Y'—Z', wherein two of said at least two —W'—X'—Y'—Z' are attached to the same atom and together with the atom to which they are attached form a 3-20 membered cycloalkyl or heterocycloalkyl group, each optionally substituted by 1, 2 or 3 —W''—X''—Y''—Z''.

32. The compound of claim 1, or pharmaceutically acceptable salt thereof, wherein A is heteroaryl optionally substituted with 1, 2, 3, 4 or 5 —W'—X'—Y'—Z'.

33. The compound of claim 1, or pharmaceutically acceptable salt thereof, wherein A is pyridyl, pyrimidinyl, triazinyl, furanyl thiazolyl, pyrazinyl, purinyl, quinazolinyl, quinolinyl, isoquinolinyl, pyrrolo[2,3-d]pyrimidinyl, or 1,3-benzothiazolyl, each optionally substituted by 1, 2, 3 or 4 $OR^a$, $SR^a$, halo, CN, $NO_2$, $C_{1-4}$ alkoxy, heteroaryloxy, $C_{2-6}$ alkynyl, $C_{1-4}$haloalkoxy, $NR^cC(O)R^d$, $NR^cC(O)OR^a$, $C(O)NR^cR^d$, $NR^cR^d$, $NR^eS(O)_2R^b$, $C_{1-4}$ haloalkyl, $C_{1-6}$ alkyl, heterocycloalkyl, aryl or heteroaryl, wherein each of said $C_{1-6}$ alkyl, aryl or heteroaryl is optionally substituted by 1, 2 or 3 halo, $C_{1-6}$ alkyl, $C_{1-4}$ haloalkyl, CN, $NO_2$, $OR^a$, $SR^a$, $C(O)NR^cR^d$, $NR^cC(O)R^d$ or $COOR^a$.

34. The compound of claim 1, or pharmaceutically acceptable salt thereof, wherein E is methylene, ethylene, or propylene.

35. The compound of claim 1, or pharmaceutically acceptable salt thereof, wherein E is ethylene.

36. The compound of claim 1, or pharmaceutically acceptable salt thereof, wherein $R^4$, $R^5$, $R^6$, $R^7$, $R^8$, $R^9$, $R^{10}$ and $R^{11}$ are each, independently, H, $OC(O)R^{a'}$, $OC(O)OR^{b'}$, $C(O)OR^{b'}$, $OC(O)NR^cR^{d'}$, $NR^cR^{d'}$, $NR^cC(O)R^{a'}$, $NR^cC(O)OR^{b'}$, $S(O)R^{a'}$, $S(O)NR^cR^{d'}$, $S(O)_2R^{a'}$, $S(O)_2NR^cR^{d'}$, $OR^{b'}$, $SR^{b'}$, $C_{1-10}$ alkyl, $C_{1-10}$ haloalkyl, $C_{2-10}$alkenyl, $C_{2-10}$ alkynyl, aryl, cycloalkyl, heteroaryl, heterocycloalkyl, arylalkyl, heteroarylalkyl, cycloalkylalkyl or heterocycloalkylalkyl.

37. The compound of claim 1, or pharmaceutically acceptable salt thereof, wherein $R^4$, $R^5$, $R^6$, $R^7$, $R^8$, $R^9$, $R^{10}$ and $R^{11}$ are each, independently, H, $C_{1-10}$alkyl or $C_{1-10}$ haloalkyl.

38. The compound of claim 1, or pharmaceutically acceptable salt thereof, wherein $R^4$, $R^5$, $R^6$, $R^7$, $R^8$, $R^9$, $R^{10}$ and $R^{11}$ are each H.

39. The compound of claim 1, or pharmaceutically acceptable salt thereof, wherein $R^{3a}$ and $R^{3b}$ are each H.

40. The compound of claim 1, or pharmaceutically acceptable salt thereof, wherein r is 1.

41. The compound of claim 1, or pharmaceutically acceptable salt thereof, wherein r is 2.

42. The compound of claim 1, or pharmaceutically acceptable salt thereof, wherein at least one of $R^1$ and $R^2$ is $C_{1-4}$ alkyl.

43. The compound of claim 1, or pharmaceutically acceptable salt thereof, wherein n1 is 2.

44. The compound of claim 1, or pharmaceutically acceptable salt thereof, having Formula II:

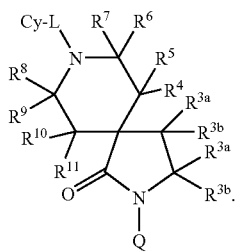

II

45. The compound of claim 1, or pharmaceutically acceptable salt thereof, having Formula III:

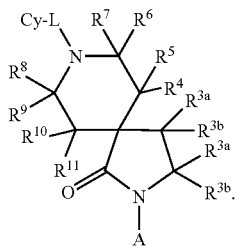

III

46. The compound of claim 45, or pharmaceutically acceptable salt thereof, wherein L is absent.

47. The compound of claim 45, or pharmaceutically acceptable salt thereof, wherein L is absent and $R^4$, $R^5$, $R^6$, $R^7$, $R^8$, $R^9$, $R^{10}$, $R^{11}$, $R^{3a}$ and $R^{3b}$ are each, independently, H, $C_{1-4}$ alkyl or $C_{1-4}$haloalkyl.

48. The compound of claim 47, or pharmaceutically acceptable salt thereof, wherein $R^4$, $R^5$, $R^6$, $R^7$, $R^8$, $R^9$, $R^{10}$, $R^{11}$, $R^{3a}$ and $R^{3b}$ are each, independently H.

49. The compound of claim 48, or pharmaceutically acceptable salt thereof, wherein A is cyclohexyl substituted by 1 or 2 OH.

50. A compound selected from:
  8-(3-Chloropyridin-2-yl)-2-cyclohexyl-2,8-diazaspiro[4.5]decan-1-one;
  8-(5-Chloro-3-fluoropyridin-2-yl)-2-cyclohexyl-2,8-diazaspiro[4.5]decan-1-one;
  2-(2-Cyclohexyl-1-oxo-2,8-diazaspiro[4.5]dec-8-yl)nicotinonitrile;
  2-Cyclohexyl-8-[3-(trifluoromethyl)pyridin-2-yl]-2,8-diazaspiro[4.5]decan-1-one;
  8-[5-(4-Chlorophenyl)pyridin-2-yl]-2-cyclohexyl-2,8-diazaspiro[4.5]decan-1-one;
  8-Benzoyl-2-cyclohexyl-2,8-diazaspiro[4.5]decan-1-one;
  2-Cyclohexyl-8-(cyclohexylcarbonyl)-2,8-diazaspiro[4.5]decan-1-one;
  2-Cyclohexyl-8-(piperidin-1-ylcarbonyl)-2,8-diazaspiro[4.5]decan-1-one;
  8-[(3-Chloro-2-methylphenyl)sulfonyl]-2-cyclohexyl-2,8-diazaspiro[4.5]decan-1-one;
  4-[2-(trans-4-Hydroxycyclohexyl)-1-oxo-2,8-diazaspiro[4.5]dec-8-yl]benzonitrile;
  3-Fluoro-4-[2-(trans-4-hydroxycyclohexyl)-1-oxo-2,8-diazaspiro[4.5]dec-8-yl]benzonitrile;
  3,5-Difluoro-4-[2-(trans-4-hydroxycyclohexyl)-1-oxo-2,8-diazaspiro[4.5]dec-8-yl]benzonitrile;
  8-(3-Fluoropyridin-2-yl)-2-(trans-4-hydroxycyclohexyl)-2,8-diazaspiro[4.5]decan-1-one;
  8-(3-Chloropyridin-2-yl)-2-(trans-4-hydroxycyclohexyl)-2,8-diazaspiro[4.5]decan-1-one;
  2-[2-(trans-4-Hydroxycyclohexyl)-1-oxo-2,8-diazaspiro[4.5]dec-8-yl]nicotinonitrile;
  2-(trans-4-Hydroxycyclohexyl)-8-[3-(trifluoromethyl)pyridin-2-yl]-2,8-diazaspiro[4.5]decan-1-one;
  2-(trans-4-Hydroxycyclohexyl)-8-[4-(trifluoromethyl)pyridin-2-yl]-2,8-diazaspiro[4.5]decan-1-one;
  2-[2-(trans-4-Hydroxycyclohexyl)-1-oxo-2,8-diazaspiro[4.5]dec-8-yl]isonicotinonitrile;
  8-(2-Chloropyridin-4-yl)-2-(trans-4-hydroxycyclohexyl)-2,8-diazaspiro[4.5]decan-1-one;
  8-(5-Fluoropyridin-2-yl)-2-(trans-4-hydroxycyclohexyl)-2,8-diazaspiro[4.5]decan-1-one;
  8-(5-Chloropyridin-2-yl)-2-(trans-4-hydroxycyclohexyl)-2,8-diazaspiro[4.5]decan-1-one;
  8-(5-Bromopyridin-2-yl)-2-(trans-4-hydroxycyclohexyl)-2,8-diazaspiro[4.5]decan-1-one;
  6-[2-(trans-4-Hydroxycyclohexyl)-1-oxo-2,8-diazaspiro[4.5]dec-8-yl]nicotinonitrile;
  2-(trans-4-Hydroxycyclohexyl)-8-[5-(trifluoromethyl)pyridin-2-yl]-2,8-diazaspiro[4.5]decan-1-one;
  8-(3,5-Difluoropyridin-2-yl)-2-(trans-4-hydroxycyclohexyl)-2,8-diazaspiro[4.5]decan-1-one;
  8-(5-Chloro-3-fluoropyridin-2-yl)-2-(trans-4-hydroxycyclohexyl)-2,8-diazaspiro[4.5]decan-1-one;
  8-(3,5-Dichloropyridin-2-yl)-2-(trans-4-hydroxycyclohexyl)-2,8-diazaspiro[4.5]decan-1-one;
  8-(5-Bromo-3-fluoropyridin-2-yl)-2-(trans-4-hydroxycyclohexyl)-2,8-diazaspiro[4.5]decan-1-one;
  8-(5-Bromo-3-chloropyridin-2-yl)-2-(trans-4-hydroxycyclohexyl)-2, diazaspiro[4.5]decan-1-one;
  8-[3-Chloro-5-(trifluoromethyl)pyridin-2-yl]-2-(trans-4-hydroxycyclohexyl)-2,8-diazaspiro[4.5]decan-1-one;
  2-(trans-4-Hydroxycyclohexyl)-8-[6-(trifluoromethyl)pyridin-2-yl]-2,8-diazaspiro[4.5]decan-1-one;
  8-(6-Fluoropyridin-2-yl)-2-(trans-4-hydroxycyclohexyl)-2,8-diazaspiro[4.5]decan-1-one;
  2-(trans-4-Hydroxycyclohexyl)-8-(3,5,6-trifluoro-4-methylpyridin-2-yl)-2,8-diazaspiro[4.5]decan-1-one;
  6-[2-(trans-4-Hydroxycyclohexyl)-1-oxo-2,8-diazaspiro[4.5]dec-8-yl]-2-methylnicotinonitrile;
  2-(trans-4-Hydroxycyclohexyl)-8-[6-methyl-4-(trifluoromethyl)pyridin-2-yl]-2,8-diazaspiro[4.5]decan-1-one;
  8-[3-Fluoro-4-(trifluoromethyl)pyridin-2-yl]-2-(trans-4-hydroxycyclohexyl)-2,8-diazaspiro[4.5]decan-1-one;
  8-(3-Fluoropyridin-4-yl)-2-(trans-4-hydroxycyclohexyl)-2,8-diazaspiro[4.5]decan-1-one;

8-(5-Fluoropyrimidin-2-yl)-2-(trans-4-hydroxycyclohexyl)-2,8-diazaspiro[4.5]decan-1-one;
8-(5-Ethylpyrimidin-2-yl)-2-(trans-4-hydroxycyclohexyl)-2,8-diazaspiro[4.5]decan-1-one;
8-(5-Bromopyrimidin-2-yl)-2-(trans-4-hydroxycyclohexyl)-2,8-diazaspiro[4.5]decan-1-one;
3-[2-(trans-4-Hydroxycyclohexyl)-1-oxo-2,8-diazaspiro[4.5]dec-8-yl]pyrazine-2-carbonitrile;
8-(1,3-Benzothiazol-2-yl)-2-(trans-4-hydroxycyclohexyl)-2,8-diazaspiro[4.5]decan-1-one;
8-(3-Fluoropyridin-2-yl)-2-(cis-4-hydroxycyclohexyl)-2,8-diazaspiro[4.5]decan-1-one;
8-(3-Chloropyridin-2-yl)-2-(cis-4-hydroxycyclohexyl)-2,8-diazaspiro[4.5]decan-1-one;
2-[2-(Cis-4-hydroxycyclohexyl)-1-oxo-2,8-diazaspiro[4.5]dec-8-yl]nicotinonitrile;
8-(3,5-Difluoropyridin-2-yl)-2-(cis-4-hydroxycyclohexyl)-2,8-diazaspiro[4.5]decan-1-one;
8-(2,5-Difluoropyridin-3-yl)-2-(cis-4-hydroxycyclohexyl)-2,8-diazaspiro[4.5]decan-1-one;
8-(5-Chloro-3-fluoropyridin-2-yl)-2-(cis-4-hydroxycyclohexyl)-2,8-diazaspiro[4.5]decan-1-one;
8-(5-Chloro-2-fluoropyridin-3-yl)-2-(cis-4-hydroxycyclohexyl)-2,8-diazaspiro[4.5]decan-1-one;
8-(3,5-Dichloropyridin-2-yl)-2-(cis-4-hydroxycyclohexyl)-2,8-diazaspiro[4.5]decan-1-one;
8-(5-Bromo-3-fluoropyridin-2-yl)-2-(cis-4-hydroxycyclohexyl)-2,8-diazaspiro[4.5]decan-1-one;
8-(5-Bromo-3-chloropyridin-2-yl)-2-(cis-4-hydroxycyclohexyl)-2,8-diazaspiro[4.5]decan-1-one;
2-(Cis-4-hydroxycyclohexyl)-8-[4-(trifluoromethyl)pyridin-2-yl]-2,8-diazaspiro[4.5]decan-1-one;
2-[2-(Cis-4-hydroxycyclohexyl)-1-oxo-2,8-diazaspiro[4.5]dec-8-yl]isonicotinonitrile;
8-[3-Fluoro-4-(trifluoromethyl)pyridin-2-yl]-2-(cis-4-hydroxycyclohexyl)-2,8-diazaspiro[4.5]decan-1-one;
2-(Cis-4-hydroxycyclohexyl)-8-pyrazin-2-yl-2,8-diazaspiro[4.5]decan-1-one;
8-(6-Chloropyrazin-2-yl)-2-(cis-4-hydroxycyclohexyl)-2,8-diazaspiro[4.5]decan-1-one;
8-(3,6-Dimethylpyrazin-2-yl)-2-(cis-4-hydroxycyclohexyl)-2,8-diazaspiro[4.5]decan-1-one;
Methyl {6-[2-(cis-4-hydroxycyclohexyl)-1-oxo-2,8-diazaspiro[4.5]dec-8-yl]-5-methylpyridin-3-+yl}carbamate;
Ethyl {6-[2-(cis-4-hydroxycyclohexyl)-1-oxo-2,8-diazaspiro[4.5]dec-8-yl]-5-methylpyridin-3-yl}carbamate;
Ethynyl {6-[2-(cis-4-hydroxycyclohexyl)-1-oxo-2,8-diazaspiro[4.5]dec-8-yl]-5-methylpyridin-3-yl}carbamate;
Propyl {6-[2-(cis-4-hydroxycyclohexyl)-1-oxo-2,8-diazaspiro[4.5]dec-8-yl]-5-methylpyridin-3-yl}carbamate;
N-{6-[2-(cis-4-hydroxycyclohexyl)-1-oxo-2,8-diazaspiro[4.5]dec-8-yl]-5-methylpyridin-3-yl}cyclopropanecarboxamide;
2-(Cis-4-hydroxycyclohexyl)-8-[3-methyl-5-(2-oxopyrrolidin-1-yl)pyridin-2-yl]-2,8-diazaspiro[4.5]decan-1-one;
2-(Cis-4-hydroxycyclohexyl)-8-[3-methyl-5-(2-oxo-1,3-oxazolidin-3-yl)pyridin-2-yl]-2,8-diazaspiro[4.5]decan-1-one;
2-(Cis-4-hydroxycyclohexyl)-8-[3-methyl-5-(2-oxopiperidin-1-yl)pyridin-2-yl]-2,8-diazaspiro[4.5]decan-1-one;
2-(Cis-4-hydroxycyclohexyl)-8-[3-methyl-5-(2-oxo-1,3-oxazinan-3-yl)pyridin-2-yl]-2,8-diazaspiro[4.5]decan-1-one;
Methyl {5-chloro-6-[2-(cis-4-hydroxycyclohexyl)-1-oxo-2,8-diazaspiro[4.5]dec-8-yl]pyridin-3-yl}carbamate;
Methyl {6-[2-(cis-4-hydroxycyclohexyl)-1-oxo-2,8-diazaspiro[4.5]dec-8-yl]pyridin-3-yl}carbamate;
Ethyl {5-chloro-6-[2-(cis-4-hydroxycyclohexyl)-1-oxo-2,8-diazaspiro[4.5]dec-8-yl]pyridin-3-yl}carbamate;
Ethyl {6-[2-(cis-4-hydroxycyclohexyl)-1-oxo-2,8-diazaspiro[4.5]dec-8-yl]pyridin-3-yl}carbamate;
Prop-2-yn-1-yl {5-chloro-6-[2-(cis-4-hydroxycyclohexyl)-1-oxo-2,8-diazaspiro[4.5]dec-8-yl]pyridin-3-yl}carbamate;
Ethynyl {6-[2-(cis-4-hydroxycyclohexyl)-1-oxo-2,8-diazaspiro[4.5]dec-8-yl]pyridin-3-yl}carbamate;
Propyl {5-chloro-6-[2-(cis-4-hydroxycyclohexyl)-1-oxo-2,8-diazaspiro[4.5]dec-8-yl]pyridin-3-yl}carbamate;
Propyl {6-[2-(cis-4-hydroxycyclohexyl)-1-oxo-2,8-diazaspiro[4.5]dec-8-yl]pyridin-3-yl}carbamate;
3-Fluoro-4-[2-(cis-4-hydroxycyclohexyl)-1-oxo-2,8-diazaspiro[4.5]dec-8-yl]benzonitrile;
4-Fluoro-3-[2-(cis-4-hydroxycyclohexyl)-1-oxo-2,8-diazaspiro[4.5]dec-8-yl]benzonitrile;
3,5-Difluoro-4-[2-(cis-4-hydroxycyclohexyl)-1-oxo-2,8-diazaspiro[4.5]dec-8-yl]benzonitrile;
3,4-Difluoro-5-[2-(cis-4-hydroxycyclohexyl)-1-oxo-2,8-diazaspiro[4.5]dec-8-yl]benzonitrile;
3-[5-Chloro-6-[2-(cis-4-hydroxycyclohexyl)-1-oxo-2,8-diazaspiro[4.5]dec-8-yl]pyridin-3-yl]-N-methylbenzamide;
8-(5-Bromo-2-fluorophenyl)-2-(cis-4-hydroxycyclohexyl)-2,8-diazaspiro[4.5]decan-1-one;
8-{2-Fluoro-5-[6-(pyrrolidin-1-ylcarbonyl)pyridin-3-yl]phenyl}-2-(cis-4-hydroxycyclohexyl)-2,8-diazaspiro[4.5]decan-1-one;
8-{5-[6-(Azetidin-1-ylcarbonyl)pyridin-3-yl]-2-fluorophenyl}-2-(cis-4-hydroxycyclohexyl)-2,8-diazaspiro[4.5]decan-1-one;
4'-Fluoro-3'-[2-(cis-4-hydroxycyclohexyl)-1-oxo-2,8-diazaspiro[4.5]dec-8-yl]biphenyl-4-carboxamide;
4'-Fluoro-3'-[2-(cis-4-hydroxycyclohexyl)-1-oxo-2,8-diazaspiro[4.5]dec-8-yl]-N-methylbiphenyl-4-carboxamide;
4'-Fluoro-3 [2-(cis-4-hydroxycyclohexyl)-1-oxo-2,8-diazaspiro[4.5]dec-8-yl]biphenyl-3-carboxamide;
4'-Fluoro-3 [2-(cis-4-hydroxycyclohexyl)-1-oxo-2,8-diazaspiro[4.5]dec-8-yl]-N,N-dimethylbiphenyl-3-carboxamide;
4'-Fluoro-3 [2-(cis-4-hydroxycyclohexyl)-1-oxo-2,8-diazaspiro[4.5]dec-8-yl]-N-isopropylbiphenyl-3-carboxamide;
N-Ethyl-5-{4-fluoro-3-[2-(cis-4-hydroxycyclohexyl)-1-oxo-2,8-diazaspiro[4.5]dec-8-yl]phenyl}pyridine-2-carboxamide;
8-(2-Fluoro-5-pyridin-4-ylphenyl)-2-(cis-4-hydroxycyclohexyl)-2,8-diazaspiro[4.5]decan-1-one; and
8-[2-Fluoro-5-(1-methyl-1H-pyrazol-4-yl)phenyl]-2-(cis-4-hydroxycyclohexyl)-2,8-diazaspiro[4.5]decan-1-one;
or a pharmaceutically acceptable salt thereof.

51. A composition comprising a compound of claim 1, or pharmaceutically acceptable salt thereof, and at least one pharmaceutically acceptable carrier.

52. A method of treating obesity in a patient, comprising administering to said patient a therapeutically effective amount of a compound or a pharmaceutically acceptable salt thereof according to claim 1.

53. A method of treating type 2 diabetes in a patient comprising administering to said patient a therapeutically effective amount of a compound or pharmaceutically acceptable salt thereof according to claim 1.

54. A compound of Formula I:

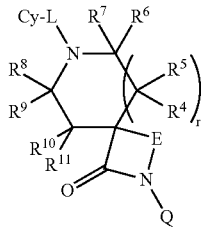

I or pharmaceutically acceptable salt thereof, wherein:

Cy is aryl, heteroaryl, cycloalkyl, or heterocycloalkyl, each optionally substituted with 1, 2, 3, 4 or 5 —W—X—Y—Z;

L is absent;

Q is —(CR$^1$R$^2$)$_m$-A;

A is cycloalkyl, heterocycloalkyl or heteroaryl, each optionally substituted with 1, 2,3,4 or 5 —W'—X'—Y'—Z';

E is —(CR$^{3a}$R$^{3b}$)$_{n1}$—;

R$^1$, R$^2$, and R$^{2a}$ are independently selected from H and C$_{1-8}$ alkyl;

R$^{3a}$ and R$^{3b}$ are independently selected from H, halo, C$_{1-4}$ alkyl, C$_{1-4}$ haloalkyl, C$_{2-4}$ alkenyl, and C$_{2-4}$ alkynyl;

R$^4$, R$^5$, R$^6$, R$^7$, R$^8$, R$^9$, R$^{10}$ and R$^{11}$ are independently selected from H, OC(O)R$^{a'}$, OC(O)OR$^{b'}$, C(O)R$^{b'}$, OC(O)NR$^{c'}$R$^{d'}$, NR$^{c'}$R$^{d'}$, NR$^{c'}$C(O)R$^{a'}$, NR$^{c'}$C(O)OR$^{b'}$, S(O)R$^{a'}$, S(O)NR$^{c'Rd'}$, S(O)$_2$R$^{a'}$, S(O)$_2$NR$^{c'}$R$^{d'}$, OR$^{b'}$, SR$^{b'}$, halo, C$_{1-10}$ alkyl, C$_{1-10}$ haloalkyl, C$_{2-10}$ alkenyl, C$_{2-10}$ alkynyl, aryl, cycloalkyl, heteroaryl, heterocycloalkyl, arylalkyl, heteroarylalkyl, cycloalkylalkyl, and heterocycloalkylalkyl, wherein said C$_{1-10}$ alkyl, C$_{1-10}$ haloalkyl, C$_{2-10}$ alkenyl, C$_{2-10}$ alkynyl, aryl, cycloalkyl, heteroaryl, heterocycloalkyl, arylalkyl, heteroarylalkyl, cycloalkylalkyl or heterocycloalkylalkyl is optionally substituted by 1, 2, or 3 R$^{14}$;

or R$^4$ and R$^5$ together with the carbon atom to which they are attached form a 3-14 membered cycloalkyl or heterocycloalkyl group which is optionally substituted by R$^{14}$;

or R$^6$ and R$^7$ together with the carbon atom to which they are attached form a 3-14 membered cycloalkyl or heterocycloalkyl group which is optionally substituted by R$^{14}$;

or R$^8$ and R$^9$ together with the carbon atom to which they are attached form a 3-14 membered cycloalkyl or heterocycloalkyl group which is optionally substituted by R$^{14}$;

or R$^{10}$ and R$^{11}$ together with the carbon atom to which they are attached form a 3-14 membered cycloalkyl or heterocycloalkyl group which is optionally substituted by R$^{14}$;

or R$^4$ and R$^6$ together with the carbon atom to which they are attached form a 3-7 membered fused cycloalkyl group or 3-7 membered fused heterocycloalkyl group which is optionally substituted by R$^{14}$;

or R$^6$ and R$^8$ together with the carbon atom to which they are attached form a 3-7 membered fused cycloalkyl group or 3-7 membered fused heterocycloalkyl group which is optionally substituted by R$^{14}$;

or R$^4$ and R$^9$ together form a C$_{1-3}$ alkylene bridge which is optionally substituted by R$^{14}$;

or R$^4$ and R$^{10}$ together form a C$_{1-3}$ alkylene bridge which is optionally substituted by R$^{14}$;

or R$^6$ and R$^{10}$ together form a C$_{1-3}$ alkylene bridge which is optionally substituted by R$^{14}$;

or R$^9$ and R$^{10}$ together form a C$_{1-3}$ alkylene bridge which is optionally substituted by R$^{14}$;

R$^{14}$ is halo, C$_{1-4}$ alkyl, C$_{1-4}$ haloalkyl, aryl, cycloalkyl, heteroaryl, heterocycloalkyl, CN, NO$_2$, OR$^{a'}$, SR$^{a'}$, C(O)R$^{b'}$, C(O)NR$^{c'}$R$^{d'}$, C(O)OR$^{d'}$, C(O)OR$^{a'}$, OC(O)R$^{b'}$, OC(O)NR$^{c'}$R$^{d'}$, NR$^{c'}$R$^{d'}$, NR$^{c'}$C(O)R$^{d'}$, NR$^{c'}$C(O)OR$^{a'}$, S(O)R$^{b'}$, S(O)NR$^{c'}$R$^{d'}$, S(O)$_2$R$^{b'}$, or S(O)$_2$NR$^{c'}$R$^{d'}$;

W, W' and W" are independently selected from absent, C$_{1-6}$ alkylenyl, C$_{2-6}$ alkenylenyl, C$_{2-6}$ alkynylenyl, O, S, NR$^e$, CO, COO, CONR$^e$, SO, SO$_2$, SONR$^e$, and NR$^e$CONR$^f$, wherein said C$_{1-6}$ alkylenyl, C$_{2-6}$ alkenylenyl, C$_{2-6}$ alkynylenyl are each optionally substituted by 1, 2 or 3 substituents independently selected from halo, OH, C$_{1-4}$ alkoxy, C$_{1-4}$ haloalkoxy, amino, C$_{1-4}$ alkylamino, and C$_{2-8}$ dialkylamino;

X, X' and X" are independently selected from absent, C$_{1-6}$ alkylenyl, C$_{2-6}$ alkenylenyl, C$_{2-6}$ alkynylenyl, aryl, cycloalkyl, heteroaryl, and heterocycloalkyl, wherein said C$_{1-6}$ alkylenyl, C$_{2-6}$ alkenylenyl, C$_{2-6}$ alkynylenyl, aryl, cycloalkyl, heteroaryl, or heterocycloalkyl is optionally substituted by one or more substituents independently selected from halo, C$_{1-6}$ alkyl, oxo, CN, NO$_2$, OH, C$_{1-4}$ alkoxy, C$_{1-4}$haloalkoxy, amino, C$_{1-4}$ alkylamino, and C$_{2-8}$ dialkylamino;

Y, Y' and Y" are independently selected from absent, C$_{1-6}$ alkylenyl, C$_{2-6}$ alkenylenyl, C$_{2-6}$ alkynylenyl, O, S, NR$^e$, CO, COO, CONR$^e$, SO, SO$_2$, SONR$^e$, and NR$^e$CONR$^f$, wherein said C$_{1-6}$ alkylenyl, C$_{2-6}$ alkenylenyl, C$_{2-6}$ alkynylenyl are each optionally substituted by 1, 2 or 3 substituents independently selected from halo, OH, C$_{1-4}$ alkoxy, C$_{1-4}$ haloalkoxy, amino, C$_{1-4}$ alkylamino, and C$_{2-8}$ dialkylamino;

Z, Z' and Z" are independently selected from H, halo, CN, NO$_2$, OH, C$_{1-4}$ alkoxy, C$_{1-4}$ haloalkoxy, amino, C$_{1-4}$ alkylamino, C$_{2-8}$ dialkylamino, C$_{1-6}$ alkyl, C$_{2-6}$ alkenyl, C$_{2-6}$ alkynyl, aryl, cycloalkyl, heteroaryl, and heterocycloalkyl, wherein said C$_{1-6}$ alkyl, C$_{2-6}$ alkenyl, C$_{2-6}$ alkynyl, aryl, cycloalkyl, heteroaryl, or heterocycloalkyl is optionally substituted by 1, 2 or 3 substituents independently selected from halo, oxo, C$_{1-6}$ alkyl, C$_{2-6}$ alkenyl, C$_{2-6}$ alkynyl, C$_{1-4}$ haloalkyl, aryl, cycloalkyl, heteroaryl, heterocycloalkyl, halosulfanyl, CN, NO$_2$, OR$^a$, SR$^a$, C(O)R$^b$, C(O)NR$^c$R$^d$, C(O)OR$^a$, OC(O)R$^b$, OC(O)NR$^c$R$^d$, NR$^c$R$^d$, NR$^c$C(O)R$^d$, NR$^c$C(O)OR$^a$, NR$^e$S(O)$_2$R$^b$, C(=NR$^i$)NR$^c$R$^d$, NR$^c$C(=NR$^i$)NR$^c$R$^d$, S(O)R$^b$, S(O)NR$^c$R$^d$, S(O)$_2$R$^b$, and S(O)$_2$NR$^c$R$^d$;

wherein two —W—X—Y—Z attached to the same atom optionally form a 3-20 membered cycloalkyl or heterocycloalkyl group, each optionally substituted by 1, 2 or 3 —W"—X"—Y"—Z";

wherein two —W'—X'—Y'—Z' attached to the same atom optionally form a 3-20 membered cycloalkyl or heterocycloalkyl group, each optionally substituted by 1, 2 or 3 —W"—X"—Y"—Z";

wherein —W—X—Y—Z is other than H;

wherein —W'—X'—Y'—Z' is other than H;

wherein —W"—X"—Y"—Z" is other than H;

R$^a$ and R$^{a'}$ are independently selected from H, C$_{1-6}$ alkyl, C$_{1-6}$ haloalkyl, C$_{2-6}$ alkenyl, C$_{2-6}$ alkynyl, aryl, cycloalkyl, heteroaryl, and heterocycloalkyl, wherein said C$_{1-6}$ alkyl, C$_{1-6}$ haloalkyl, C$_{2-6}$ alkenyl, C$_{2-6}$ alkynyl, aryl, cycloalkyl, heteroaryl, or heterocycloalkyl is optionally substituted with H, OH, amino, halo, $C_{1-6}$ alkyl, $C_{1-6}$ haloalkyl, aryl, arylalkyl, heteroaryl, heteroarylalkyl, cycloalkyl, or heterocycloalkyl;

$R^b$ and $R^{b'}$ are independently selected from H, $C_{1-6}$ alkyl, $C_{1-6}$ haloalkyl, $C_{2-6}$ alkenyl, $C_{2-6}$ alkynyl, aryl, cycloalkyl, heteroaryl, heterocycloalkyl, arylalkyl, heteroarylalkyl, cycloalkylalkyl, and heterocycloalkylalkyl, wherein said $C_{1-6}$ alkyl, $C_{1-6}$ haloalkyl, $C_{2-6}$ alkenyl, $C_{2-6}$ alkynyl, aryl, cycloalkyl, heteroaryl, heterocycloalkyl, arylalkyl, heteroarylalkyl, cycloalkylalkyl, or heterocycloalkylalkyl is optionally substituted with H, OH, amino, halo, $C_{1-6}$ alkyl, $C_{1-6}$ haloalkyl, $C_{1-6}$haloalkyl, aryl, arylalkyl, heteroaryl, heteroarylalkyl, cycloalkyl or heterocycloalkyl;

$R^c$ and $R^d$ are independently selected from H, $C_{1-10}$ alkyl, $C_{1-6}$ haloalkyl, $C_{2-6}$ alkenyl, $C_{2-6}$ alkynyl, aryl, heteroaryl, cycloalkyl, heterocycloalkyl, arylalkyl, heteroarylalkyl, cycloalkylalkyl, and heterocycloalkylalkyl, wherein said $C_{1-10}$ alkyl, $C_{1-6}$ haloalkyl, $C_{2-6}$ alkenyl, $C_{2-6}$ alkynyl, aryl, heteroaryl, cycloalkyl, heterocycloalkyl, arylalkyl, heteroarylalkyl, cycloalkylalkyl, or heterocycloalkylalkyl is optionally substituted with H, OH, amino, halo, $C_{1-6}$ alkyl, $C_{1-6}$ haloalkyl, $C_{1-6}$ haloalkyl, aryl, arylalkyl, heteroaryl, heteroarylalkyl, cycloalkyl or heterocycloalkyl;

or $R^c$ and $R^d$ together with the N atom to which they are attached form a 4-, 5-, 6- or 7-membered heterocycloalkyl group;

$R^{c'}$ and $R^{d'}$ are independently selected from H, $C_{1-10}$ alkyl, $C_{1-6}$ haloalkyl, $C_{2-6}$ alkenyl, $C_{2-6}$ alkynyl, aryl, heteroaryl, cycloalkyl, heterocycloalkyl, arylalkyl, heteroarylalkyl, cycloalkylalkyl, and heterocycloalkylalkyl, wherein said $C_{1-10}$ alkyl, $C_{1-6}$ haloalkyl, $C_{2-6}$ alkenyl, $C_{2-6}$ alkynyl, aryl, heteroaryl, cycloalkyl, heterocycloalkyl, arylalkyl, heteroarylalkyl, cycloalkylalkyl or heterocycloalkylalkyl is optionally substituted with H, OH, amino, halo, $C_{1-6}$ alkyl, $C_{1-6}$ haloalkyl, $C_{1-6}$ haloalkyl, aryl, arylalkyl, heteroaryl, heteroarylalkyl, cycloalkyl or heterocycloalkyl;

or $R^{c'}$ and $R^{d'}$ together with the N atom to which they are attached form a 4-, 5-, 6- or 7-membered heterocycloalkyl group;

$R^e$ and $R^f$ are independently selected from H, $C_{1-10}$ alkyl, $C_{1-6}$ haloalkyl, $C_{2-6}$ alkenyl, $C_{2-6}$ alkynyl, aryl, heteroaryl, cycloalkyl, heterocycloalkyl, arylalkyl, heteroarylalkyl, cycloalkylalkyl, heterocycloalkylalkyl, wherein said $C_{1-10}$ alkyl, $C_{1-6}$ haloalkyl, $C_{2-6}$ alkenyl, $C_{2-6}$ alkynyl, aryl, heteroaryl, cycloalkyl, heterocycloalkyl, arylalkyl, heteroarylalkyl, cycloalkylalkyl, or heterocycloalkylalkyl is optionally substituted with H, OH, amino, halo, $C_{1-6}$ alkyl, $C_{1-6}$ haloalkyl, $C_{1-6}$ haloalkyl, aryl, arylalkyl, heteroaryl, heteroarylalkyl, cycloalkyl or heterocycloalkyl;

or $R^e$ and $R^f$ together with the N atom to which they are attached form a 4-, 5-, 6- or 7-membered heterocycloalkyl group;

$R^i$ is H, CN, or $NO_2$;

m is 0, 1, 2 or 3;

n1 is 2; and r is 1.

55. A method of treating obesity in a patient comprising administering to said patient a therapeutically effective amount of a compound or pharmaceutically acceptable salt thereof according to claim 54.

56. A method of treating type 2 diabetes in a patient comprising administering to said patient a therapeutically effective amount of a compound or pharmaceutically acceptable salt thereof according to claim 54.

\* \* \* \* \*